(12) United States Patent
Anthony et al.

(10) Patent No.: US 12,302,900 B2
(45) Date of Patent: *May 20, 2025

(54) PROTOPORPHYRINOGEN OXIDASE INHIBITORS

(71) Applicant: Enko Chem, Inc., Mystic, CT (US)

(72) Inventors: Neville John Anthony, Northborough, MA (US); Paul Galatsis, Newton, MA (US); David Jeffrey Lauffer, Stow, MA (US); Peter Stchur, III, Waterford, CT (US)

(73) Assignee: Enko Chem, Inc., Mystic, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/393,184

(22) Filed: Dec. 21, 2023

(65) Prior Publication Data

US 2024/0130365 A1    Apr. 25, 2024

Related U.S. Application Data

(63) Continuation of application No. 18/355,800, filed on Jul. 20, 2023, now Pat. No. 11,889,833, which is a continuation of application No. PCT/US2023/060450, filed on Jan. 11, 2023.

(60) Provisional application No. 63/299,866, filed on Jan. 14, 2022.

(51) Int. Cl.
*A01N 41/06* (2006.01)
*A01P 13/00* (2006.01)
*C07C 311/51* (2006.01)

(52) U.S. Cl.
CPC .............. *A01N 41/06* (2013.01); *A01P 13/00* (2021.08); *C07C 311/51* (2013.01)

(58) Field of Classification Search
None
See application file for complete search history.

(56) References Cited

U.S. PATENT DOCUMENTS

| | | |
|---|---|---|
| 2,891,855 A | 6/1959 | Hans et al. |
| 3,060,084 A | 10/1962 | Littler |
| 3,235,361 A | 2/1966 | Loux |
| 3,299,566 A | 1/1967 | Macmullen |
| 3,309,192 A | 3/1967 | Luckenbaugh |
| 3,920,442 A | 11/1975 | Albert et al. |
| 4,144,050 A | 3/1979 | Frensch et al. |
| 4,172,714 A | 10/1979 | Albert |
| 4,761,373 A | 8/1988 | Anderson et al. |
| 4,940,835 A | 7/1990 | Shah et al. |
| 5,013,659 A | 5/1991 | Bedbrook et al. |
| 5,180,587 A | 1/1993 | Moore |
| 5,188,642 A | 2/1993 | Shah et al. |
| 5,208,030 A | 5/1993 | Hoy et al. |
| 5,232,701 A | 8/1993 | Ogawa et al. |
| 5,304,732 A | 4/1994 | Anderson et al. |
| 5,561,236 A | 10/1996 | Leemans et al. |
| 5,608,147 A | 3/1997 | Kaphammer |
| 5,627,061 A | 5/1997 | Barry et al. |
| 5,633,435 A | 5/1997 | Barry et al. |
| 5,646,024 A | 7/1997 | Leemans et al. |
| 5,670,454 A | 9/1997 | Grossmann et al. |
| 5,804,425 A | 9/1998 | Barry et al. |
| 6,100,446 A | 8/2000 | Streber et al. |
| 6,153,401 A | 11/2000 | Streber et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,376,754 B1 | 4/2002 | Schillinger et al. |
| 6,791,014 B2 | 9/2004 | Garcon et al. |
| 7,105,724 B2 | 9/2006 | Weeks et al. |

(Continued)

FOREIGN PATENT DOCUMENTS

| | | |
|---|---|---|
| CN | 102246775 B | 5/2013 |
| CN | 106417357 A | 2/2017 |

(Continued)

OTHER PUBLICATIONS

Machine english translation of WO-2004029030-A1, 2004, accessed google patents Jul. 13, 2024, no pagination.*

(Continued)

*Primary Examiner* — Erin E Hirt
(74) *Attorney, Agent, or Firm* — Morrison & Foerster LLP

(57) ABSTRACT

The present invention relates to protoporphyrinogen IX oxidase (PPO) inhibitors of the general formula (I)

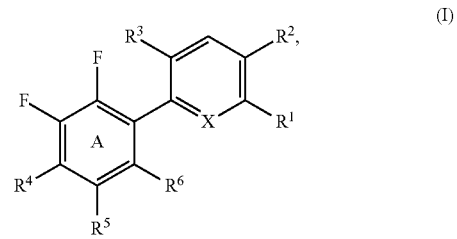

where the variables are defined herein. The invention features processes and intermediates for preparing the compounds of formula (I), compositions comprising them, and their use as herbicides—e.g., for controlling harmful plants. The invention also features methods for controlling unwanted vegetation comprising allowing an herbicidal effective amount of at least one PPO inhibitor of formula (I) to act on plants, their seed, and/or their habitat.

37 Claims, No Drawings

(56) References Cited

U.S. PATENT DOCUMENTS

| | | | |
|---|---|---|---|
| 8,952,207 | B2 | 2/2015 | Daugulis et al. |
| 11,889,833 | B2* | 2/2024 | Anthony ............... A01N 37/06 |
| 2003/0217381 | A1 | 11/2003 | Croughan |
| 2008/0042127 | A1 | 2/2008 | Watson |
| 2009/0076266 | A1 | 3/2009 | Daugulis et al. |
| 2012/0110701 | A1 | 5/2012 | Garizi et al. |
| 2012/0110702 | A1 | 5/2012 | Yap et al. |
| 2013/0288897 | A1 | 10/2013 | Babcock et al. |
| 2014/0171308 | A1 | 6/2014 | Lo et al. |
| 2014/0171310 | A1 | 6/2014 | Lo et al. |
| 2014/0171312 | A1 | 6/2014 | Lo et al. |
| 2014/0171314 | A1 | 6/2014 | Lo et al. |
| 2014/0213448 | A1 | 7/2014 | Buysse et al. |
| 2014/0274688 | A1 | 9/2014 | Fischer et al. |
| 2014/0296068 | A1 | 10/2014 | Garizi et al. |
| 2015/0111730 | A1 | 4/2015 | Niyaz et al. |
| 2015/0111731 | A1 | 4/2015 | Garizi et al. |
| 2015/0111732 | A1 | 4/2015 | Walsh et al. |
| 2015/0111733 | A1 | 4/2015 | Walsh et al. |
| 2015/0111734 | A1 | 4/2015 | Zhang et al. |
| 2015/0111735 | A1 | 4/2015 | Zhang et al. |
| 2015/0245615 | A1 | 9/2015 | Kuhn et al. |
| 2015/0366204 | A1 | 12/2015 | Baum et al. |
| 2016/0000760 | A1 | 1/2016 | Bilotta et al. |
| 2016/0024026 | A1 | 1/2016 | Fischer et al. |
| 2016/0024027 | A1 | 1/2016 | Fischer et al. |
| 2016/0060245 | A1 | 3/2016 | Buysse et al. |
| 2018/0289001 | A1 | 10/2018 | Lalgudi et al. |

FOREIGN PATENT DOCUMENTS

| | | |
|---|---|---|
| CN | 107372506 A | 11/2017 |
| CN | 106146454 B | 8/2018 |
| CN | 108373461 B | 8/2019 |
| CN | 113651819 A | 11/2021 |
| CN | 109535070 B | 3/2022 |
| CN | 112390759 B | 6/2022 |
| CN | 114956924 A | 8/2022 |
| CN | 115010600 A | 9/2022 |
| CN | 116082267 A | 5/2023 |
| DE | 3246493 A1 | 6/1984 |
| DE | 102004010716 A1 | 8/2004 |
| DE | 102004012192 A1 | 9/2004 |
| DE | 102006059710 A1 | 6/2008 |
| EP | 2065373 A1 | 6/2009 |
| EP | 2065374 A1 | 6/2009 |
| EP | 2112143 A1 | 10/2009 |
| EP | 3210469 A1 | 8/2017 |
| EP | 3194393 B1 | 3/2020 |
| GB | 2095558 A | 10/1982 |
| IN | 201831010638 A | 9/2019 |
| JP | 2015086221 A | 5/2015 |
| JP | 2020079269 A | 5/2020 |
| JP | 2021152083 A | 9/2021 |
| WO | WO-1991013546 A1 | 9/1991 |
| WO | WO-1996038567 A2 | 12/1996 |
| WO | WO-1997049816 A1 | 12/1997 |
| WO | WO-2003024222 A1 | 3/2003 |
| WO | WO-2004029030 A1 * | 4/2004 ............ A01N 43/54 |
| WO | WO-2004055191 A1 | 7/2004 |
| WO | WO-2004082382 A1 | 9/2004 |
| WO | WO-2005012270 A2 | 2/2005 |
| WO | WO-2005020673 A1 | 3/2005 |
| WO | WO-2005044007 A1 | 5/2005 |
| WO | WO-2005053407 A1 | 6/2005 |
| WO | WO-2005107437 A2 | 11/2005 |
| WO | WO-2006060634 A2 | 6/2006 |
| WO | WO-2007006300 A1 | 1/2007 |
| WO | WO-2007034755 A1 * | 3/2007 ............ A01N 41/10 |
| WO | WO-2008021800 A2 | 2/2008 |
| WO | WO-2008051633 A2 | 5/2008 |
| WO | WO-2008074474 A1 | 6/2008 |
| WO | WO-2008125362 A1 | 10/2008 |
| WO | WO-2008152091 A2 | 12/2008 |
| WO | WO-2009068170 A2 | 6/2009 |
| WO | WO-2009068171 A2 | 6/2009 |
| WO | WO-2009129953 A1 | 10/2009 |
| WO | WO-2010025870 A1 | 3/2010 |
| WO | WO-2010126580 A1 | 11/2010 |
| WO | WO-2011017513 A1 | 2/2011 |
| WO | WO-2011073143 A1 | 6/2011 |
| WO | WO-2011085221 A2 | 7/2011 |
| WO | WO-2011098417 A1 | 8/2011 |
| WO | WO-2011117272 A2 | 9/2011 |
| WO | WO-2012080975 A1 | 6/2012 |
| WO | WO-2012130798 A1 | 10/2012 |
| WO | WO-2012177813 A1 | 12/2012 |
| WO | WO-2013009791 A1 | 1/2013 |
| WO | WO-2013019824 A2 | 2/2013 |
| WO | WO-2013026866 A2 | 2/2013 |
| WO | WO-2013062980 A1 | 5/2013 |
| WO | WO-2013062981 A1 | 5/2013 |
| WO | WO-2013106254 A1 | 7/2013 |
| WO | WO-2013162715 A2 | 10/2013 |
| WO | WO-2013162716 A2 | 10/2013 |
| WO | WO-2014030090 A1 | 2/2014 |
| WO | WO-2014048827 A1 | 4/2014 |
| WO | WO-2014074333 A1 | 5/2014 |
| WO | WO-2014126580 A1 | 8/2014 |
| WO | WO-2014175465 A1 | 10/2014 |
| WO | WO-2015016373 A1 | 2/2015 |
| WO | WO-2015022636 A2 | 2/2015 |
| WO | WO-2015022639 A2 | 2/2015 |
| WO | WO-2015022640 A2 | 2/2015 |
| WO | WO-2015092706 A1 | 6/2015 |
| WO | WO-2015167795 A1 | 11/2015 |
| WO | WO-2015175719 A1 | 11/2015 |
| WO | WO-2016042435 A1 | 3/2016 |
| WO | WO-2016062585 A1 | 4/2016 |
| WO | WO-2016102435 A2 | 6/2016 |
| WO | WO-2016203377 A1 | 12/2016 |
| WO | WO-2017012922 A1 | 1/2017 |
| WO | WO-2017012965 A1 | 1/2017 |
| WO | WO-2017012966 A1 | 1/2017 |
| WO | WO-2017023778 A1 | 2/2017 |
| WO | WO-2017039969 A1 | 3/2017 |
| WO | WO-2017087672 A1 | 5/2017 |
| WO | WO-2017112589 A1 | 6/2017 |
| WO | WO-2017198859 A1 | 11/2017 |
| WO | WO-2018019860 A1 | 2/2018 |
| WO | WO-2018022777 A1 | 2/2018 |
| WO | WO-2018146079 A1 | 8/2018 |
| WO | WO-2019150311 A1 | 8/2019 |
| WO | WO-2019165159 A1 | 8/2019 |
| WO | WO-2019180533 A1 | 9/2019 |
| WO | WO-2019236717 A1 | 12/2019 |
| WO | WO-2020133092 A1 | 7/2020 |
| WO | WO-2020154349 A1 | 7/2020 |
| WO | WO-2021011722 A1 | 1/2021 |
| WO | WO-2021153786 A1 | 8/2021 |
| WO | WO-2022181793 A1 | 9/2022 |
| WO | WO-2022182623 A1 | 9/2022 |
| WO | WO-2022235264 A1 | 11/2022 |
| WO | WO-2023001679 A1 | 1/2023 |
| WO | WO-2023036707 A1 | 3/2023 |
| WO | WO-2023044364 A1 | 3/2023 |
| WO | WO-2023074510 A1 | 5/2023 |

OTHER PUBLICATIONS

Machine english translation of WO-2007034755-A1, 2007, accessed google patents Jul. 13, 2024, no pagination.*

Fernandez-Moreno et al. (2018). "A novel amino acid substitution (Arg-132-His) in protoporphyrinogen oxidase 2 confers broad spectrum pro-inhibitor resistance in Lolium rigidum," Weed Science Society of America (WSSA) annual meeting abstract. 1 page.

Fu et al. (2014). "Hot Fusion: An Efficient Method to Clone Multiple DNA Fragments as Well as Inverted Repeats without Ligase," PLoS One 9(12):e115318. 20 pages.

Giacomini et al. (2017). "Two new PPX2 mutations associated with resistance to PPO-inhibiting herbicides in Amaranthus palmeri," Pest Management Science 73(8):1559-1563, 16 pages.

(56) References Cited

OTHER PUBLICATIONS

Hao et al. (2011). "Protoporphyrinogen oxidase inhibitor: an ideal target for herbicide discovery," Chimia 65(12):961-9.

International Search Report and Written Opinion mailed on Jun. 28, 2023, for PCT Patent Application No. PCT/US2023/060450 filed on Jan. 11, 2023. 11 pages.

Invitation to Pay Additional Fees mailed on Mar. 23, 2023, for PCT Patent Application No. PCT/US2023/060450 filed on Jan. 11, 2023. 3 pages.

Jacobs and Jacobs (1982). "Assay for enzymatic protoporphyrinogen oxidation, a late step in heme synthesis" Enyzme 28(2-3):206-19.

Jain et al. (2013). "Biphenyls and their derivatives as synthetically and pharmacologically important aromatic structural moieties," Arabian Journal of Chemistry 10:S2051-S2066.

Jiang et al. (2013). "Grafting Imparts Glyphosate Resistance in Soybean," Weed Technology 27(2):412-416.

Lee et al. (1993). "Cellular localization of protoporphyrinogen-oxidizing activities of etiolated barley (*Hordeum vulgare* L.) leaves," Plant Physiology 102(3): 881-889.

Li et al. (2005). "Development of PPO inhibitor-resistant cultures and crops," Pest Management Science 61(3):277-285.

Matringe et al. (1989). "Protoporphyrinogen oxidase as a molecular target for diphenyl ether herbicides," Biochemistry Journal 260(1): 231-235.

Patzoldt et al. (2006). "A codon deletion confers resistance to herbicides inhibiting protoporphyrinogen oxidase," Proc. Natl. Acad. Sci. USA 103(33):12329-34.

Pubchem CID 119020984, "2,3-Difluoro-3'-methylsulfanylbiphenyl". Created May 17, 2016; modified Feb. 25, 2023, available online at <https://pubchem.ncbi.nlm.nih.gov/compound/119020984>, 9 pages.

Pubchem CID 134617890, "2',4'-Dichloro-2,3,4,5,6-pentafluoro-biphenyl". Created Jul. 9, 2018; modified Feb. 25, 2023, available online at <https://pubchem.ncbi.nlm.nih.gov/compound/134617890>, 9 pages.

Rangani, et al. (2008). "A novel mutation in protoporphyrinogen oxidase IX (PPO) confers broad resistance to PPO inhibitors," Weed Science Society of America (WSSA) annual meeting abstract. 1 page.

Rousonelos et al. (2012). "Characterization of a common ragweed (*Ambrosia artemisiifolia*) population resistant to ALS- and PPO-inhibiting herbicides," Weed Sci. 60(3):335-344.

Shoup et al. (2003). "Common waterhemp (*Amaranthus rudis*) resistance to protoporphyrinogen oxidase-inhibiting herbicides," Weed Sci. 51:145-150.

Shukla et al. (2009). "Precise genome modification in the crop species *Zea mays* using zinc-finger nucleases," Nature 459(7245):437-41, 7 pages.

\* cited by examiner

PROTOPORPHYRINOGEN OXIDASE INHIBITORS

CROSS-REFERENCE TO RELATED APPLICATIONS

This application is a continuation of U.S. application Ser. No. 18/355,800 filed Jul. 20, 2023, which is a continuation of PCT/US2023/060450 filed on Jan. 11, 2023 which claims priority to U.S. Provisional Patent Application No. 63/299,866, filed Jan. 14, 2022, each of which is incorporated herein by reference in its entirety.

FIELD

The present invention relates to protoporphyrinogen IX oxidase (PPO) inhibitors useful as herbicides. In particular, the present invention relates to certain fluorinated phenyl compounds, compositions comprising such compounds, processes for making such compounds and compositions, and methods for using such compounds for crop protection and to control unwanted vegetation.

BACKGROUND

Herbicides that inhibit protoporphyrinogen oxidase (hereinafter referred to as Protox or PPO; EC:1.3.3.4), a key enzyme in the biosynthesis of protoporphyrin IX, have been used for selective weed control since the 1960s. PPO catalyzes the last common step in chlorophyll and heme biosynthesis, which is the oxidation of protoporphyrinogen IX to protoporphyrin IX [Matringe M. et al., Protoporphyrinogen oxidase as a molecular target for diphenyl ether herbicides, *Biochemistry Journal* (1989) 260: 231-235]. Application of PPO-inhibiting herbicides results in the accumulation of protoporphyrinogen IX in the chloroplast and mitochondria, which is believed to leak into the cytosol where it is oxidized by a peroxidase. When exposed to light, protoporphyrin IX causes formation of singlet oxygen in the cytosol and the formation of other reactive oxygen species, which can cause lipid peroxidation and membrane disruption leading to rapid cell death [Lee H. J. et al., Cellular localization of protoporphyrinogen-oxidizing activities of etiolated barley leaves, *Plant Physiology* (1993) 102: 881].

To date, thousands of PPO inhibitors have been reported in the literature, with about 30 currently used as herbicides to decimate weeds in fields [Hao, G. F., et al., Protoporphyrinogen oxidase inhibitor: an ideal target for herbicide discovery, *Chimia* (2011) 65, 961-969]. PPO-inhibiting herbicides include many different structural classes of molecules, including diphenyl ethers (e.g. lactofen, acifluorfen, acifluorfen methyl ester, or oxyfluorfen); oxadiazoles (e.g. oxadiazon); cyclic imides [e.g. S-23142, N-(4-chloro-2-fluoro-5-propargyloxyphenyl)-3,4,5,6-tetrahydrophthalimide, chlorophthalim, N-(4-chlorophenyl)-3,4,5,6-tetrahydrophthalimide)]; phenyl pyrazoles (e.g. TNPP-ethyl, ethyl 2-[1-(2,3,4-trichlorophenyl)-4-nitropyrazolyl-5-oxy]propionate, M&B 39279); pyridine derivatives (e.g. LS 82-556); and phenopylate and its O-phenylpyrrolidino- and piperidinocarbamate analogs (Kramer W., ed., *Modern Crop Protection Compounds, 2nd Ed., Vol 1: Herbicides*, (2012) Wiley-VCH, Weinheim, Germany). Many of these compounds competitively inhibit the normal reaction catalyzed by the enzyme, apparently acting as substrate analogs.

The herbicidal properties of these known compounds towards harmful plants, however, are not always entirely satisfactory. Herbicide resistant weeds present a serious problem for efficient weed control because such resistant weeds are increasingly widespread and thus weed control by the application of herbicides is no longer effective, causing a huge problem to farmers. Resistance to PPO herbicides has been slow to evolve (about four decades from first commercialization), and to date has been confirmed in 13 weed species [Heap I, *The International Survey of Herbicide Resistant Weeds*. Available online: www.weedscience.org (October 2019)]. The first weed to evolve resistance to PPO herbicides was waterhemp (*Amaranthus tuberculatus*) in 2001 [Shoup D. E., et al., Common waterhemp (*Amaranthus rudis*) resistance to protoporphyrinogen oxidase-inhibiting herbicides *Weed Sci.* (2003) 51:145-150]. Resistance to PPO herbicides in weedy species has been attributed to target-site mutation in the PPX2 gene. For example, a unique target-site amino acid deletion (Gly210) and Arg98Leu substitution confer PPO resistance in waterhemp [Patzoldt W. L., et al., A codon deletion confers resistance to herbicides inhibiting protoporphyrinogen oxidase. *Proc. Natl. Acad. Sci. USA* (2006) 103:12329-12334] and common ragweed [Rousonelos, et al., Characterization of a common ragweed (*Ambrosia artemisiifolia*) population resistant to ALS- and PPO-inhibiting herbicides, *Weed Sci.* (2012) 60:335-344], respectively.

Thus, there is a need for novel methods to effectively control weeds, including herbicide resistant weeds and in particular PPO resistant weeds, which at the same time is tolerated by the useful plants (crops) in question.

BRIEF SUMMARY

Accordingly, in one aspect, provided are compounds having formula (I):

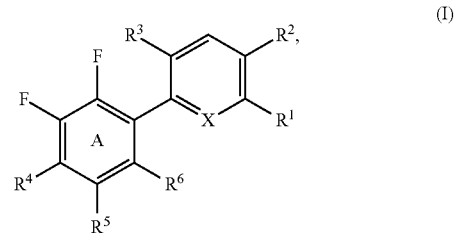

or a salt thereof, wherein Ring A contains at least 4 F atom substituents and X and $R^1$-$R^6$ are as defined herein.

In certain embodiments, provided are compounds having formula (II):

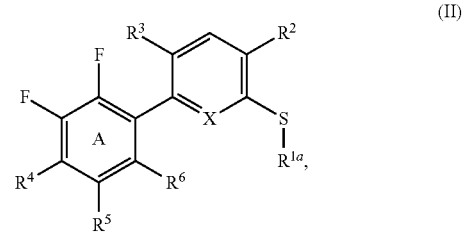

or a salt thereof, wherein X and $R^2$-$R^6$ and $R^{1a}$ are as defined elsewhere herein.

In certain embodiments, provided are compounds having formula (III):

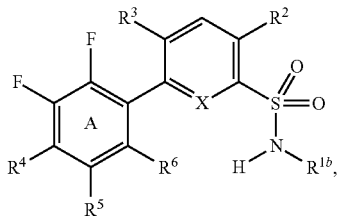

or a salt thereof, wherein X and $R^2$-$R^6$ and $R^{1g}$ are as defined elsewhere herein.

In other aspects, provided is also an agricultural composition (including, in some variations, herbicidal compositions) that includes a compound of formulas (I), (II), or (III), or a salt thereof, in a herbicidally effective amount and at least one component selected from the group consisting of surfactants, solid diluents and liquid diluents (e.g., formulations). In some variations, the salt is an agriculturally suitable salt. In some embodiments, the composition optionally further includes at least one additional active ingredient. In one variation, the additional active ingredient may be an herbicide and/or herbicide safener.

In yet another aspect, provided are also processes for making the above-identified compounds, salts, and compositions.

In certain aspects, provided are compounds that are intermediates for making one or more compounds of the invention, including one or more compounds of Table 1, or a salt thereof.

In yet other aspects, provided are also methods for controlling the growth of undesired vegetation comprising contacting the vegetation or its environment with a herbicidally effective amount of a compound of the invention, its salt, or a composition that includes a compound of the invention as described herein.

DETAILED DESCRIPTION

In one aspect, provided are compounds having formula (I):

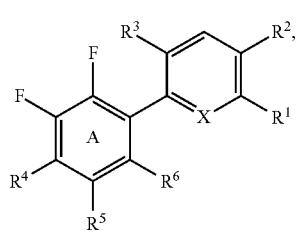

or suitable salt thereof, wherein
X is CH or N;
$R^1$ is $-SR^{1a}$ or $-S(O)_2R^{1b}$;
$R^{1a}$ is $C_{1-4}$alkyl optionally substituted with phenyl, C(O)OR$^{1c}$, or C(O)N(R$^{1c}$)$_2$;
each $R^{1c}$ is independently, H, CH$_2$CH$_2$OC(O)R$^{1d}$, or optionally substituted $C_{1-4}$alkyl, wherein the optional substituents are $C_{3-6}$cycloalkyl, C(O)OC$_{1-4}$alkyl, or up to 3 F atoms, or two R$^{1c}$ with an intervening nitrogen atom form a 5-6 membered ring optionally substituted with C(O)OH or C(O)OC$_{1-4}$alkyl;
$R^{1d}$ is $C_{1-4}$alkyl or $C_{1-4}$alkenyl;
$R^{1b}$ is CH$_2$C(O)C$_{1-4}$alkyl or N(R$^{1e}$)R$^{1f}$;
$R^{1e}$ is H, $C_{1-4}$alkyl, $C_{1-4}$alkenyl, $C_{1-4}$alkynyl, C(O)C$_{1-2}$alkyl, or OC$_{1-4}$alkyl;
$R^{1f}$ is H, $C_{1-6}$alkyl, C(O)C(O)C$_{1-4}$alkyl, C(O)R$^{1g}$, or S(O)$_2$R$^{1g}$, or R$^{1e}$ and R$^{1f}$ together with the intervening nitrogen atom form a 5-6 membered ring, optionally containing up to two C(O) ring members;
$R^{1g}$ is $C_{1-4}$alkyl, $C_{1-4}$alkenyl, phenyl, Het, N(R$^h$)$_2$, OC$_{1-4}$alkyl, $C_{3-6}$cycloalkyl, or CH$_2$(OCH$_2$CH$_2$)$_4$CH$_3$, wherein each alkyl group is optionally substituted with up to 3 F atoms, phenyl, $C_{3-6}$cycloalkyl, OH, OC$_{1-4}$alkyl, wherein each cycloalkyl group is optionally substituted with OH or OC$_{1-4}$alkyl, wherein each phenyl is optionally substituted with up to 3 Cl or F atoms, and wherein Het is a 5-6 membered heterocyclic ring containing up to two ring members selected from O, N, S, or S(O)$_2$ and optionally substituted with OH or OC$_{1-4}$alkyl;
each $R^h$ is, independently H, $C_{1-4}$alkyl, benzyl, or phenyl;
each of $R^2$ and $R^3$ is Cl or F; and
each of $R^4$, $R^5$, and $R^6$ is F or H, wherein Ring A comprises at least 4 F atoms.

In one embodiment, $R^1$ is $-SR^{1a}$ and $R^{1a}$ is $C_{1-4}$alkyl substituted with phenyl, C(O)OR$^{1c}$, or C(O)N(R$^{1c}$)$_2$. In another embodiment. $R^1$ is $-S(O)_2R^{1b}$ and $R^{1b}$ is CH$_2$C(O)C$_{1-4}$alkyl. In a further embodiment, $R^1$ is $-S(O)_2R^{1b}$ and $R^{1b}$ is N(R$^{1e}$)R$^{1f}$.

In one embodiment, the invention features compounds having formula (II):

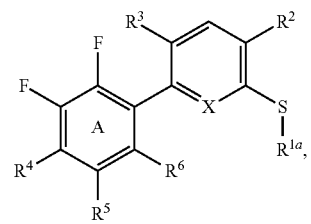

or a salt thereof.

In a further embodiment, each of $R^4$, $R^5$, and $R^6$ is F. In another further embodiment, each of $R^4$ and $R^6$ is F. In yet another further embodiment, each of $R^4$ and $R^5$ is F.

In another further embodiment, $R^{1a}$ is CH(CH$_3$)CONHCH$_2$CH$_2$CO$_2$C$_{1-4}$alkyl.

In one embodiment, the invention features compounds having formula (III):

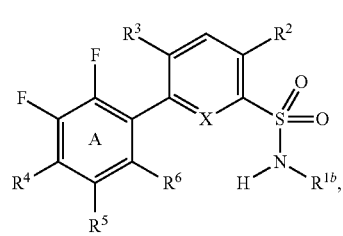

or salt thereof.

In a further embodiment, each of $R^4$, $R^5$, and $R^6$ is F. In another further embodiment, each of $R^4$ and $R^6$ is F. In yet another further embodiment, each of $R^4$ and $R^5$ is F.

In another embodiment, $R^{1g}$ is $C(O)C_{1-6}$alkyl, $C(O)C_{3-6}$cycloalkyl, $C(O)OC_{1-6}$alkyl, or $C(O)OC_{3-6}$cycloalkyl.

In one aspect, provided is a compound of formula (IV):

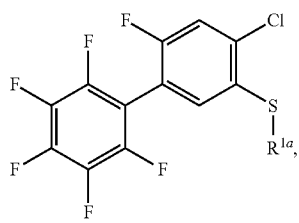

(IV)

or a salt thereof (including an agriculturally suitable salt thereof), wherein $R^{1a}$ is defined herein for formula (I).

In another aspect, provided is a compound of formula (V):

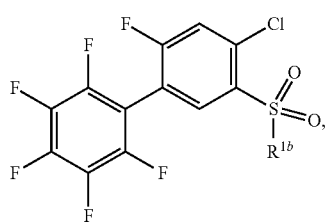

(V)

or a salt thereof (including an agriculturally suitable salt thereof), wherein $R^{1b}$ is defined herein for formula (I).

In yet another aspect, provided is a compound of formula (VI):

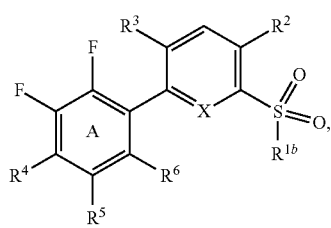

(VI)

or a salt thereof (including an agriculturally suitable salt thereof), wherein each of $R^2$, $R^3$, $R^4$, and $R^6$ are independently Cl or F, and wherein each of A, X, $R^{1b}$, and $R^5$ are defined herein for formula (I).

In another aspect, provided is a compound of formula (VII):

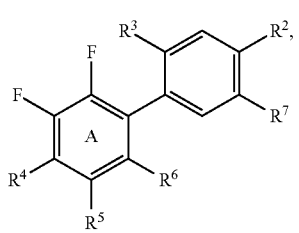

(VII)

or a salt thereof (including an agriculturally suitable salt thereof), wherein $R^1$ is —$SR^7$, or —$S(O)_2NHR^{7b}$;

$R^7$, is H, $C_{1-6}$alkyl, $C(O)C_{1-6}$alkyl, or $C(O)OC_{1-6}$alkyl, each $C_{1-6}$alkyl optionally substituted with phenyl, $CO_2R^{7b}$, or $C(O)N(R^{7b})_2$;

each $R^{7b}$ is, independently, H, phenyl, $C_{3-6}$cycloalkyl, or $C_{1-6}$alkyl optionally substituted with up to 3 F atoms, phenyl, $C_{2-4}$alkenyl, $C_{2-4}$alkynyl, or $C_{3-6}$cycloalkyl;

each of $R^4$, $R^5$, and $R^6$ is F or H; and

Ring A comprises at least 4 F atoms.

In an embodiment, each of $R^4$, $R^5$, and $R^6$ is F.

In another embodiment, $R^7$ is S—$R^{7a}$ and each of $R^4$ and $R^6$ are F. In another embodiment, $R^7$, is $C_{1-6}$alkyl substituted with $CO_2R^{7b}$ or $C(O)N(R^{7b})_2$. In a further embodiment, two $R^{7b}$ groups and an intervening nitrogen atom form a 5 to 6 membered heterocyclic ring substituted with $CO_2R^x$. In another embodiment, each of $R^4$, $R^5$, and $R^6$ is F.

In another embodiment, $R^7$ is $SO_2$—NH—$R^{7a}$ and each of $R^4$ and $R^6$ are F. In one embodiment, $R^{7a}$ is —$C(O)N(R^{7b})_2$. In another embodiment, $R^{7a}$ is —$C(O)C_{1-6}$alkyl or —$C(O)OC_{1-6}$alkyl. In a further embodiment, each of $R^4$, $R^5$, and $R^6$ is F.

In some variations of the foregoing, the salt may be an agriculturally suitable salt. In certain variations, the agriculturally suitable salt is a salt that exhibits herbicidal activity, or that is or can be converted in plants, water, or soil into a compound or salt with herbicidal activity.

In some aspects, provided is a compound selected from the compounds listed in Table 1 below, or a salt thereof (including an agriculturally suitable salt thereof).

TABLE 1

Exemplary Compounds

1

2

TABLE 1-continued

Exemplary Compounds

TABLE 1-continued

Exemplary Compounds

TABLE 1-continued

Exemplary Compounds 27, 28, 29, 30, 31, 32, 33, 34, 35, 36

TABLE 1-continued

Exemplary Compounds

TABLE 1-continued

Exemplary Compounds 47, 48, 49, 50, 51, 52, 53, 54, 55, 56, 57

TABLE 1-continued
Exemplary Compounds
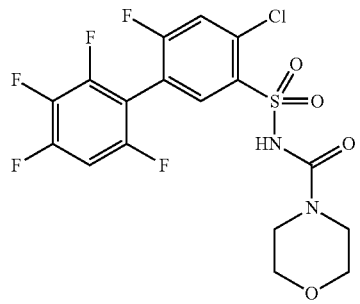 [SMILES: O=C(NS(=O)(=O)c1cc(-c2c(F)cc(F)c(F)c2F)c(F)cc1Cl)N1CCOCC1]
58
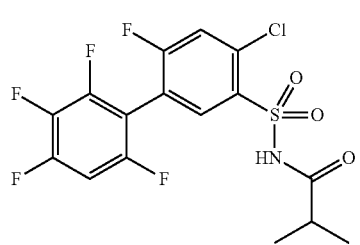 [SMILES: CC(C)C(=O)NS(=O)(=O)c1cc(-c2c(F)cc(F)c(F)c2F)c(F)cc1Cl]
59
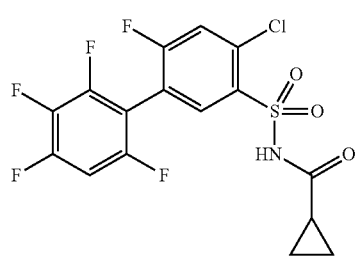 [SMILES: O=C(NS(=O)(=O)c1cc(-c2c(F)cc(F)c(F)c2F)c(F)cc1Cl)C1CC1]
60
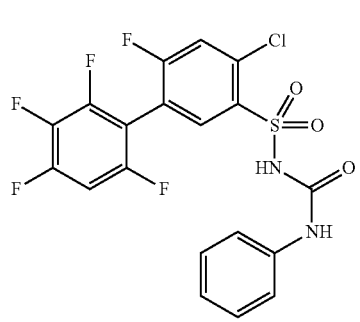 [SMILES: O=C(Nc1ccccc1)NS(=O)(=O)c1cc(-c2c(F)cc(F)c(F)c2F)c(F)cc1Cl]
61
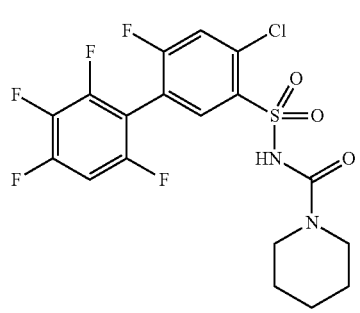
62
TABLE 1-continued
Exemplary Compounds
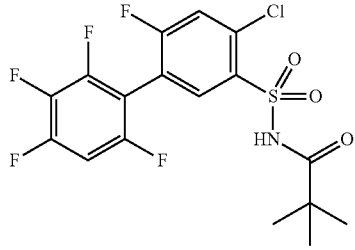 [SMILES: CC(C)(C)C(=O)NS(=O)(=O)c1cc(-c2c(F)cc(F)c(F)c2F)c(F)cc1Cl]
63
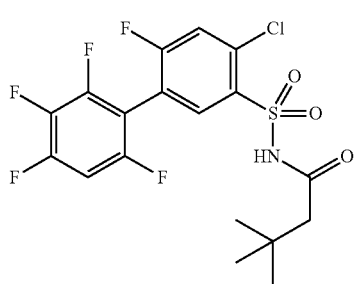 [SMILES: CC(C)(C)CC(=O)NS(=O)(=O)c1cc(-c2c(F)cc(F)c(F)c2F)c(F)cc1Cl]
64
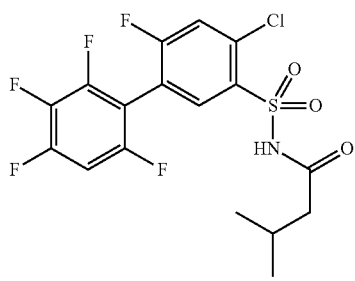 [SMILES: CC(C)CC(=O)NS(=O)(=O)c1cc(-c2c(F)cc(F)c(F)c2F)c(F)cc1Cl]
65
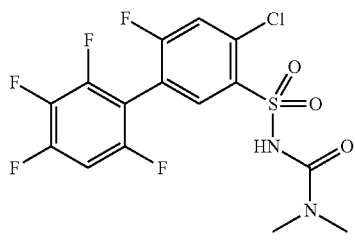
66
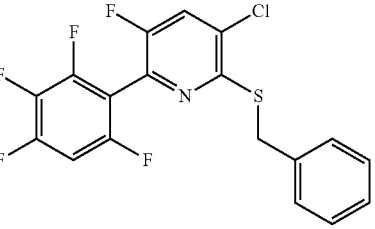
67
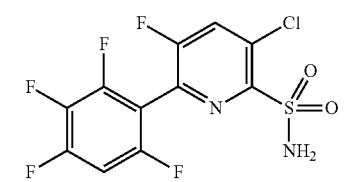
68

TABLE 1-continued

Exemplary Compounds

69 [chemical structure]

70 [chemical structure]

71 [chemical structure]

72 [chemical structure]

73 [chemical structure]

74 [chemical structure]

TABLE 1-continued

Exemplary Compounds

75 [chemical structure]

76 [chemical structure]

77 [chemical structure]

78 [chemical structure]

79 [chemical structure]

In some variations, provided is Compound 1-14 or 67, or a salt thereof (including an agriculturally suitable salt thereof). In some variations, Compounds 1-14 or 67, or a salt thereof (including an agriculturally suitable salt thereof) comprise formula (IV) as defined herein. In some variations, provided is Compound 15-24, or a salt thereof (including an agriculturally suitable salt thereof). In some variations, Compounds 15-24, or a salt thereof (including an agriculturally suitable salt thereof) comprise formula (V) as defined herein. In one variation, provided is Compound 18, or a salt thereof (including an agriculturally suitable salt thereof). In some variations, provided is Compound 25-66 or 68-79, or a salt thereof (including an agriculturally suitable salt thereof). In some variations, each of Compounds 25-66 or 68-79, or a salt thereof (including an agriculturally suitable salt thereof) comprise formula (VI) as defined herein. In one variation, provided is Compound 26, or a salt thereof (including an agriculturally suitable salt thereof). In another variation, provided is Compound 50, or a salt thereof (including an agriculturally suitable salt thereof). In yet another variation, provided is Compound 51, or a salt thereof (including an agriculturally suitable salt thereof). In some variations, provided is Compound 52-53, or a salt thereof (including an agriculturally suitable salt thereof). In some variations, each of Compounds 52-53, or a salt thereof (including an agriculturally suitable salt thereof) comprise formula (VI) as defined herein.

In another aspect, the invention features an agricultural composition comprising a compound of the invention, or a salt thereof, and at least one additional component that serves as a carrier.

In one embodiment, at least one additional component of the agricultural composition is a surfactant or a diluent.

In another embodiment, the composition is an herbicidal composition.

In another aspect, the invention features a method of controlling undesired vegetation, the method comprising contacting the vegetation or its environment with an herbicidally effective amount of a compound of the invention, or agriculturally acceptable salt thereof.

In one embodiment, the undesired vegetation includes weeds. In a further embodiment, the undesired vegetation includes protoporphyrinogen IX oxidase (PPO) inhibitor-resistant weeds. In yet another further embodiment, the PPO inhibitor-resistant weeds have a dG210 mutation.

In one embodiment, a compound or composition of the invention is applied at a rate of 1 to 100 g per 10,000 m$^2$.

In one embodiment, contacting the undesired vegetation or its environment with a compound or composition of the invention leads to post-emergence control of the undesired vegetation. In a further embodiment, the undesired vegetation is at least 60% controlled. In another embodiment the undesired vegetation is at least 80% controlled. In yet another embodiment, the undesired vegetation is at least 90% controlled.

In one embodiment, contacting the undesired vegetation or its environment with a compound or composition of the invention leads to pre-emergence control of the undesired vegetation. In a further embodiment, the undesired vegetation is at least 60% controlled. In another embodiment the undesired vegetation is at least 80% controlled. In yet another embodiment, the undesired vegetation is at least 90% controlled.

Definitions

As used herein, the terms "comprises," "comprising." "includes," "including," "has," "having," "contains," "containing," "characterized by," or any other variation thereof, are intended to cover a non-exclusive inclusion, subject to any limitation explicitly indicated. For example, a composition, mixture, process, or method that includes or comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Further, unless expressly stated to the contrary, "or" refers to an inclusive 'or' and not to an exclusive 'or.' For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling," used either alone or in a combination of words means a young plant developing from the embryo of a seed.

As referred to herein, the term "broadleaf," used either alone or in terms such as "broadleaf weed" means dicot or dicotyledon, a term used to describe a group of angiosperms characterized by embryos having two cotyledons.

In the above recitations, the term "alkyl," used either alone or in compound words such as "alkylthio" or "haloalkyl" includes straight-chain or branched alkyl, such as, methyl, ethyl, n-propyl, i-propyl, or the different butyl, pentyl, or hexyl isomers. "Alkenyl" includes straight-chain or branched alkenes such as ethenyl, 1-propenyl, 2-propenyl, and the different butenyl, pentenyl, and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl, and the different butynyl, pentynyl, and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy, and hexyloxy isomers.

"Cycloalkyl" includes, for example, cyclopropyl, cyclobutyl, cyclopentyl, and cyclohexyl.

The term "halogen" or "halo" either alone or in compound words such as "haloalkyl," or when used in descriptions such as "alkyl substituted with halogen" includes fluorine, chlorine, bromine, or iodine.

The total number of carbon atoms in a substituent group is indicated by the "$C_i$-$C_j$" or "$C_{i-j}$" prefix, where i and j are numbers from 1 to 10. For example, $C_{1-4}$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—. $CH_3OCH_2CH_2$—, or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, the substituents (when they exceed 1) are independently selected from the group of defined substituents, e.g., $(R^1)_m$, where m is 0, 1, 2 or 3. Further, when the subscript indicates a range, e.g. $(R)_{i-j}$, then the number of substituents may be selected from the integers between 'i' and 'j' inclusive. When a group contains a substituent, which can be hydrogen (H), for example, then when this substituent is taken as hydrogen, it is recognized that this is equivalent to the group being unsubstituted. When a variable group is shown to be optionally attached to a position, then hydrogen may be at the position even if not recited in the variable group definition. When one or more positions on a group are said to be "not substituted" or "unsubstituted," then hydrogen atoms are attached to take up any free valency.

"Aromatic" indicates that each of the ring atoms is essentially in the same plane and has a p-orbital perpendicular to the ring plane, and that $(4n+2)\pi$ electrons, where n is a positive integer, are associated with the ring to comply with Hückel's rule. The term "aromatic ring system" denotes a carbocyclic or heterocyclic ring system in which at least one ring of the ring system is aromatic.

The term "nonaromatic ring system" denotes a carbocyclic or heterocyclic ring system that may be fully saturated, as well as partially or fully unsaturated, provided that none of the rings in the ring system are aromatic.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

The term "acceptable salt" or "salt" when related to a compound of the invention includes cations or anions. Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl, or benzyl— preferably ammonium, methylammonium, isopropylammonium, dimethylammonium, diethylammonium, diisopropylammonium, trimethylammonium, triethylammonium, tris (isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl) ammonium (diolamine salt), tris(2-hydroxyethyl) ammonium (trolamine salt), tris(2-hydroxypropyl) ammonium, benzylthmethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl) sulfoxonium, and finally the salts of polybasic amines such as N,N-bis-(3-aminopropyl)methylamine, and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate, and also the anions of $C_1$-$C_4$-alkanoic acids—preferably formate, acetate, propionate, and butyrate.

As used herein, the terms "undesirable vegetation" and "harmful plants" are synonyms.

Preparation of Compounds of the Invention

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve-volume set of *Comprehensive Heterocyclic Chemistry II*, A. R. Katritzky, C. W. Rees and E. F. V. Scriven editors-in-chief. Pergamon Press, Oxford, 1996.

Compounds of the invention can exist as one or more stereoisomers. The various stereoisomers include enantiomers, diastereomers, atropisomers, and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form. For a comprehensive discussion of all aspects of stereoisomerism, see Ernest L. Eliel and Samuel H. *Stereochemistry of Organic Compounds*, John Wiley & Sons, New York, 1994. Compounds of the invention typically exist in more than one form, and the formulas of the invention thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e., different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical, and biological properties as crystal shape, density, hardness, color, chemical stability, melting point, hygroscopicity, suspensibility, dissolution rate, and biological availability. One skilled in the art will appreciate that a polymorph of a compound of the invention can exhibit beneficial effects (e.g., suitability for preparation of useful formulations, improved biological performance) relative to another polymorph or a mixture of polymorphs of the same compound. Preparation and isolation of a particular polymorph of a compound of a compound of the invention can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art recognizes that because in the environment and under physiological conditions salts of chemical compounds are in equilibrium with their corresponding nonsalt forms, salts share the biological utility of the nonsalt forms. Thus, a wide variety of salts of compounds of the invention are useful for control of undesired vegetation (i.e., are agriculturally suitable). The salts of compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic, or valeric acids. When a compound of the invention contains an acidic moiety such as a carboxylic acid or phenol, salts also include those formed with organic or inorganic bases such as pyridine, triethylamine, or ammonia, or amides, hydrides, hydroxides or carbonates of sodium, potassium, lithium, calcium, magnesium, or barium.

Moreover, the invention features processes and intermediates for preparing compounds of the invention. These compounds can be prepared by general methods known in the art of synthetic organic chemistry. One or more of the following methods and variations as described in Schemes 1 & 2 can be used.

In one general example, the compounds of formulas (II) & (III) can be prepared as shown in Scheme 1.

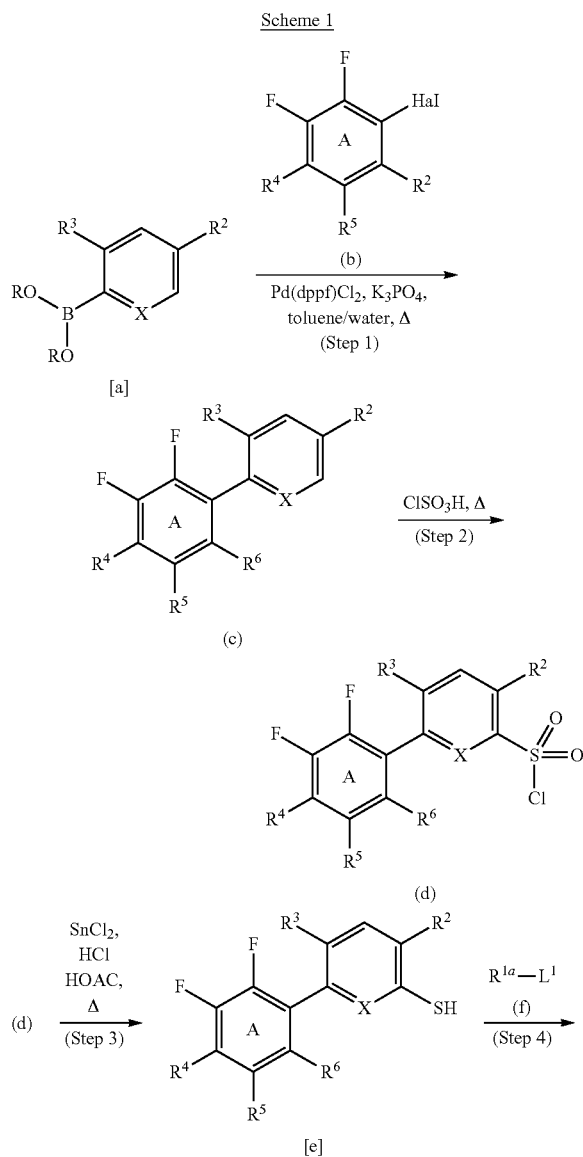

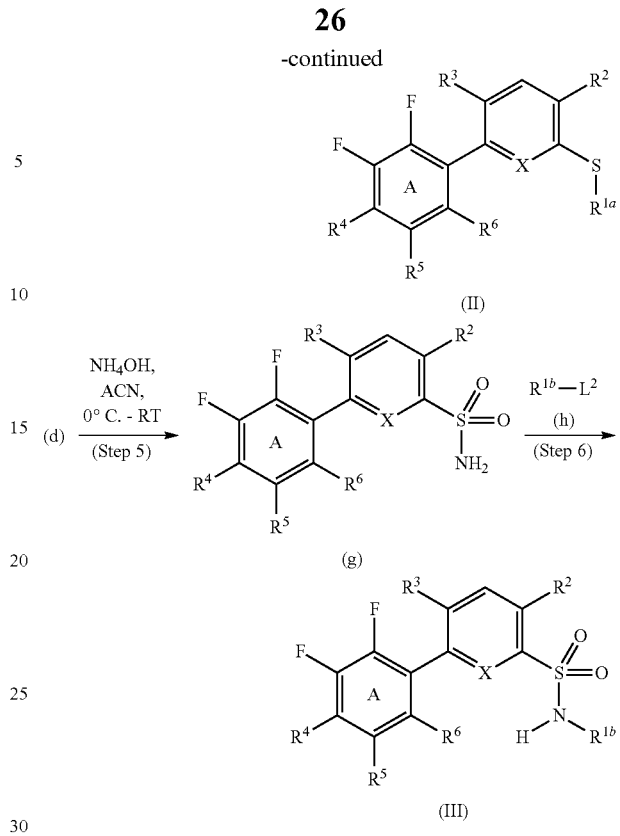

Accordingly, as shown in Step 1 of Scheme 1, compounds of formula c, where each of $R^2$ and $R^3$ can be Cl or F, each of $R^4$, $R^5$, and $R^6$ can be H or F, and where Ring A includes at least 4 F atoms, can be prepared by reaction of a boronate (e.g., a pinacol boronate) or boronic acid of formula (a) with a substituted phenyl of formula (b), where Hal is Br or I, using cross-coupling reaction conditions with the aid of a metal catalyst. Suitable catalysts include palladium catalysts, such as Pd(OAc)2 or [1,1'-Bis(diphenylphosphino)ferrocene]-dichloropalladium(II). Similar Suzuki-Miyarua reaction conditions are known to those skilled in the art. The compound of formula (c) can be transformed to a sulfonyl chloride of formula (d) via a sulfonation reaction using sulfurochloridic acid with heating, as shown in Step 2. The sulfonyl chloride of formula (d) can be converted to a thiol of formula (e) by reduction, e.g., using $SnCl_2$ as a reducing agent, as shown in Step 3. Other reducing agents such as triphenylphosphine, zinc/dichlorodimethylsilane can also be employed. Subsequently, as shown in Step 4, reaction of a thiol of formula (e) with an alkylating agent of formula (f), where $R^{1a}$ is as defined elsewhere herein but is not H, and $L^1$ is a leaving group such as a halide or sulfonate, produces a compound of formula (II), where $R^{1a}$ is as defined elsewhere herein.

Alternatively, reaction of a sulfonyl chloride of formula (d) with an ammonia source, such as ammonium hydroxide, produces a compound of formula (g), as shown in Step 5. As shown in step 6, subsequent reaction of a compound of formula (g) with an alkylating, sulfonating, or acylating reagent of formula (h), where $R^{1b}$ is as defined elsewhere herein but is not H and where $L^2$ is a halogen or an active ester leaving group, produces a compound of formula (I), where $R^1$ is $-S(O)_2NHR^{1b}$, wherein $R^{1b}$ is as defined elsewhere herein.

Alternatively, as shown in Step 6, a sulfonyl chloride of formula (e) can be converted to a thiol of formula (i) by reduction, e.g., using SnCl$_2$ as a reducing agent. Other reducing agents such as triphenylphosphine, zinc/dichlorodimethylsilane can also be employed. Subsequently, as shown in Step 7, reaction of a thiol of formula (i) with an alkylating agent of formula (j), where R$^{1a}$ is as defined elsewhere herein but is not H, and L$^2$ is a leaving group such as a halide or sulfonate, produces a compound of formula (II), where R$^{1a}$ is as defined elsewhere herein.

In another general example, compounds of formulas (II) & (III) can also be prepared as shown in Scheme 2.

is either Na$^+$ or K$^+$, under conditions favorable for decarboxylative aryl-aryl couplings. Examples of copper-mediated couplings are known to those skilled in the art and usually require a ligand such as 1,10-phenanthroline.

Another option for the preparation of a compound of formula (c), as shown in Step 3, involves the reaction of a compound of formula (c) with a boronic acid or boronate of formula (m) using Suzuki-Miyaura conditions known to those skilled in the art. The compound of formula (c) can

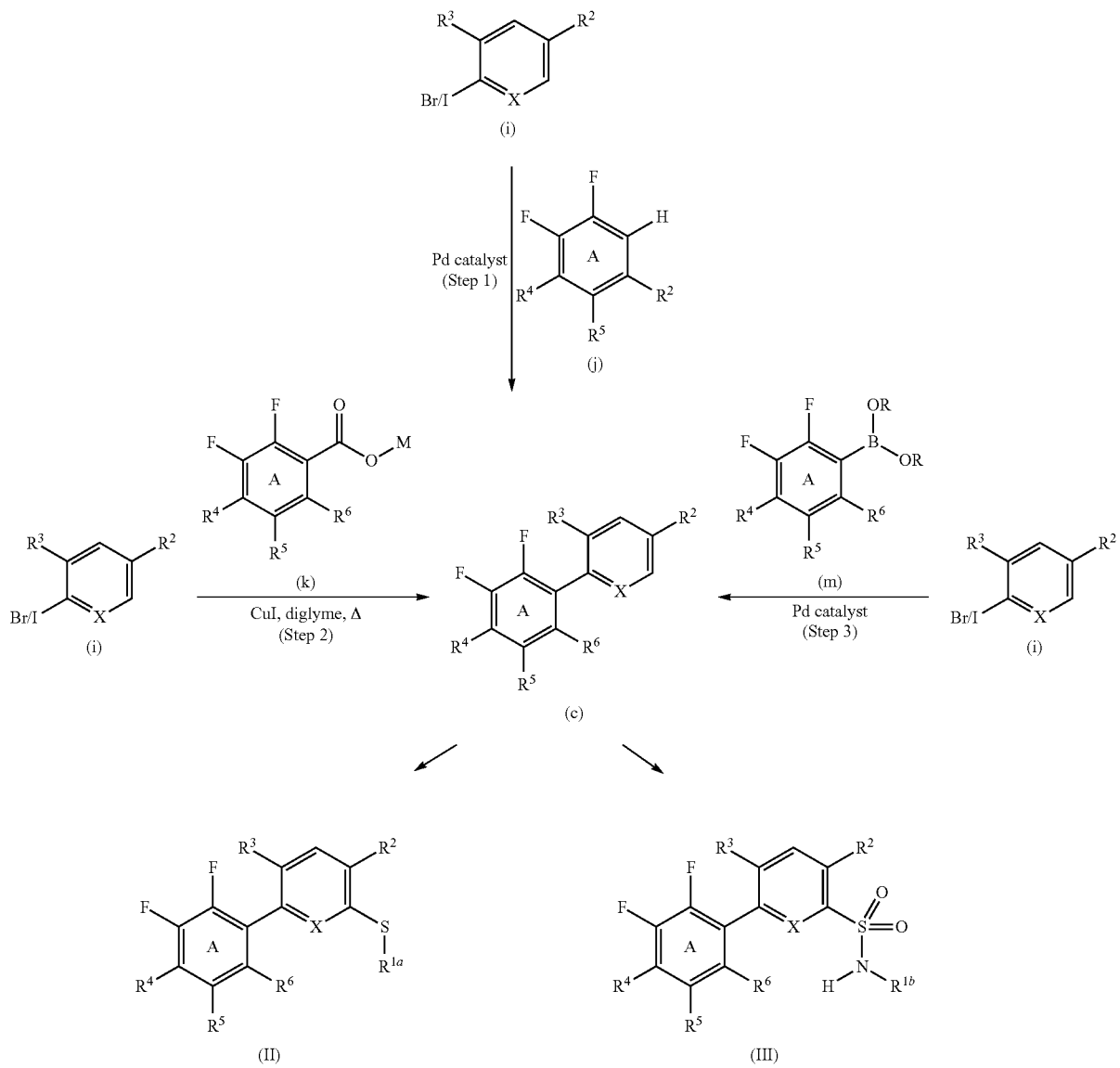

Accordingly, as shown in Step 1 of Scheme 2, a compound of formula (i) can be reacted with a fluorobenzene compound of formula (j), where Ring A includes at least 4 fluorine atoms. Such aryl-aryl couplings are known to those skilled in the art and require the use of a metal catalyst, such as Pd(OAc)$_2$.

Alternatively, as shown in Step 2, a compound of formula (i) can be reacted with a compound of formula (k), where M then be transformed into a compounds of formulas (II) or (III) as described above in Scheme 1.

In one aspect, provided is a method of preparing a compound of formula (II) as described herein, or a salt thereof, comprising:
  reacting a boronate (e.g., a pinacol boronate) or boronic acid of formula (a) with a substituted phenyl of formula (b), where Hal is Br or I, to produce a fluorinated compound of formula (c),

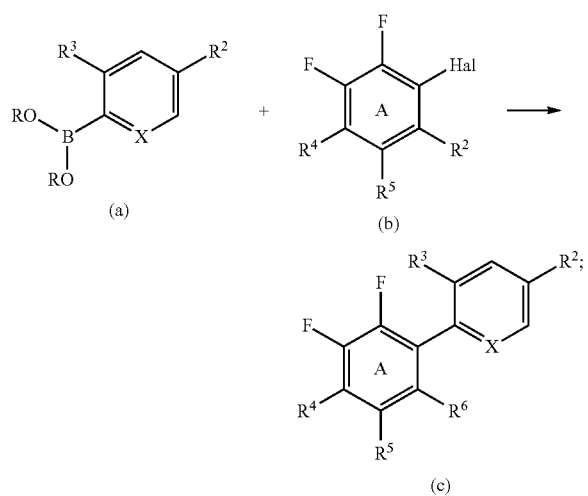

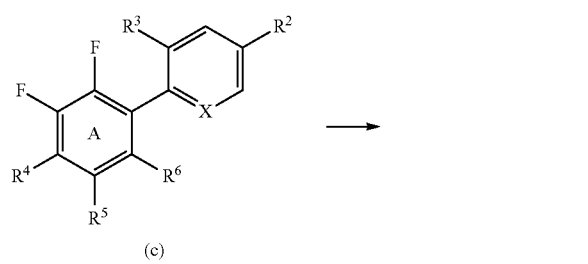

reacting a halogenated compound of formula (c) with chlorosulfonic acid to produce a sulfonyl chloride of formula (d),

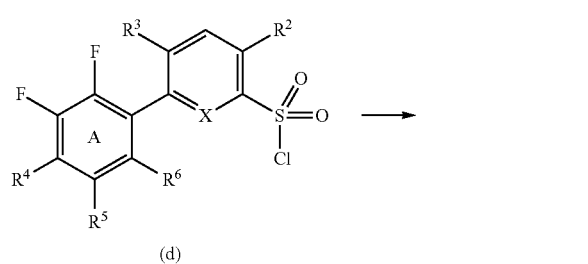

reducing a sulfonyl chloride of formula (d) to a thiol of formula (e),

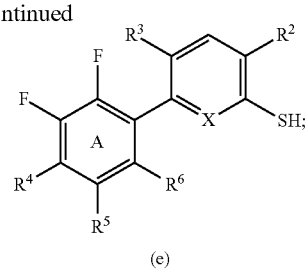

and
alkylating a thiol of formula with alkylating agent of formula $R^{1a}$-$L^1$, where $L^1$ is a leaving group and $R^{1a}$ is as defined elsewhere herein, to form a compound of formula (II),

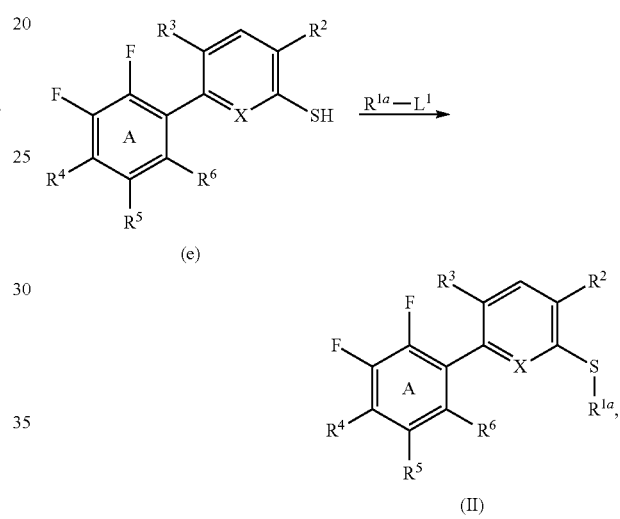

wherein X, $R^{1a}$, $R^2$, $R^3$, $R^4$, $R^5$, and $R^6$ are as described elsewhere herein.

In one embodiment, a compound of formula (c) can be formed by reacting a phenyl bromide or iodide of formula (i) with a fluorinated benzene of formula (j),

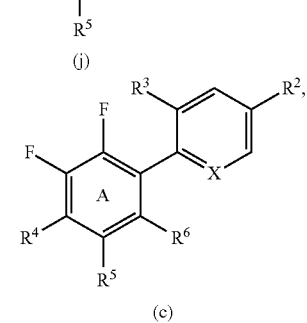

wherein $R^2$, $R^3$, $R^4$, $R^5$, and $R^6$ are as described elsewhere herein; or when X is N, $R^2$ may be $NH_2$.

In another embodiment, a compound of formula (c) can be formed by reacting a phenyl bromide or iodide of formula (i) with a phenyl sodium or potassium carboxylate of formula (k),

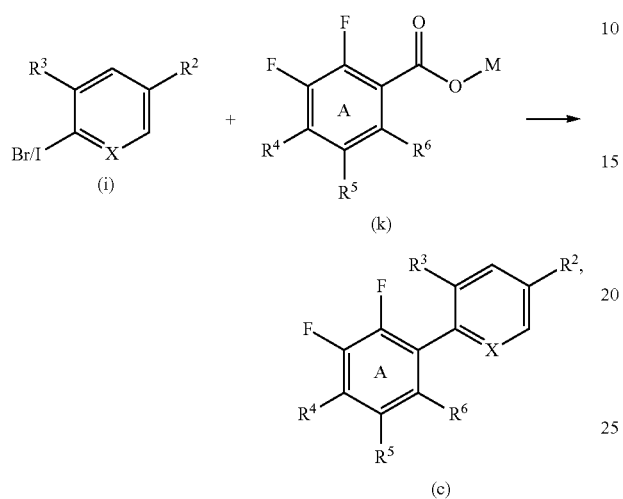

wherein X, $R^2$, $R^3$, $R^4$, $R^5$, and $R^6$ are as described elsewhere herein.

In yet another embodiment, a compound of formula (c) can be formed by reacting a phenyl bromide or iodide of formula (i) with a phenyl boronate or boronic acid of formula (m),

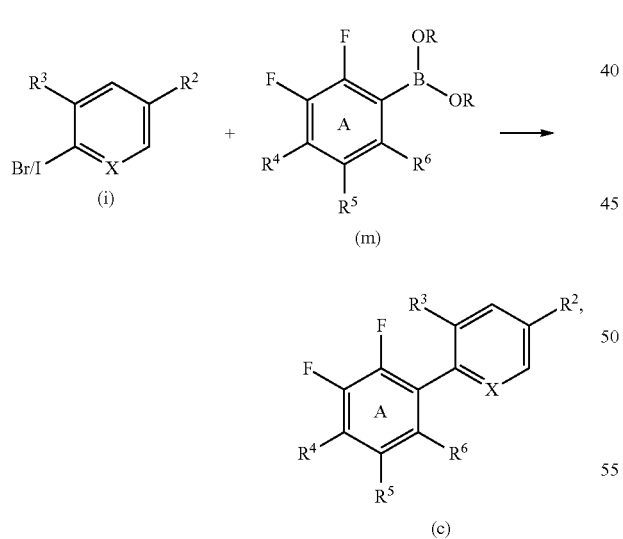

wherein $R^2$, $R^3$, $R^4$, $R^5$, and $R^6$ are as described elsewhere herein; or when X is N, $R^2$ may be $NH_2$.

In another aspect, provided is a method of preparing a compound of formula (III) as described herein, or a salt thereof, comprising:

transforming a compound of formula (a) into a sulfonyl chloride of formula (d), as described above, and react-ing the sulfonyl chloride with a source of ammonia to form a compound of formula (g),

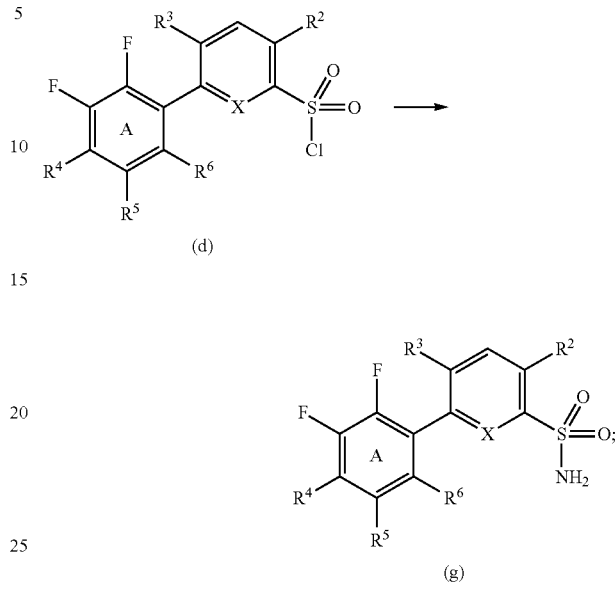

and reacting a compound of formula (g) with an alkylating, acylating, or sulfonating agent of formula $R^{1b}$-$L^2$, where $L^2$ is a halogen or an active ester leaving group and $R^{1b}$ is as described elsewhere herein, to form a compound of formula (III),

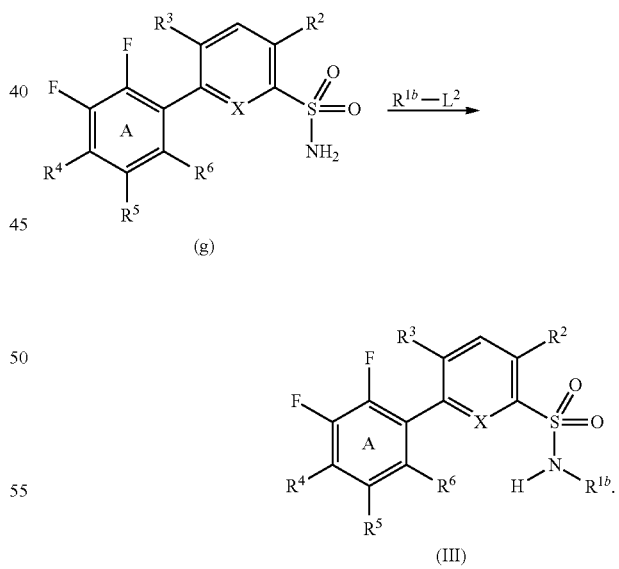

In one embodiment, $R^{1b}$ is an alkylating agent. In another embodiment, $R^{1b}$ is an acylating agent, in yet another embodiment, $R^{1b}$ is a sulfonating agent.

Any of the embodiments and variations described herein for compounds of formulas (II) or (III) also applies to intermediates of formulas (d), (e), or (g). In some aspects, provided is a compound of formula (d), (e) or (g):

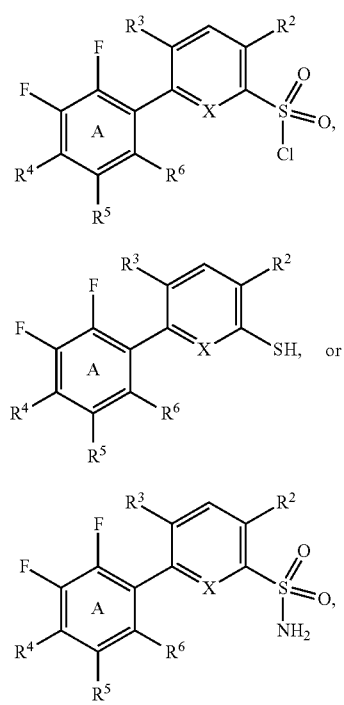

or a salt thereof (including an agriculturally suitable salt thereof).

It is recognized by one skilled in the art that various functional groups can be converted into others to provide different compounds of the invention. For a valuable resource that illustrates the interconversion of functional groups in a simple and straightforward fashion, see Larock, R. C, Comprehensive Organic Transformations: A Guide to Functional Group Preparations, $2^{nd}$ Ed., Wiley-VCH, New York, 1999.

It is also recognized that some reagents and reaction conditions described above for preparing compounds of the invention may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M., Protective Groups in Organic Synthesis, 2nd ed.; Wiley: New York, 1991). One skilled in the art will recognize that, in some cases, after the introduction of a given reagent as depicted in any individual scheme, it may be necessary to perform additional routine synthetic steps not described in detail to complete the synthesis of compounds of the invention. One skilled in the art will also recognize that it may be necessary to perform a combination of the steps illustrated in the above schemes in an order other than that implied by the particulars presented to prepare the compounds of the invention.

One skilled in the art will also recognize that compounds of the invention and the intermediates described herein can be subjected to various electrophilic, nucleophilic, radical, organometallic, oxidation, and reduction reactions to add substituents or modify existing substituents.

Compositions

In certain aspects, a compound of this disclosure, including an agriculturally suitable salt thereof, may be used as an herbicidal active ingredient in a formulation, with at least one additional component selected from the group consisting of surfactants, solid diluents, and liquid diluents, which serves as a carrier. The formulation ingredients are selected to be consistent with the physical properties of the active ingredient, mode of application, and environmental factors such as soil type, moisture, and temperature.

In some variations, the compositions provided here are herbicides. In some variations, the compositions comprise a compound of this disclosure that controls or modifies the growth of plants. In certain variations, the compositions comprise a herbicidally effective amount of the compound, such that the quantity of such compound is capable of producing a controlling or modifying effect on the growth of plants. Controlling or modifying effects include all deviation from natural development, for example killing, retardation, leaf burn, albinism, dwarfing and the like.

Liquid formulations include solutions (including emulsifiable concentrates), suspensions, emulsions (including microemulsions, oil-in-water emulsions, flowable concentrates and/or suspoemulsions), and the like, which optionally can be thickened into gels. The general types of aqueous liquid formulations are soluble concentrate, suspension concentrate, capsule suspension, concentrated emulsion, microemulsion, oil-in-water emulsion, flowable concentrate, and suspoemulsion. The general types of nonaqueous liquid formulations are emulsifiable concentrate, microemulsifiable concentrate, dispersible concentrate, and oil dispersion.

The general types of solid formulations are dusts, powders, granules, pellets, prills, pastilles, tablets, filled films (including seed coatings), and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation. Alternatively, the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength formulations are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant.

Liquid and dry formulations can be metered directly into drip irrigation systems or metered into the furrow during planting.

The formulations will typically contain effective amounts of active ingredient, diluent, and surfactant within the following approximate ranges, shown in Table 2, which add up to 100 percent by weight.

TABLE 2

Formulation Ratios

| | Weight Percent | | |
|---|---|---|---|
| | Active Ingredient | Diluent | Surfactant |
| Water-Dispersible and Water-Soluble Granules, Tablets, and Powders | 0.001-90 | 0-99.999 | 0-15 |
| Oil Dispersions, Suspensions, Emulsions Solutions (including emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Formulations | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, New Jersey.

Liquid diluents include, for example, water: N,N-dimethylalkanamides (e.g., N,N-dimethylformamide); limonene; dimethyl sulfoxide; N-alkylpyrrolidones (e.g., N-methylpyrrolidinone); alkyl phosphates (e.g., triethyl phosphate); ethylene glycol; triethylene glycol; propylene glycol; dipropylene glycol; polypropylene glycol; propylene carbonate; butylene carbonate; paraffins (e.g., white mineral oils, normal paraffins, isoparaffins); alkylbenzenes; alkylnaphthalenes; glycerine; glycerol triacetate; sorbitol; aromatic hydrocarbons; dearomatized aliphatics; alkylbenzenes; alkylnaphthalenes; ketones such as cyclohexanone, 2-heptanone, isophorone, and 4-hydroxy-4-methyl-2-pentanone; acetates such as isoamyl acetate, hexyl acetate, heptyl acetate, octyl acetate, nonyl acetate, tridecyl acetate, and isobornyl acetate; other esters such as alkylated lactate esters, dibasic esters, alkyl and aryl benzoates, and γ-butyrolactone; and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol, and benzyl alcohol. Liquid diluents also include glycerol esters of saturated and unsaturated fatty acids (typically $C_6$-$C_{22}$) such as plant seed and fruit oils (e.g., oils of olive, castor, linseed, sesame, corn (maize), peanut, sunflower, grapeseed, safflower, cottonseed, soybean, rapeseed, coconut, and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources and can be purified by distillation. Typical liquid diluents are described in C. Marsden & S. Mann. *Solvents Guide*, Cleaver-Hume Press, London, 1963.

Surfactants can be classified as nonionic, anionic, or cationic. Nonionic surfactants useful for the present formulations include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides, and ethoxylated alkanolamides; alkoxylated triglycerides such as ethoxylated soybean, castor, and rapeseed oils; alkylphenol alkoxylates such as octylphenol ethoxylates, nonylphenol ethoxylates, dinonyl phenol ethoxylates, and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters: ethoxylated tristyrylphenol (including those prepared from ethylene oxide, propylene oxide, butylene oxide, or mixtures thereof); fatty acid esters, glycerol esters, lanolin-based derivatives, polyethoxylate esters such as polyethoxylated sorbitan fatty acid esters, polyethoxylated sorbitol fatty acid esters, and polyethoxylated glycerol fatty acid esters; other sorbitan derivatives such as sorbitan esters; polymeric surfactants such as random copolymers, block copolymers, alkyd PEG (polyethylene glycol) resins, graft or comb polymers and star polymers; polyethylene glycols (PEGs); polyethylene glycol fatty acid esters; silicone-based surfactants; and sugar-derivatives such as sucrose esters, alkyl polyglycosides, and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides: amines such as N-alkyl propanediamines, tripropylenetriamines, and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts, and diquaternary salts; and amine oxides such as alkyldimethylamine oxides and bis-(2-hydroxyethyl)-alkylamine oxides.

Also useful for the present formulations are mixtures of nonionic and anionic surfactants or mixtures of nonionic and cationic surfactants. Nonionic, anionic, and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Formulations of the present invention may also contain formulation auxiliaries and additives, known to those skilled in the art as formulation aids (some of which may be considered to also function as solid diluents, liquid diluents, or surfactants). Such formulation auxiliaries and additives may control the following: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers, and waxes. Examples of formulation auxiliaries and additives include those listed in *McCutcheon's Volume 2: Functional Materials*, annual International and North American editions published by McCutcheon's Division. The Manufacturing Confectioner Publishing Co.: and PCT Publication WO 03/024222.

The compounds of the invention and any other active ingredients are typically incorporated into the present formulations by dissolving the active ingredient in a solvent or by grinding in a liquid or dry diluent. Solutions, including emulsifiable concentrates, can be prepared by simply mixing the ingredients. If the solvent of a liquid formulations intended for use as an emulsifiable concentrate is water-immiscible, an emulsifier is typically added to emulsify the active-containing solvent upon dilution with water. Active ingredient slurries, with particle diameters of up to 2,000 microns can be wet milled using media mills to obtain particles with average diameters below 3 microns. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 micron to 10 micron range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration," *Chemical Engineering*, Dec. 4, 1967, pp 147-48, *Perry's Chemical Engineer's Handbook*, 4th Ed., McGraw-Hill, New York, 1963, pages 8-57 and following, and PCT Publication WO 91/13546. Pellets can be prepared as described in U.S. Pat. No. 4,172,714. Water-dispersible and water-soluble granules can be prepared as taught in U.S. Pat. Nos. 4,144,050 and 3,920,442 and German Pat. No. 3,246,493. Tablets can be prepared as taught in U.S. Pat. Nos. 5,180,587, 5,232,701, and 5,208,030. Films can be prepared as taught in Great Britain Pat. No. 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

Biological Activity

Test results indicate that the compounds of the present invention are highly active preemergent and/or postemergent herbicides and/or plant growth regulants. The compounds of the invention generally show highest activity for postemergence weed control (e.g., applied after weed seedlings emerge from the soil) and preemergence weed control (e.g., applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, airfields, riverbanks, irrigation, and other waterways, around billboards and highway and railroad structures. Many of the compounds of this disclosure, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays.

In some variations, provided herein is a method of controlling undesired vegetation, comprising applying a compound of formula (H), (H), or (III), or a salt thereof (including an agriculturally suitable salt thereof). In some variations, the compound is applied at low application rates. In certain variations, the compound is applied at a rate of 1 to 10,000 g per 10,000 $m^2$, 2 to 5,000 g per 10,000 $m^2$, 5 to 2,000 g per 10,000 $m^2$, 1 to 1000 g per 10,000 $m^2$, 1 to 500 g per 10,000 $m^2$, 1 to 100 g per 10,000 $m^2$, 1 to 75 g per 10,000 $m^2$, 15 to 1000 g per 10,000 $m^2$, 15 to 100 g per 10,000 $m^2$, 15 to 75 g per 10,000 $m^2$, or 15 to 60 g per 10,000 $m^2$. In certain variations of the foregoing, the application of the compound at the aforementioned application rates leads to postemergence control of the undesired vegetation and/or preemergence control of the undesired vegetation.

In certain variations, the application of the compound, including at the aforementioned application rate, leads to burndown. In one variation, burndown refers to when an herbicide is used to reduce weed presence at the time of treatment. Burndown is often used in minimum or no-till fields because the weeds cannot be managed by tilling the soil. The burndown application may be used post-harvest and/or prior to crop emergence. Burndown may be useful against weeds that emerge between growing seasons.

In certain variations, the application of the compound, including at the aforementioned application rate, imparts residual control. The compounds described herein may be used as pre-emergence herbicides, which may be applied after crop planting, but prior to crop and/or weed emergence. Herbicides considered pre-emergence also may be referred to as those imparting "residual control," and provide extended control of germinating or newly emerged weeds.

In one variation, the undesired vegetation is at least 50%, at least 55%, at least 60%, at least 65%, at least 70%, at least 75%, at least 80%, at least 85%, at least 90%, at least 95%, at least 96%, at least 97%, at least 98%, at least 99%, or about 100% controlled. In some variations of the foregoing, the undesired vegetation is a weed. In one variation, the undesired vegetation is a PPO inhibitor-resistant weed.

Examples of crop fields treated by the compounds in the present invention include edible crop fields such as peanut fields, soybean fields, corn fields, and wheat fields, feed crop fields such as *Sorghum* fields and oat fields, industrial crop fields such as cotton fields and rape fields, and sugar crop fields such as sugarcane fields and sugar beet fields. In one variation, crop fields treated by the compounds herein include corn, soybean, wheat, and cotton fields.

Examples of vegetable fields treated by the compounds in the present invention include fields for cultivation of solanaceous vegetables (eggplants, tomatoes, bell peppers, capsicums, potatoes, and the like), fields for cultivation of cucurbitaceous vegetables (cucumbers, pumpkins, zucchini, watermelons, melons, and the like), fields for cultivation of cruciferous vegetables (radishes, turnips, horseradishes, kohlrabies, Chinese cabbages, cabbages, mustard, broccolis, cauliflowers, and the like), fields for cultivation of asteraceous vegetables (burdocks, garland chrysanthemums, artichokes, lettuces, and the like), fields for cultivation of liliaceous vegetables (leeks, onions, garlics, and asparagus), fields for cultivation of apiaceous vegetables (carrots, parsley, celery, parsnips, and the like), fields for cultivation of chenopodiaceous vegetables (spinach, chards, and the like), fields for cultivation of lamiaceous vegetables (perilla, mint, basil, and lavender), strawberry fields, sweet potato fields, yam fields, and taro fields.

Examples of the land under perennial crops in the present invention include orchards, tea fields, mulberry fields, coffee fields, banana fields, palm fields, flowering tree firms, flowering tree fields, planting stock fields, nursery fields, forest lands, and gardens. Examples of the orchard trees in the present invention include pomaceous fruits (apples, pears, Japanese pears, Chinese quinces, quinces, and the like), stone fruits (peaches, plums, nectarines, Japanese apricots, cherries, apricots, prunes, and the like), citrus fruits (Citrus unshiu, oranges, lemons, limes, grapefruits, and the like), nut trees (chestnuts, walnuts, hazelnut trees, almonds, pistachios, cashew nut trees, macadamia nut trees, and the like), berry fruits (grapes, blueberries, cranberries, blackberries, raspberries, and the like), Japanese persimmons, olives, and loquats.

Examples of the non-crop land in the present invention include athletic fields, empty lots, railroad edges, parks, parking lots, road edges, dry riverbeds, lands under a power line, residential lands, and factory sites.

The crop cultivated in the crop field in the present invention is not limited as long as the crop is a variety generally cultivated as a crop.

The plant of the above-mentioned variety may be a plant that can be produced by natural crossing, a plant that can be generated by mutation, an F1 hybrid plant, or a transgenic plant (also referred to as a genetically-modified plant). The plant generally has properties such as obtaining of the tolerance to an herbicide, accumulation of a toxic substance against a pest, suppression of the susceptibility to a disease, increase in the yield potential, improvement in the tolerance to a biotic and an abiotic stressors, accumulation of a substance, and improvement in the preservability and the processability.

An F1 hybrid plant is a first-generation hybrid obtained by crossing varieties of two different strains, and generally has a heterotic property with a trait superior to that of either of the parents. A transgenic plant has a foreign gene introduced from another organism or the like such as a microorganism and has a property that cannot be easily obtained by cross breeding, mutagenesis, or natural recombination in a natural environment.

Examples of the techniques for producing the above-mentioned plants include conventional breeding techniques; genetic engineering techniques; genome breeding techniques; new breeding techniques; and genome editing techniques. Conventional breeding techniques are for obtaining a plant having a desirable property by mutation or crossing. Genetic engineering techniques include techniques for imparting a new property to a target organism by extracting a target gene (DNA) from another organism (for example, a microorganism) and introducing the target gene into the genome of the target organism. Genetic engineering techniques also include antisense techniques or RNA interference techniques for imparting a new or improved property by silencing another gene present in the plant. Genome breeding techniques are for improving breeding efficiency using genomic information, and examples of the genome breeding techniques include DNA marker (also called genomic marker or genetic marker) breeding techniques and genomic selection. For example, DNA marker breeding is a method in which a progeny having a target useful trait gene is selected from a large number of crossed progenies using a DNA marker that is a DNA sequence that serves as a marker of the location of the specific useful trait gene on the genome. In the method, the crossed progeny is analyzed when it is an infant plant using a DNA marker to effectively shorten the time required for the breeding.

Genomic selection is a technique in which a prediction formula is created from a phenotype and genomic information obtained in advance to predict the property from the prediction formula and the genomic information without evaluating the phenotype and is a technique that can contribute to improving breeding efficiency. The term "new breeding techniques" is a general term for breed improvement (breeding) techniques that combine molecular biological techniques. Examples of the new breeding techniques include cisgenesis/intragenesis, oligonucleotide-directed mutagenesis, RNA-dependent DNA methylation, genome editing, grafting on a GM rootstock or a scion, reverse breeding, agroinfiltration, and seed production technology (SPT). The genome editing technique is for converting genetic information in a sequence-specific manner, and it is possible to delete a base sequence, substitute an amino acid sequence, introduce a foreign gene, and the like using the technique. Examples of the tool include sequence-specific genome modification techniques such as a zinc finger nuclease capable of sequence-specific DNA cleavage (Zinc-Finger. ZFN), TALEN, CRISPR-Cas9, CRISPER-Cpf1, Meganuclease, and CAS9 Nickase and Target-AID created by modifying the aforementioned tools.

Examples of the above-mentioned plants include plants listed in the database of the registered genetically-modified crops (GM Approval Database) in the electronic information site of International Service for the Acquisition of Agri-biotech Applications (ISAAA) (www.isaaa.org). More specific examples are herbicide-tolerant plants, pest-resistant plants, disease-resistant plants, plants modified in the quality (for example, with increase or decrease in the content or change in the composition) of the products (for example, starch, amino acids, and fatty acids), fertility trait-modified plants, abiotic stress-tolerant plants, and plants modified in the trait related to the growth or the yield.

Mechanisms of obtaining herbicide tolerance include reduction in the affinity between the agent and its target, rapid metabolism (decomposition, modification, and the like) of the agent by an expressed enzyme that inactivates the agent, or inhibition of incorporation or translocation of the agent in the plant body. Examples of the plants to which herbicide tolerance has been imparted by genetic engineering technique include plants to which tolerance has been imparted to 4-hydroxyphenylpyruvate dioxygenase (hereinafter abbreviated as HPPD) inhibitors such as isoxaflutole and mesotrione, acetolactate synthase (hereinafter abbreviated as ALS) inhibitors such as imidazolinone herbicides containing imazethapyr and sulfonylurea herbicides containing thifensulfuron-methyl, 5-enolpyruvylshikimate-3-phosphate synthase (hereinafter abbreviated as EPSP) inhibitors such as glyphosate, glutamine synthase inhibitors such as glufosinate, auxin herbicides such as 2,4-D and dicamba, and oxynyl herbicides containing bromoxynil. Preferable herbicide-tolerant transgenic plants treated by the combinations of the invention are cereals such as wheat, barley, rye, and oats, canola, Sorghum, soybeans, rice, rape, sugar beet, sugar cane, grapes, lentils, sunflowers, alfalfa, pomaceous fruits, drupes, coffee, tea, strawberries, lawn grass, tomatoes, potatoes, cucumbers, and vegetables such as lettuces, and more preferable herbicide-tolerant transgenic plants are cereals such as wheat, barley, rye, and oats, soybeans, rice, vines, tomatoes, potatoes, and pomaceous fruits.

In one example, in order to obtain the glyphosate herbicide-tolerant plants one or more genes are introduced from: a glyphosate-tolerant EPSPS gene (CP4 epsps) from *Agrobacterium tumefaciens* strain CP4; a glyphosate metabolizing enzyme gene (gat4601, gat4621) in which the metabolic activity of the glyphosate metabolizing enzyme (glyphosate N-acetyltransferase) gene from *Bacillus licheniformis* is enhanced by a shuffling technique; a glyphosate metabolizing enzyme (glyphosate oxidase gene, goxv247) from *Ochrobacterum anthropi* strain LBAA; and EPSPS genes from maize having a glyphosate-tolerant mutation (mepsps, 2mepsps). Main examples of the plants are alfalfa (*Medicago sativa*), Argentine canola (*Brassica napus*), cotton (*Gossypium hirsutum* L.), creeping bentgrass (*Agrostis stolonifera*), maize (*Zea mays* L.), polish canola (*Brassica rapa*), potato (*Solanum tuberosum* L.), soybean (*Glycine max* L.), sugar beet (*Beta vulgaris*), and wheat (*Triticum aestivum*). Some glyphosate-tolerant transgenic plants are commercially available. For example, the genetically-modified plant in which the glyphosate-tolerant EPSPS from the *Agrobacterium* is expressed is commercially available with a trade name such as "Roundup Ready®" the genetically-modified plant in which the glyphosate metabolizing enzyme that is from *Bacillus* and has the metabolic activity enhanced by a shuffling technique is expressed is commercially available with a trade name such as "Optimum® GAT®, or "Optimum® Gly canola", and the genetically-modified plant in which the EPSPS that is from maize and has glyphosate-tolerant mutation is expressed is commercially available with the trade name "GlyTol®".

In another example, in order to obtain the glufosinate herbicide-tolerant plants one or more genes are introduced from: a phosphinothricin N-acetyltransferase (PAT) gene (bar) that is a glufosinate metabolizing enzyme from *Streptomyces hygroscopicus*; a phosphinothricin N-acetyltransferase (PAT) enzyme gene (pat) that is a glufosinate metabolizing enzyme from *Streptomyces viridochromogenes*; and a synthesized pat gene (pat syn) from *Streptomyces viridochromogenes* strain Tu494. Main examples of the plants include Argentine canola (*Brassica napus*), chicory (*Cichorium intybus*), cotton (*Gossypium hirsutum* L.), maize (*Zea mays* L.), polish canola (*Brassica rapa*), rice (*Oryza sativa* L.), soybean (*Glycine max* L.), and sugar beet (*Beta vulgaris*). Some glufosinate-tolerant genetically-modified plants are commercially available. For example, a genetically-modified plant from a glufosinate metabolizing enzyme (bar) from *Streptomyces hygroscopicus* and from *Streptomyces viridochromogenes* is commercially available with trade names such as "LibertyLink®", "InVigor®", or "WideStrike®".

In another example, oxynil herbicide-tolerant plants are known. For example, bromoxynil-tolerant transgenic plants into which a nitrilase gene (bxn) is introduced from an oxynil herbicide metabolizing enzyme from *Klebsiella pneumoniae* subsp. *ozaenae*. Main examples of the plants are Argentine canola (*Brassica napus*), cotton (*Gossypium hirsutum* L.), and tobacco (*Nicotiana tabacum* L.). The plants are commercially available with a trade name such as "Navigator® canola" or "BXN®".

ALS herbicide-tolerant plants are also known. Examples include carnations (*Dianthus caryophyllus*), which are obtained by introduction of an ALS herbicide-tolerant ALS gene (surB) as a selection marker from tobacco (*Nicotiana tabacum*) and are commercially available with the trade names "Moondust®", "Moonshadow®", "Moonshade®", "Moonlite®", "Moonaqua®", "Moonvista®", "Moonique®", "Moonpearl®", "Moonberry®", and "Moonvelvet®"; flax (*Linum usitatissumum* L.), into which an ALS herbicide-tolerant ALS gene (als) from *Arabidopsis thaliana* is introduced is commercially available with the trade name "CDC Triffid Flax"; sulfonylurea herbicide-tolerant and an imidazolinone herbicide-tolerant maize (*Zea mays* L.) into which an ALS herbicide-tolerant ALS gene (zm-hra) from maize is introduced is commercially available with the trade name "Optimum® GAT™"; an imidazolinone herbicide-tolerant soybean into which an ALS herbicide-tolerant ALS gene (csrl-2) from *Arabidopsis thaliana* is introduced is commercially available with the trade name "Cultivance®"; and sulfonylurea herbicide-tolerant soybeans into which an ALS herbicide-tolerant ALS gene (gm-hra) from a soybean (*Glycine max*) is introduced are commercially available with the trade names "Treus®", "Plenish®", and "Optimum® GAT™". There is also cotton into which an ALS herbicide-tolerant ALS gene (S4-HrA) from tobacco (*Nicotiana tabacum* cv. *Xanthi*) is introduced.

HPPD herbicide-tolerant plants are also known. In one example, a soybean into which a mesotrione-tolerant HPPD gene (avhppd-03) from an oat (*Avena sativa*) and a phinothricin N-acetyltransferase (PAT) enzyme gene (pat) are simultaneously introduced. In another example, a soybean tolerant to mesotrione into which a glufosinate metabolizing enzyme from *Streptomyces viridochromogenes* is introduced is commercially available.

In another example, 2,4-D-tolerant plants include: maize into which an aryloxyalkanoate dioxygenase gene (aad-1) for a 2,4-D metabolizing enzyme from *Sphingobium herbicidovorans* is introduced is commercially available with the trade name "Enlist® Maize"; and soybean and cotton into which an aryloxyalkanoate dioxygenase gene (aad-12) for a 2,4-D metabolizing enzyme from *Delftia acidovorans* is introduced is commercially available with the trade name "Enlist® Soybean".

In another example, Dicamba-tolerant plants include: soybean and cotton into which a dicamba monooxygenase gene (dmo) having a dicamba metabolizing enzyme from *Stenotrophomonas maltophilia* strain DI-6 is introduced; and a soybean (*Glycine max* L.) into which a glyphosate-tolerant EPSPS gene (CP4 epsps) from *Agrobacterium tumefaciens* strain CP4 is introduced simultaneously with the above-mentioned gene is commercially available with the trade name "Genuity® Roundup Ready™ 2 Xtend®".

Further examples of the commercially available transgenic plants to which herbicide tolerance has been imparted include: the glyphosate-tolerant maize "Roundup Ready® Corn", "Roundup Ready® 2", "Agrisure® GT", "Agrisure® GT/CB/LL", "Agrisure® GT/RW", "Agrisure® 3000GT", "YieldGard™ VT™ Rootworm/RR2", and "YieldGard™ VT™ Triple"; the glyphosate-tolerant soybeans "Roundup Ready® Soybean" and "Optimum® GAT": the glyphosate-tolerant cotton "Roundup Ready® Cotton" and "Roundup Ready® Flex"; the glyphosate-tolerant canola "Roundup Ready® Canola"; the glyphosate-tolerant alfalfa "Roundup Ready® Alfalfa", the glyphosate-tolerant rice "Roundup Ready® Rice"; the glufosinate-tolerant maize "Roundup Ready® 2", "LibertyLink®", "Herculex® 1", "Herculex® RW", "Herculex® Xtra", "Agrisure® GT/CB/LL", "Agrisure® CB/LL/RW", and "Bt10"; the glufosinate-tolerant cotton "FiberMax™ LibertyLink™"; the glufosinate-tolerant canola "InVigor®"; the glufosinate-tolerant rice "LibertyLink™ Rice" (manufactured by Bayer AG); the bromoxynil-tolerant cotton "BXN"; the bromoxynil-tolerant canola "Navigator®" and "Compass®"; and the glufosinate-tolerant canola "InVigor®". Additional plants modified with respect to a herbicide are widely known, and the examples of the plants include alfalfa, apples, barley, eucalyptuses, flax, grapes, lentils, rape, peas, potatoes, rice, sugar beet, sunflowers, tobacco, tomato, turfgrass, and wheat that are tolerant to glyphosate (see, for example, U.S. Pat. Nos. 5,188,642, 4,940,835, 5,633,435, 5,804,425, and 5,627,061); beans, cotton, soybeans, peas, potatoes, sunflowers, tomatoes, tobacco, maize, *Sorghum*, and sugar cane that are tolerant to dicamba (see, for example, WO2008051633, U.S. Pat. Nos. 7,105,724, and 5,670,454); soybeans, sugar beet, potatoes, tomatoes, and tobacco that are tolerant to glufosinate (see, for example, U.S. Pat. Nos. 6,376,754, 5,646,024, and 5,561,236); cotton, peppers, apples, tomatoes, sunflowers, tobacco, potatoes, maize, cucumbers, wheat, soybeans, *Sorghum*, and cereals that are tolerant to 2,4-D (see, for example, U.S. Pat. Nos. 6,153,401, 6,100,446, WO2005107437, U.S. Pat. Nos. 5,608,147, and 5,670,454); and canola, maize, millet, barley, cotton, mustard, lettuces, lentils, melons, millet, oats, sword beans, potatoes, rice, rye, *Sorghum*, soybeans, sugar beet, sunflowers, tobacco, tomatoes, and wheat that are tolerant to acetolactate synthase (ALS) inhibitor herbicide (for example, a sulfonylurea herbicide and an imidazolinone herbicide) (see, for example, U.S. Pat. No. 5,013,659, WO2006060634, U.S. Pat. Nos. 4,761,373, 5,304,732, 6,211,438, 6,211,439, and 6,222,100). The rice tolerant to an imidazolinone herbicide is especially known, and examples of the rice include rice having specific mutation (for example, S653N, S654K, A122T, S653(At)N, S654(At)K, and A122(At)T) in the acetolactate synthase gene (acetohydroxyacid synthase gene) (see, for example, US 2003/0217381, and WO200520673); and the examples include barley, sugar cane, rice, maize, tobacco, soybeans, cotton, rape, sugar beet, wheat, and potatoes that are tolerant to an HPPD inhibitor herbicide (for example, an isoxazole herbicide such as isoxaflutole, a triketone herbicide such as sulcotrione or mesotrione, a pyrazole herbicide such as pyrazolynate, or diketonitrile that is a decomposition product of isoxaflutole) (see, for example, WO2004/055191, WO199638567. WO1997049816, and U.S. Pat. No. 6,791,014).

Examples of the plants to which herbicide tolerance has been imparted by a classical technique or a genome breeding technique include the rice "Clearfield® Rice", the wheat "Clearfield® Wheat", the sunflower "Clearfield® Sunflower", the lentil "Clearfield® lentils", and the canola "Clearfield® canola" (manufactured by BASF SE) that are tolerant to an imidazolinone-based ALS inhibitor herbicide such as imazethapyr or imazamox; the soybean "STS® soybean" that is tolerant to a sulfonyl-based ALS inhibitor herbicide such as thifensulfuron-methyl; the sethoxydim-tolerant maize "SR® corn" and 'Poast Protected® corn" that are tolerant to an acetyl-CoA carboxylase inhibitor such as a trionoxime herbicide or an aryloxy phenoxypropionic acid herbicide; the sunflower "ExpressSun®" that is tolerant to a sulfonylurea herbicide such as tribenuron; the rice "Provisia™ Rice" that is tolerant to an acetyl-CoA carboxylase inhibitor such as quizalofop; and the canola "Triazine Tolerant Canola" that is tolerant to a PSII inhibitor.

Examples of the plants to which herbicide tolerance has been imparted by a genome editing technique include the canola "SU Canola®" tolerant to a sulfonylurea herbicide in which a rapid variety development technique (Rapid Trait Development System, RTDS®) is used. RTDS® corresponds to oligonucleotide-directed mutagenesis of the genome editing technique, and by RTDS, it is possible to introduce mutation in a DNA in a plant via Gene Repair Oligonucleotide (GRON), that is, a chimeric oligonucleotide of the DNA and the RNA without cutting the DNA. In addition, examples of the plants include maize in which herbicide tolerance and phytic acid content have been reduced by deleting the endogenous gene IPK1 using zinc finger nuclease (see, for example, Nature 459, 437-441 2009); and rice to which herbicide tolerance has been imparted using CRISPR-Cas9 (see, for example, Rice, 7, 5 2014).

In the present invention, examples of the crop tolerant to a specific PPO inhibitor include crops to which PPO having a reduced affinity for the inhibitor is imparted by a genetic engineering technique. Alternatively, the crop may have a substance that detoxifies and decomposes the PPO inhibitor by cytochrome P450 monooxygenase alone or in combination with the above-mentioned PPO. The tolerant crops are described in, for example, patent documents such as WO2011085221. WO2012080975. WO2014030090, WO2015022640, WO2015022636. WO2015022639, WO2015092706, WO2016203377, WO2017198859, WO2018019860, WO2018022777, WO2017112589, WO2017087672, WO2017039969, and WO2017023778, and non-patent document Li & Nicholl in Pest Management Science (2005), Vol. 61, pgs. 277-285.

Examples of the plants to which herbicide tolerance has been imparted by a new breeding technique in which the property of a GM rootstock is imparted to a scion by a breeding technique in which grafting is used include the non-transgenic soybean scion to which glyphosate tolerance is imparted using the glyphosate-tolerant soybean Roundup Ready® as a rootstock (see Jiang, et al., in Weed Technology (2013) Vol. 27, pgs. 412-416).

The above-mentioned plants include strains to which two or more traits are imparted among abiotic stress tolerance, disease resistance, herbicide tolerance, pest resistance, a growth trait, a yield trait, nutrient uptake, product quality, a fertility trait, and the like as described above using a genetic engineering technique, a classical breeding technique, a genome breeding technique, a new breeding technique, a genome editing technique, or the like, and strains to which two or more of the properties of the parent strains are imparted by crossing plants having the same or different properties.

Examples of the commercially available plants to which tolerance to two or more herbicides are imparted include the cotton "GlyTol™ LibertyLink™" and "GlyTol™ LibertyLink™" that are tolerant to glyphosate and glufosinate; the maize "Roundup Ready™ LibertyLink™ Maize" that is tolerant to glyphosate and glufosinate; the soybean "Enlist™ Soybean" that is tolerant to glufosinate and 2,4-D; the soybean "Genuity® Roundup Ready (trademark) 2 Xtend (trademark)" that is tolerant to glyphosate and dicamba; the maize and the soybean "OptimumGAT™" that are tolerant to glyphosate and an ALS inhibitor; the genetically modified soybeans "Enlist E3™" and "Enlist™ Roundup Ready® 2 Yield" that are tolerant to three herbicides of glyphosate, glufosinate, and 2,4-D; the genetically modified maize "Enlist™ Roundup Ready® Corn 2" that is tolerant to glyphosate, 2,4-D, and an aryloxyphenoxypropionate (FOPs) herbicide; the genetically modified maize "Enlist™ Roundup Ready® Corn 2" that is tolerant to glyphosate, 2,4-D, and an aryloxyphenoxypropionate (FOPs) herbicide; the genetically modified cotton "Bollgard 11® XtendFlex™ Cotton" that is tolerant to dicamba, glyphosate, and glufosinate; and the genetically modified cotton "Enlist™ Cotton" that is tolerant to three herbicides of glyphosate, glufosinate, and 2,4-D. In addition, the cotton tolerant to glufosinate and 2,4-D, the cotton tolerant to both glufosinate and dicamba, the maize tolerant to both glyphosate and 2,4-D, the soybean tolerant to both glyphosate and an HPPD herbicide, and the genetically modified maize tolerant to glyphosate, glufosinate, 2,4-D, an aryloxyphenoxypropionate (FOPs) herbicide, and a cyclohexanedione (DIMs) herbicide have been also developed.

Examples of the commercially available plants to which herbicide tolerance and pest resistance are imparted include the maize "YieldGard Roundup Ready®" and "YieldGard Roundup Ready® 2" that are tolerant to glyphosate and resistant to a corn borer; the maize "Agrisure® CB/LL" that is tolerant to glufosinate and resistant to a corn borer; the maize "Yield Gard® VT Root worm/RR2" that is tolerant to glyphosate and resistant to a corn rootworm; the maize "Yield Gard® VT Triple" that is tolerant to glyphosate and resistant to a corn rootworm and a corn borer; the maize "Herculex® r" that is tolerant to glufosinate and resistant to a lepidopteran maize pest (Cry1F) (for example, resistance to a western bean cutworm, a corn borer, a black cutworm, and a fall armyworm); the maize "YieldGard® Corn Rootworm/Roundup Ready® 2" that is tolerant to glyphosate and resistant to a corn rootworm; the maize "Agrisure® GT/RW" that is tolerant to glufosinate and resistant to a Coleoptera maize pest (Cry3A) (for example, resistant to a western corn rootworm, a northern corn rootworm, and a Mexican corn rootworm); the maize "Herculex® RW" that is tolerant to glufosinate and resistant to a Coleoptera maize pest (Cry34/35Abl) (for example, resistant to a western corn rootworm, a northern corn rootworm, and a Mexican corn rootworm); the maize "Yield Gard® VT Root worm/RR2" that is tolerant to glyphosate and resistant to a corn rootworm; and the cotton "Bollgard 3® XtendFlex®" that is tolerant to dicamba, glyphosate, and glufosinate and resistant to a lepidopteran cotton pest (for example, resistant to bollworms, a tobacco budworm, and armyworms).

In the present invention, a composition of the invention is applied to a place where weeds are growing or likely to grow. Examples of the method of applying the present composition include a method of spraying the present composition on soil and a method of spraying the present composition on weeds.

In some variations, the application rate of a composition of the invention is generally 1 to 10,000 g per 10,000 $m^2$, 2 to 5,000 g per 10,000 $m^2$, 5 to 2,000 g per 10,000 $m^2$, 1 to 1000 g per 10,000 $m^2$, 1 to 500 g per 10,000 $m^2$, 1 to 100 g per 10,000 $m^2$, 1 to 75 g per 10,000 $m^2$, 15 to 1000 g per 10,000 $m^2$, 15 to 100 g per 10,000 $m^2$, 15 to 75 g per 10,000 $m^2$, or 15 to 60 g per 10,000 $m^2$, in terms of the total amount of a compound of formula I, II, III or IV, or a salt thereof (including an agriculturally suitable salt thereof).

In one variation, the application rate of a composition of the invention is generally 1 to 10,000 g per 10,000 $m^2$, 2 to 5,000 g per 10,000 $m^2$, 5 to 2,000 g per 10,000 $m^2$, 1 to 1000 g per 10,000 $m^2$, 1 to 500 g per 10,000 $m^2$, 1 to 100 g per 10,000 $m^2$, 1 to 75 g per 10,000 $m^2$, 15 to 1000 g per 10,000 $m^2$, 15 to 100 g per 10,000 $m^2$, 15 to 75 g per 10,000 $m^2$, or 15 to 60 g per 10,000 $m^2$, in terms of the total amount of a compound of formula I and the at least one compound selected from the group consisting of the herbicide compound group B and the safener group C.

In the present method, an adjuvant may be mixed in a composition of the invention, followed by application. The type of the adjuvant is not particularly limited, and examples of the adjuvant include oil-based adjuvants such as Agri-Dex® and methylated seed oil (MSO), non-ions (esters or ethers of polyoxyethylene) such as Induce, anions (substituted sulfonates) such as Gramine S, cations (polyoxyethylene amines) such as Genamin® T 200BM, and organic silicons such as Silwet® L77.

The pH and the hardness of the spray liquid prepared when a composition of the invention is applied are not particularly limited, and the pH is usually in the range of 5 to 9, and the hardness is usually in the range of 0 to 500.

The time period for applying a composition of the invention is not particularly limited, and is usually in the range of 5:00 AM to 9:00 PM, and the photon flux density is usually 10 to 2,500 µmol/$m^2$/s.

When a composition of the invention is applied to a crop field, it may be applied before sowing a crop seed, simultaneously with sowing a crop seed, and/or after sowing a crop seed. That is, the frequency of the application of a composition of the invention is once before, simultaneously with, or after sowing a crop seed, twice excluding before the sowing, excluding simultaneously with the sowing, or excluding after the sowing, or three times at all the timing.

When a composition of the invention is applied before sowing a crop seed, it is applied from 50 days before to immediately before the sowing, preferably from 30 days before to immediately before the sowing, more preferably from 20 days before to immediately before the sowing, and still more preferably from 10 days before to immediately before the sowing.

When a composition of the invention is applied after sowing a crop seed, it is usually applied from immediately after the sowing to before flowering. The composition is more preferably applied from immediately after the sowing to before the emergence, or from 1 to 6 leaf stages of the crop. The case where a composition of the invention is applied simultaneously with sowing a crop seed is the case where a sowing machine and a sprayer are integrated with each other.

In the step of applying a composition of the invention in a cultivation area, a compound of formula I or the compound and at least one additional compound selected from the group consisting of the herbicide compound group B and the safener group C are usually mixed with a carrier such as a solid carrier or a liquid carrier, and an auxiliary agent for formulation such as a surfactant is added if necessary to prepare a formulation. Preferable formulation types is aqueous liquid suspension formulations, oil-based suspension formulations, wettable powders, water dispersible granules, granules, water-based emulsions, oil-based emulsions, and emulsifiable concentrates, and more preferable formulation type is emulsifiable concentrates. Furthermore, a formulation containing a compound of formula I alone as an active ingredient and a formulation containing the at least one compound selected from the group consisting of the herbicide compound group B and the safener group C as an active ingredient may be used in combination. Furthermore, a formulation containing the present composition as active ingredients and a formulation containing another herbicide as an active ingredient may be used in combination.

Examples of the method of applying a composition of the invention in a cultivation area include a method of spraying it on the soil in the cultivation area and a method of spraying the present composition on a weeds that are growing. The composition is usually diluted with water, followed by spraying. The spray volume is not particularly limited, and is usually 50 to 1,000 L/ha, preferably 100 to 500 L/ha, and more preferably 140 to 300 L/ha.

Specific examples of the weed species to be controlled by the present composition include, but are not limited to, the weed species described below.

Urticaceae weeds to be controlled include *Urtica urens*.

Polygonaceae weeds to be controlled include *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius*, and *Rumex acetosa*.

Portulacaceae weeds to be controlled include *Portulaca oleracea*.

Caryophyllaceae weeds to be controlled include *Stellaria media, Stellaria aquatica, Cerastium holosteoides, Cerastium glomeratum, Spergula arvensis*, and *Silene gallica*.

Molluginaceae weeds to be controlled include *Mollugo verticillate*.

Chenopodiaceae weeds to be controlled include *Chenopodium album, Chenopodium ambrosioides, Kochia scoparia, Salsola kali*, and *Atriplex* spp.

Amaranthaceae weeds to be controlled include *Amaranthus retroflexus, Amaranthus viridis. Amaranthus lividus, Amaranthus spinosus, Amaranthus hybridus, Amaranthus palmeri, Amaranthus patulus*, Waterhemp (*Amaranthus tuberculatus, Amaranthus rudis*, or *Amaranthus tamariscinus*), *Amaranthus blitoides, Amaranthus deflexus, Amaranthus quitensis, Alternanthera philoxeroides, Alternanthera sessilis*, and *Alternanthera tenella*.

Papaveraceae weeds to be controlled include *Papaver rhoeas, Papaver dubium*, and *Argemone Mexicana*.

Brassicaceae weeds to be controlled include *Raphanus raphanistrum, Raphanus sativus, Sinapis arvensis, Capsella bursa-pastoris, Brassica juncea, Brassica napus, Descurainia pinnata, Rorippa islandica, Rorippa sylvestris, Thlaspi arvense, Myagrum rugosum, Lepidium virginicum*, and *Coronopus didymus*.

Capparaceae weeds to be controlled include *Cleome affinis*.

Fabaceae weeds to be controlled include *Aeschynomene indica, Aeschynomene rudis, Sesbania exalta, Cassia obtusifolia, Cassia occidentalis, Desmodium tortuosum, Desmodium adscendens, Desmodium illinoense, Trnfolium repens, Pueraria lobata, Vicia angustifolia, Indigofera hirsuta, Indigofera truxillensis*, and *Vigna sinensis*.

Oxalidaceae weeds to be controlled include *Oxalis corniculata, Oxalis strica*, and *Oxalis oxyptera*.

Geraniaceae weeds to be controlled include *Geranium carolinense* and *Erodium cicularium*.

Euphorbiaceae weeds to be controlled include *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis*, and *Ricinus communis*.

Malvaceae weeds to be controlled include *Abutilon theophrasti, Sida rhombiforia, Sida cordifolia, Sida spinosa, Sida glaziovii, Sida santaremnensis, Hibiscus trionum, Anoda cristata*, and *Malvastrum coromandelianum*.

Onagraceae weeds to be controlled include *Ludwigia epilobioides, Ludwigia octovalvis, Ludwigia decurre, Oenothera biennis*, and *Oenothera laciniata*.

Sterculiaceae weeds to be controlled include *Waltheria indica*.

Violaceae weeds to be controlled include *Viola arvensis* and *Viola tricolor*.

Cucurbitaceae weeds to be controlled include *Sicyos angulatus, Echinocystis lobata*, and *Momordica charantia*.

Lythraceae weeds to be controlled include *Ammannia multiflora, Ammannia auriculata, Ammannia coccinea, Lythrum salicaria*, and *Rotala indica*.

Elatinaceae weeds to be controlled include *Elatine triandra* and *Elatine californica*.

Apiaceae weeds to be controlled include *Oenanthe javanica, Daucus carota*, and *Conium maculatum*.

Ceratophyllaceae weeds to be controlled include *Ceratophyllum demersum*.

Cabombaceae weeds to be controlled include *Cabomba caroliniana*.

Haloragaceae weeds to be controlled include *Myriophyllum aquaticum, Myriophyllum verticillatum, Myriophyllum spicatum*, and *Myriophyllum heterophyllum*.

Sapindaceae weeds to be controlled include *Cardiospermum halicacabum*.

Primulaceae weeds to be controlled include *Anagallis arvensis*.

Asclepiadaceae weeds to be controlled include *Asclepias syriaca*, and *Ampelamus albidus*.

Rubiaceae weeds to be controlled include *Galium aparine, Galium spurium* var. *echinospermon, Spermacoce latifolia, Richardia brasiliensis*, and *Borreria alata*.

Convolvulaceae weeds to be controlled include *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides*, and *Jacquemontia tamnmfolia*.

Boraginaceae weeds to be controlled include *Myosois arvensis*.

Lamiaceae weeds to be controlled include *Lamium purpureum, Lamium amplexicaule, Leonotis nepetaefolia, Hyptis suaveolens, Hyptis lophanta, Leonurus sibiricus*, and *Stachys arvensis*.

Solanaceae weeds to be controlled include *Datura stramonium, Solanum nigrum, Solanum americanum, Solanum pycanthum, Solanum sarrachoides, Solanum rostratum*,

*Solanum aculeatissimum, Solanum sisymbriifolium, Solanum carolinense, Physalis angulata, Physalis subglabrata,* and *Nicandra physaloides.*

Scrophulariaceae weeds to be controlled include *Veronica hederaefolia, Veronica persica, Veronica arvensis, Lindernia procumbens, Lindernia dubia, Lindernia angustifolia, Bacopa rotundifolia, Dopatrium junceum,* and *Gratiola japonica.*

Plantaginaceae weeds to be controlled include *Plantago asiatica, Plantago lanceolata, Plantago major,* and *Callitriche palustris.*

Asteraceae weeds to be controlled include *Xanthium pensylvanicum, Xanthium occidentale, Xanthium italicum, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parnflora, Senecio vulgaris, Senecio brasiliensis, Senecio grisebachii, Conyza bonariensis, Conyza smatrensis, Conyza canadensis, Ambrosia artemisiaefolia, Ambrosia tifida, Bidens tripartita, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blain villea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophorus, Siegesbeckia orientalis, Soliva sessilis, Eclipta prostrata, Eclipta alba,* and *Centipeda minima.*

Alismataceae weeds to be controlled include *Sagittaria pygmaea, Sagittaria trifolia, Sagittaria sagittifolia, Sagittaria montevidensis, Sagittaria aginashi, Alisma canaliculatum,* and *Alisma plantago-aquatica.*

Limnocharitaceae weeds to be controlled include *Limnocharis flava.*

Hydrocharitaceae weeds to be controlled include *Limnobium spongia, Hydrilla verticillata,* and *Najas guadalupensis.*

Araceae weeds to be controlled include *Pistia stratiotes.*

Lemnaceae weeds to be controlled include *Lemna aoukikusa, Spirodela polyrhiza,* and *Wolffia* spp.

Potamogetonaceae to be controlled include *Potamogeton distinctus, Potamogeton crispus, Potamogeton illinoensis,* and *Stuckenia pectinata.*

Liliaceae weeds to be controlled include *Allium canadense, Allium vineale,* and *Allium macrostenon.*

Pontederiaceae weeds to be controlled include *Eichhornia crassipes, Heteranthera limosa, Monochoria korsakowii,* and *Monochoria vaginalis.*

Commelinaceae weeds to be controlled include *Commelina communis, Commelina bengharensis, Commelina erecta,* and *Murdannia keisak.*

Poaceae weeds to be controlled include *Echinochloa crus-galli, Echinochloa orvzicola, Echinochloa crus-galli var formosensis, Echinochloa oryzoides, Echinochloa colona, Echinochloa crus-pavonis, Setaria viridis, Setaria faberi, Setaria glauca, Setaria geniculata. Digitaria ciliaris, Digitaria sanguinalis, Digitaria horizontalis, Digitaria insularis, Eleusine indica, Poa annua, Poa trivialis, Poa pratensis, Alospecurus aequalis, Alopecurus mvosuroides, Avena fatua, Sorghum halepense, Sorghum vulgare, Agropyron repens, Lolium multiflorum, Lolium perenne, Lolium rigidum, Bromus catharticus, Bromus sterilis, Bromus japonicus, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Chlorisvirgata, Eragrostis pilosa, Rhynchelitrum repens, Dactyloctenium aegyptium, Ischaemum rugosum, Isachne globosa, Orvza sativa, Paspalum notatum, Paspalum maritimum, Paspalum distichum, Pennisetum clandestinum, Pennisetum setosum, Rouboellia cochinchinensis, Leptochloa chinensis, Leptochloa fascicularis, Leptochloa filiformis, Leptochloa panicoides, Leersia japonica, Leersia savanuka, Leersia oryzoides, Glyceria leptorrhiza, Glvceria acutiflora, Glvceria maxima, Agrostis gigantea, Agrostis stoloniera, Cynodon dactylon, Dactylis glomerata, Eremochloa ophiuroides, Festuca arundinacea, Festuca rubra, Imperata cylindrica, Miscanthus sinensis, Panicum virgatum,* and *Zoysia japonica.*

Cyperaceae weeds to be controlled include *Cyperus microiria, Cyperus iria, Cyperus compressus, Cyperus difformis, Cyperus flaccidus, Cyperus globosus, Cyperus nipponics, Cyperus odoratus, Cyperus serotinus, Cyperus rotundus, Cyperus esculentus, Kyllinga gracillima, Kyllinga brevifolia, Fimbristylis miliacea, Fimbristylis dichotoma, Eleocharis acicularis, Eleocharis kuroguwai, Schoenoplectiella hotarui, Schoenoplectiella juncoides, Schoenoplectiella wallichii, Schoenoplectiella mucronatus, Schoenoplectiella triangulatus, Schoenoplectiella nipponicus, Schoenoplectiella triqueter, Bolboschoenus koshevnikovii,* and *Bolboschoenus fluviatilis.*

Equisetaceae weeds to be controlled include *Equisetum arvense,* and *Equisetum palustre.*

Salviniaceae weeds to be controlled include *Salvinia natans.*

Azollaceae weeds to be controlled include *Azolla japonica* and *Azolla imbricata.*

Marsileaceae weeds to be controlled include *Marsilea quadrifolia.*

Other weeds to be controlled include *Pithophora, Cladophora, Bryophyta, Marchantiophyta, Anthocerotophyta, Cyanobacteria, Pteridophyta,* sucker of perennial crops (pomaceous fruits, nut trees, citruses, *Humulus lupulus,* grapes, and the like).

In the above-mentioned weeds to be controlled, mutations within the species are not particularly limited. That is, the weeds include weeds having reduced sensitivity to a specific herbicide. The reduced sensitivity may be attributed to a mutation at a target site (target site mutation) or may be attributed to any factors other than the target site mutation (non-target site mutation). Examples of the factor of the reduced sensitivity due to a non-target site mutation include increased metabolism, malabsorption, translocation dysfunction, and excretion to out of system. Examples of the factor of the increased metabolism include the enhanced activity of a metabolizing enzyme such as cytochrome P450 monooxygenase, aryl acylamidase, esterase, or glutathione S-transferase. Examples of the excretion to out of system include transport to the vacuole by an ABC transporter. Examples of the weeds having reduced sensitivity due to a target site mutation include weeds having any one of or two or more of the following amino acid substitutions in the ALS gene: Ala122Thr, Ala122Val, Ala122Tyr, Pro197Ser, Pro197His, Pro197Thr, Pro197Arg, Pro197Leu, Pro197Gln. Pro197Ala, Pro197Ile, Ala205Val, Ala205Phe, Asp376Glu, Arg377His, Trp574Leu, Trp574Gly, Trp574Met, Ser653Thr, Ser653Thr, Ser653Asn, Ser635Ile, Gly654Glu, and Gly645Asp. Similarly, examples of the weeds having reduced sensitivity due to a target site mutation include weeds having any one of or two or more of the following amino acid substitutions in the ACCase gene: Ile1781Leu, Ile1781Val, Ile1781Thr. Trp1999Cys, Trp1999Leu, Ala2004Val, Trp2027Cys, Ile2041Asn, Ile2041Val, Asp2078Gly, Cys2088Arg, Gly2096Ala, and Gly2096Ser.

Similarly, as an example of the weeds having reduced sensitivity due to a target site mutation, PPO inhibitor-resistant weeds having one or more mutations selected from an Arg128Leu mutation, an Arg128Met mutation, an Arg128Gly mutation, an Arg128His mutation, a Gly210 deletion mutation, and a Gly399Ala mutation in PPO. The word "PPO" means protoporphyrinogen oxidase. Weeds usually have PPO1 and PPO2 in PPO, and the above-mentioned mutations may be present in either PPO1 or PPO2 or in both. The case where weeds have the mutations in PPO2 is preferable. For example, the word "Arg128Met" means that the mutation is present in the 128th (the number is standardized with PPO2 of *Amaranthus palmeri*) amino acid. In PPO2 of *Ambrosia artemisiaefolia*, the mutation corresponds to a mutation in the 98th amino acid (Rousonelos, et al., Weed Science (2012) Vol. 60, pgs. 335-344) and is known as Arg98Leu. In this case, Arg98 is equivalent to Arg128 according to the present invention. The Arg128Met mutation and the Arg128Gly mutation in the PPO of the weed to be controlled in the present invention are known in *Amaranthus palmeri* (Giacomini, et al., Pest Management Science (2017) Vol. 73, pgs. 1559-1563), the Arg128His mutation is known in *Lolium rigidum* (Fernandez-Moreno, et al., Weed Science Society of America (WSSA) annual meeting, 2018), and the Gly399Ala mutation is known in *Amaranthus palmeri* (Rangani, et al., WSSA annual meeting, 2018). In the present invention, the above-mentioned reported resistant weeds are particularly effectively controlled, but particularly effectively controlled weeds are not limited thereto. That is, other weeds having the amino acid mutation are similarly controlled. Not only *Amaranthus palmeri* having an Arg128Leu mutation, an Arg128Met mutation, an Arg128Gly mutation, an Arg128His mutation, a Gly210 deletion mutation, or a Gly399Ala mutation, but also, for example, waterhemp having the above-mentioned mutation, *Ambrosia artemisiaefolia* having the above-mentioned mutation. *Lolium rigidum* having the above-mentioned mutation, *Lolium multiflorum* having the above-mentioned mutation, and *Euphorbia heterophylla* having the above-mentioned mutation are effectively controlled.

Similarly, examples of the weeds having reduced sensitivity due to a target site mutation include weeds having an amino acid substitution such as Thr102Ile, Pro106Ser, Pro106Ala, or Pro106Leu in the EPSP gene. In particular, *Eleusine indica, Lolium multiflorum, Lolium rigidum, Digitaria insularis*, waterhemp, *Echinochloa colona*, and the like which are resistant to glyphosate and have one or both of the mutations are effectively controlled. Similarly, examples of the weeds having reduced sensitivity due to a target site include weeds having increased copies of the EPSP gene and *Amaranthus palmeri*, waterhemp, *Kochia scoparia*, and the like which are resistant to glyphosate and have the mutation are particularly effectively controlled. *Conyza canadensis, Conyza smatrensis*, and *Conyza bonariensis* which are resistant to glyphosate in which an ABC transporter is involved are also effectively controlled.

In the cultivation of a crop according to the present invention, plant nutritional management in general cultivation of a crop can be performed. The fertilization system may be based on Precision Agriculture or may be conventionally uniform one. In addition, a nitrogen-fixing bacterium or a mycorrhizal fungus can be inoculated in combination with seed treatment.

Combinations

In certain aspects, controlling effect on weeds is exhibited by using a compound of formulas (I), (II), (III), (IV), (V), (VI), or (VII) and a specific compound in combination.

Accordingly, the present invention features—(i) A herbicidal composition including a compound of formula I and at least one compound selected from the group consisting of a herbicide compound group B and a safener group C, wherein a weight ratio of a compound of formula I to the at least one compound selected from the group consisting of the herbicide compound group B and the safener group C is 1:0.1 to 1:50, and the herbicide compound group B is a group consisting of the following B-1 to B-12:

B-1 acetolactate synthase inhibitors;
B-2 acetyl-CoA carboxylase inhibitors;
B-3 protoporphyrinogen IX oxidase inhibitors;
B-4 4-hydrophenylpyruvate dioxygenase inhibitors;
B-5 phytoene desaturase inhibitors;
B-6 photosystem II inhibitors;
B-7 very long chain fatty acid synthesis inhibitors;
B-8 microtubule formation inhibitors;
B-9 auxin herbicides;
B-10 enolpyruvylshikimate 3-phosphate synthase inhibitors;
B-11 glutamine synthase inhibitors; and
B-12 other herbicides (including agriculturally acceptable salts or derivatives for each of B-1 to B-12)

The present invention also features—(ii) the herbicidal composition according to (i), wherein:
the B-1 is a group consisting of pyrithiobac, pyrithiobac-sodium salt, pyriminobac, pyriminobac-methyl, bispyribac, bispyribac-sodium salt, pyribenzoxim, pyrimisulfan, pyriftalid, triafamone, amidosulfuron, azimsulfuron, bensulfuron, bensulfuron-methyl, chlorimuron, chlorimuron-ethyl, cyclosulfamuron, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, mesosulfuron, mesosulfuron-methyl, metazosulfuron, nicosulfuron, orthosulfamuron, oxasulfuron, primisulfuron, primisulfuron-methyl, propyrisulfuron, pyrazosulfuron, pyrazosulfuron-ethyl, rimsulfuron, sulfometuron, sulfometuron-methyl, sulfosulfuron, trifloxysulfuron, trifloxysulfuron-sodium salt, chlorsulfuron, cinosulfuron, ethametsulfuron, ethametsulfuron-methyl, iodosulfuron, iodosulfuron-methyl-sodium, iofensulfuron, iofensulfuron-sodium, metsulfuron, metsulfuron-methyl, prosulfuron, thifensulfuron, thifensulfuron-methyl, triasulfuron, tribenuron, tribenuron-methyl, triflusulfuron, triflusulfuron-methyl, tritosulfuron, bencarbazone, flucarbazone, flucarbazone-sodium salt, propoxycarbazone, propoxycarbazone-sodium salt, thiencarbazone, thiencarbazone-methyl, cloransulam, cloransulam-methyl, diclosulam, florasulam, flumetsulam, metosulam, penoxsulam, pyroxsulam, imazamethabenz, imazamethabenz-methyl, imazamox, imazamox-ammonium salt, imazapic, imazapic-ammonium salt, imazapyr, imazapyr-isopropylammonium salt, imazaquin, imazaquin-ammonium, imazethapyr, and imazethapyr-ammonium salt (including agriculturally acceptable salts and derivatives thereof for each);

the B-2 is a group consisting of clodinafop, clodinafop-propargyl, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, propaquizafop, quizalofop, quizalofop-ethyl, quizalofop-P, quizalofop-P-ethyl, alloxydim, clethodim, sethoxydim, tepraloxydim, tralkoxydim, and pinoxaden (including agriculturally acceptable salts and derivatives thereof for each);

the B-3 is a group consisting of azafenidin, oxadiazon, oxadiargyl, carfentrazone, carfentrazone-ethyl, saflufenacil, cinidon, cinidon-ethyl, sulfentrazone, pyraclonil, pyraflufen, pyraflufen-ethyl, butafenacil, fluazolate, fluthiacet, fluthiacet-methyl, flufenpyr, flufenpyr-ethyl, flumiclorac, flumiclorac-pentyl, flumioxazin, pentoxazone, oxyfluorfen, acifluorfen, acifluorfen-sodium salt, aclonifen, chlormethoxynil, chlornitrofen, nitrofen, bifenox, fluoroglycofen, fluoroglycofen-ethyl, fomesafen, fomesafen-sodium salt, lactofen, tiafenacil, and ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (including agriculturally acceptable salts and derivatives thereof for each);

the B-4 is a group consisting of benzobicyclon, bicyclopyrone, mesotrione, sulcotrione, tefuryltrione, tembotrione, isoxachlortole, isoxaflutole, benzofenap, pyrasulfotole, pyrazolynate, pyrazoxyfen, fenquinotrione, topramezone, tolpyralate, lancotrione, lancotrione-sodium salt, 2-methyl-N-(5-methyl-1,3,4-oxadiazol-2-yl)-3-(methylsulfonyl)-4-(trifluoromethyl)benzamide (CAS Registry Number: 1400904-50-8), 2-chloro-N-(1-methyl-1H-tetrazol-5-yl)-3-(methylthio)-4-(trifluoromethyl)-benzamide (CAS Registry Number 1361139-71-0), and 4-(4-fluorophenyl)-6-[(2-hydroxy-6-oxo-1-cyclohexene-1-yl)carbonyl]-2-methyl-1,2,4-triazine-3,5(2H,4H)-dione (CAS Registry Number 1353870-34-4) (including agriculturally acceptable salts and derivatives thereof for each);

the B-5 is a group consisting of diflufenican, picolinafen, beflubutamid, norflurazon, fluridone, flurochloridone, and flurtamone (including agriculturally acceptable salts and derivatives thereof for each);

the B-6 is a group consisting of ioxynil, ioxynil-octanoate, bentazone, pyridate, bromoxynil, bromoxynil-octanoate, chlorotoluron, dimefuron, diuron, linuron, fluometuron, isoproturon, isouron, tebuthiuron, benzthiazuron, methabenzthiazuron, propanil, metobromuron, metoxuron, monolinuron, siduron, simazine, atrazine, propazine, cyanazine, ametryn, simetryn, dimethametryn, prometryn, terbumeton, terbuthylazine, terbutryn, trietazine, hexazinone, metamitron, metribuzin, amicarbazone, bromacil, lenacil, terbacil, chloridazon, desmedipham, and phenmedipham (including agriculturally acceptable salts and derivatives thereof for each);

the B-7 is a group consisting of propachlor, metazachlor, alachlor, acetochlor, metolachlor, S-metolachlor, butachlor, pretilachlor, thenylchlor, indanofan, cafenstrole, fentrazamide, dimethenamid, dimethenamid-P, mefenacet, pyroxasulfone, fenoxasulfone, naproanilide, napropamide, anilofos, flufenacet, and ipfencarbazone (including agriculturally acceptable salts and derivatives thereof for each);

the B-8 is a group consisting of trifluralin, pendimethalin, ethalfluralin, benfluralin, oryzalin, prodiamine, butamifos, dithiopyr, and thiazopyr (including agriculturally acceptable salts and derivatives thereof for each);

the B-9 is a group consisting of 2,4-DB [4-(2,4-dichlorophenoxy)butyric acid] and its salts or esters (dimethylammonium salt, isooctyl ester, and choline salt), MCPA and its salts or esters (dimethylammonium salt, 2-ethylhexyl ester, isooctyl ester, sodium salt, and choline salt), MCPB, mecoprop and its salts or esters (dimethylammonium salt, dioramine salt, ethadyl ester, 2-ethylhexyl ester, isooctyl ester, methyl ester, potassium salt, sodium salt, trolamine salt, and choline salt), mecoprop-P and its salts or esters (dimethylammonium salt, 2-ethylhexyl ester, isobutyl salt, potassium salt, and choline salt), dichlorprop and its salt or ester (butotyl ester, dimethylammonium salt, 2-ethylhexyl ester, isooctyl ester, methyl ester, potassium salt, sodium salt, and choline salt), dichlorprop-P, dichlorprop-P dimethylammonium, triclopyr and its salts or esters (butotyl ester, and triethylammonium salt), fluroxypyr, fluroxypyr-meptyl, picloram and its salts (potassium salt, tris(2-hydroxypropyl)ammonium salt, and choline salt), quinclorac, quinmerac, aminopyralid and its salts (potassium salt, tris(2-hydroxypropyl)ammonium salt, and choline salt), clopyralid and its salts (olamine salt, potassium salt, triethylammonium salt, and choline salt), clomeprop, aminocyclopyrachlor, halauxifen, halauxifen-methyl, florpyrauxifen, and florpyrauxifen-benzyl (including agriculturally acceptable salts and derivatives thereof for each);

the B-10 is a group consisting of glyphosate, glyphosate-isopropylammonium salt, glyphosate-trimesium salt, glyphosate-ammonium salt, glyphosate-diammonium salt, glyphosate-dimethylammonium salt, glyphosate-monoethanolamine salt, glyphosate-sodium salt, glyphosate-potassium salt, and glyphosate-guanidine salt (including agriculturally acceptable salts and derivatives thereof for each);

B-11 is a group consisting of glufosinate, glufosinate-ammonium salt, glufosinate-P, glufosinate-P-sodium salt, and bialaphos (including agriculturally acceptable salts and derivatives thereof for each); and the B-12 is a group consisting of isoxaben, dichlobenil, methiozolin, diallate, butylate, triallate, chlorpropham, asulam, phenisopham, benthiocarb, molinate, esprocarb, pyributicarb, prosulfocarb, orbencarb, EPTC, dimepiperate, swep, difenoxuron, methyldymron, bromobutide, daimuron, cumyluron, diflufenzopyr, diflufenzopyr-sodium salt, etobenzanid, tridiphane, amitrole, clomazone, 2-[(2,4-dichlorophenyl)methyl]-4,4-dimethylisoxazolidin-3-one (CAS Registry Number: 81777-95-9), (3S,4S)—N-(2-fluorophenyl)-1-methyl-2-oxo-4-[3-(trifluoromethyl)phenyl]-3-pyrrolidinecarboxamide (CAS Registry Number: 2053901-33-8), maleic hydrazide, oxaziclomefone, cinmethylin, benfuresate. ACN, dalapon, chlorthiamid, flupoxam, bensulide, paraquat, paraquat-dichloride, diquat, diquat-dibromide, MSMA, indaziflam, and triaziflam (including agriculturally acceptable salts and derivatives thereof for each).

The present invention also features—(iii) the herbicidal composition according to (i) or (ii), wherein the safener group C is a group consisting of benoxacor, cloquintocet, cyometrinil, cyprosulfamide, dichlormid, dicyclonone, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro [4.5]decane, 2,2,5-trimethyl-3-(dichloroacetyl)-1,3-oxazolidine, and N-(2-methoxybenzoyl)-4-[(methylaminocarbonyl) amino]benzenesulfon-amide.

In one embodiment, the present invention includes—(iv) the herbicidal composition according to (i), wherein B-1 is a group consisting of pyrithiobac, pyrithiobac-sodium salt, chlorimuron-ethyl, foramsulfuron, halosulfuron-methyl, nicosulfuron, primisulfuron-methyl, rimsulfuron, trifloxysulfuron-sodium salt, chlorsulfuron, iodosulfuron-methyl-sodium, iofensulfuron sodium, metsulfuron-methyl, prosulfuron, thifensulfuron-methyl, tribenuron-methyl, thiencarbazone-methyl, cloransulam-methyl, flumetsulam, imazamethabenz-methyl, imazamox-ammonium salt, imazapic-ammonium salt, imazapyr-isopropylammonium, imazaquin-ammonium salt, and imazethapyr-ammonium salt (including agriculturally acceptable salts and derivatives thereof for each).

In another embodiment, the present invention includes— (v) the herbicidal composition according to (i), wherein B-2 is a group consisting of fenoxaprop-ethyl, fenoxaprop-P-ethyl, fluazifop-butyl, fluazifop-P-butyl, quizalofop-ethyl, quizalofop-P-ethyl, clethodim, and sethoxydim (including agriculturally acceptable salts and derivatives thereof for each).

In another embodiment, the present invention includes— [6] the herbicidal composition according to [1], wherein B-3 is a group consisting of cartentrazone-ethyl, saflufenacil, sulfentrazone, pyraflufen-ethyl, fluthiacet-methyl, flufenpyr-ethyl, flumiclorac-pentyl, flumioxazin, oxyfluorfen, acifluorfen-sodium salt, fomesafen-sodium salt, lactofen, tiafenacil, and ethyl [(3-(2-chloro-4-fluoro-5-[3-methyl-4-(trifluoromethyl)-2,6-dioxo-1,2,3,6-tetrahydropyrimidine-1-yl]phenoxy)pyridin-2-yl)oxy]acetate (including agriculturally acceptable salts and derivatives thereof for each).

In another embodiment, the present invention includes— [7] the herbicidal composition according to [1], wherein B-4 is a group consisting of bicyclopyrone, mesotrione, tembotrione, isoxaflutole, fenquinotrione, topramezone, tolpyralate, lancotrione-sodium salt, 2-methyl-N-(5-methyl-1,3,4-oxadiazol-2-yl)-3-(methylsulfonyl)-4-(trifluoromethyl)benzamide (CAS Registry Number 1400904-50-8), 2-chloro-N-(1-methyl-1H-tetrazol-5-yl)-3-(methylthio)-4-(trifluoromethyl)-benzamide (CAS Registry Number 1361139-71-0), and 4-(4-fluorophenyl)-6-[(2-hydroxy-6-oxo-1-cyclohexene-1-yl)carbonyl]-2-methyl-1,2,4-triazine-3,5-(2H,4H)-dione (CAS Registry Number 1353870-34-4) (including agriculturally acceptable salts and derivatives thereof for each).

In another embodiment, the present invention includes— [8] the herbicidal composition according to [1], wherein B-5 is a group consisting of norflurazon and fluridone (including agriculturally acceptable salts and derivatives thereof for each).

In another embodiment, the present invention includes— [9] the herbicidal composition according to [1], wherein B-6 is a group consisting of bentazone, bromoxynil octanoate, diuron, linuron, fluometuron, simazine, atrazine, ametryn, prometryn, and metribuzin (including agriculturally acceptable salts and derivatives thereof for each).

In another embodiment, the present invention includes— [10] the herbicidal composition according to [1], wherein B-7 is a group consisting of alachlor, acetochlor, metolachlor, S-metolachlor, dimethenamid, dimethenamid-P, pyroxasulfone, and flufenacet (including agriculturally acceptable salts and derivatives thereof for each).

In another embodiment, the present invention includes— [11] the herbicidal composition according to [1], wherein B-8 is a group consisting of trifluralin, pendimethalin, and ethalfluralin (including agriculturally acceptable salts and derivatives thereof for each).

In another embodiment, the present invention includes— [12] the herbicidal composition according to [1], wherein B-9 is a group consisting of 2,4-DB, fluroxypyr, fluroxypyr-meptyl, clopyralid-olamine salt, clopyralid-potassium salt, clopyralid-triethylammonium salt, halauxifen, halauxifen-methyl, florpyrauxifen, and florpyrauxifen-benzyl (including agriculturally acceptable salts and derivatives thereof for each).

In another embodiment, the present invention includes— [13] the herbicidal composition according to [1], wherein B-10 is a group consisting of a combination of two or more of glyphosate, glyphosate-isopropylammonium salt, glyphosate-ammonium salt, glyphosate-dimethylamine salt, glyphosate-monoethanolamine salt, glyphosate-potassium salt, and glyphosate-guanidine salt (including agriculturally acceptable salts and derivatives thereof for each).

In another embodiment, the present invention includes— [14] the herbicidal composition according to [1], wherein the B-11 is a group consisting of glufosinate, glufosinate-ammonium salt, glufosinate-P, and glufosinate-P-sodium salt (including agriculturally acceptable salts and derivatives thereof for each).

In another embodiment, the present invention includes— [15] the herbicidal composition according to [1], wherein the B-12 is a group consisting of EPTC, diflufenzopyr, diflufenzopyr-sodium salt, clomazone, 2-[(2,4-dichlorophenyl)methyl]-4,4-dimethylisoxazolidin-3-one (CAS Registry Number: 81777-95-9), (3S,4S)—N-(2-fluorophenyl)-1-methyl-2-oxo-4-[3-(trifluoromethyl)phenyl]-3-pyrrolidinecarboxamide (CAS Registry Number: 2053901-33-8), cinmethylin, MSMA, paraquat, paraquat dichloride, diquat, and diquat dibromide (including agriculturally acceptable salts and derivatives thereof for each).

In another embodiment, the present invention includes— [16] The herbicidal composition according to [1], wherein the safener group C is a group consisting of benoxacor, cyprosulfamide, and isoxadifen-ethyl (including agriculturally acceptable salts and derivatives thereof for each).

The present invention also features—[18] A method for controlling weeds, the method including a step of applying a compound of formula I and at least one compound selected from the group consisting of the herbicide compound group B and the safener group C simultaneously or sequentially to a place where weeds are growing or to grow.

In one embodiment, the present invention includes—[19] The method according to [18], wherein a compound of formula I and the at least one compound selected from the group consisting of the herbicide compound group B and the safener group C are used at a weight ratio of 1:0.1 to 1:50.

In another embodiment, the present invention includes— [20] The method according to [18] or [19], wherein the place where weeds are growing or to grow is a crop field.

The present invention also features—[21] A use of the herbicidal composition according to any one of [1] to [16], for controlling weeds.

Herbicidal compositions according to the present invention also include a compound of formula I and at least one compound selected from the group consisting of an herbicide compound group B and a safener group C.

The method for controlling weeds according to the present invention (hereinafter referred to as "present method") includes the step of applying the present composition to a place where weeds are growing or likely to grow in a crop field, a vegetable field, a land under perennial crops, a non-crop land, or the like. In a crop field and a vegetable field, the present Composition may be applied before, simultaneously with, and/or after sowing a crop seed.

The present method includes the step of applying a compound of formula I and at least one compound selected from the group consisting of the herbicide compound group B and the safener group C simultaneously or sequentially to a place where weeds are growing or likely to grow. In the case of the sequential application, the order of the application is not particularly limited.

The present composition is usually a formulation prepared by mixing a compound of formula I and at least one compound selected from the group consisting of the herbicide compound group B and the safener group C with a carrier such as a solid carrier or a liquid carrier and adding an auxiliary agent for formulation such as a surfactant if necessary. Preferable formulation types of such a formulation are aqueous liquid suspension concentrates, wettable powders, water dispersible granules, granules, and emulsifiable concentrates. The present composition may be used in combination with a formulation containing another herbicide as an active ingredient.

The total content of a compound of formula I and the at least one compound selected from the group consisting of the herbicide compound group B and the safener group C in the present composition is within a range of 0.01 to 90% by weight, preferably 1 to 80% by weight.

Hereinafter, when the at least one compound selected from the group consisting of the herbicide compound group B is a salt (for example, glyphosate-potassium salt), the weight of the at least one compound is represented by the acid equivalent.

A mixing ratio of a compound of formula I to the at least one compound selected from the group consisting of the herbicide compound group B and the safener group C in the present composition is within a range of 1:0.05 to 1:100, preferably 1:0.1 to 1:50 by weight ratio.

A ratio of application rates of a compound of formula I to the at least one compound selected from the group consisting of the herbicide compound group B and the safener group C in the present method is within a range of 1:0.05 to 1:100, preferably 1:0.1 to 1:50 by weight ratio.

In some variations, the mixing ratio of a compound of formula I to the at least one compound selected from the group consisting of the herbicide compound group B and the safener group C in the present composition include about 1:0.1, about 1:0.2, about 1:0.3, about 1:0.5, about 1:0.7, about 1:1, about 1:2, about 1:3, about 1:5, about 1:7, about 1:10, about 1:15, about 1:20, about 1:30, and about 1:50 by weight ratio.

In some variations, the ratio of application rates of a compound of formula I to the at least one compound selected from the group consisting of the herbicide compound group B and the safener group C in the present method include about 1:0.1, about 1:0.2, about 1:0.3, about 1:0.5, about 1:0.6, about 1:0.7, about 1:0.8, about 1:1, about 1:1.2, about 1:1.4, about 1:1.6, about 1:1.8, about 1:2, about 1:2.2, about 1:2.4, about 1:2.6, about 1:2.8, about 1:3, about 1:5, about 1:7, about 1:10, about 1:15, about 1:20, about 1:30, and about 1:50 by weight ratio.

The word "about" in the preceding paragraph means that the specified ratio includes the ratio in the range increased or decreased by 10% by weight relative to the specified ratio. For example, a ratio of about 1:2 includes a range of 1:1.8 to 1:2.2.

In the present composition and the present method, particularly preferable examples of the combination of a compound of formula I and the at least one compound selected from the group consisting of the herbicide compound group B and the safener group C and the range of weight ratio thereof include, but are not limited to, the following combinations and the ranges:

a combination of a compound of formulas (I), (II), (III), (IV), (V), (VI), or (VII) and pyrithiobac (1:0.1 to 1:20);

a combination of a compound of formulas (I), (II), (III), (IV), (V), (VI), or (VII) and pyrithiobac-sodium salt (1:0.1 to 1:20);

a combination of a compound of formulas (I), (II), (III), (IV), (V), (VI), or (VII) and chlorimuron-ethyl (1:0.1 to 1:20);

a combination of a compound of formulas (I), (II), (III), (IV), (V), (VI), or (VII) and foramsulfuron (1:0.1 to 1:20);

a combination of a compound of formulas (I), (II), (III), (IV), (V), (VI), or (VII) and halosulfuron-methyl (1:0.1 to 1:20);

a combination of a compound of formulas (I), (II), (III), (IV), (V), (VI), or (VII) and nicosulfuron (1:0.1 to 1:20);

a combination of a compound of formulas (I), (II), (III), (IV), (V), (VI), or (VII) and primisulfuron-methyl (1:0.1 to 1:20);

a combination of a compound of formulas (I), (II), (III), (IV), (V), (VI), or (VII) and rimsulfuron (1:0.1 to 1:20);

a combination of a compound of formulas (I), (II), (III), (IV), (V), (VI), or (VII) and trifloxysulfuron-sodium salt (1:0.1 to 1:20);

a combination of a compound of formulas (I), (II), (III), (IV), (V), (VI), or (VII) and chlorsulfuron (1:0.1 to 1:20);

a combination of a compound of formulas (I), (II), (III), (IV), (V), (VI), or (VII) and iodosulfuron-methyl-sodium (1:0.1 to 1:20);

a combination of a compound of formulas (I), (II), (III), (IV), (V), (VI), or (VII) and iofensulfuron-sodium (1:0.1 to 1:20);

a combination of a compound of formulas (I), (II), (III), (IV), (V), (VI), or (VII) and metsulfuron-methyl (1:0.1 to 1:20);

a combination of a compound of formulas (I), (II), (III), (IV), (V), (VI), or (VII) and prosulfuron (1:0.1 to 1:20);

a combination of a compound of formulas (I), (II), (III), (IV), (V), (VI), or (VII) and thifensulfuron-methyl (1:0.1 to 1:20);

a combination of a compound of formulas (I), (II), (III), (IV), (V), (VI), or (VII) and tribenuron-methyl (1:0.1 to 1:20);

a combination of a compound of formulas (I), (II), (III), (IV), (V), (VI), or (VII) and thiencarbazone-methyl (1:0.1 to 1:20);

a combination of a compound of formulas (I), (II), (III), (IV), (V), (VI), or (VII) and cloransulam-methyl (1:0.1 to 1:20);

a combination of a compound of formulas (I), (II), (III), (IV), (V), (VI), or (VII) and flumetsulam (1:0.1 to 1:20);

a combination of a compound of formulas (I), (II), (III), (IV), (V), (VI), or (VII) and imazamethabenz-methyl (1:0.1 to 1:20);

a combination of a compound of formulas (I), (II), (III), (IV), (V), (VI), or (VII) and imazamox-ammonium salt (1:0.1 to 1:20);

a combination of a compound of formulas (I), (II), (III), (IV), (V), (VI), or (VII) and imazapic-ammonium salt (1:0.1 to 1:20);

a combination of a compound of formulas (I), (II), (III), (IV), (V), (VI), or (VII) and imazapyr-isopropylammonium salt (1:0.1 to 1:20);

a combination of a compound of formulas (I), (II), (III), (IV), (V), (VI), or (VII) and imazaquin-ammonium salt (1:0.1 to 1:20);

a combination of a compound of formulas (I), (II), (III), (IV), (V), (VI), or (VII) and imazethapyr-ammonium salt (1:0.1 to 1:20);

a combination of a compound of formulas (I), (II), (III), (IV), (V), (VI), or (VII) and fenoxaprop-ethyl (1:0.1 to 1:20);

a combination of a compound of formulas (I), (II), (III), (IV), (V), (VI), or (VII) and fenoxaprop-P-ethyl (1:0.1 to 1:20);

a combination of a compound of formulas (I), (II), (II), (IV), (V), (VI), or (VII) and fluazifop-butyl (1:0.1 to 1:20);

a combination of a compound of formulas (I), (II), (III), (IV), (V), (VI), or (VII) and fluazifop-P-butyl (1:0.1 to 1:20);

a combination of a compound of formulas (I), (II), (III), (IV), (V), (VI), or (VII) and quizalofop-ethyl (1:0.1 to 1:20);

a combination of a compound of formulas (I), (II), (III), (IV), (V), (VI), or (VII) and quizalofop-P-ethyl (1:0.1 to 1:20);

a combination of a compound of formulas (I), (II), (III), (IV), (V), (VI), or (VII) and clethodim (1:0.1 to 1:20);

a combination of a compound of formulas (I), (II), (III), (IV), (V), (VI), or (VII) and sethoxydim (1:0.1 to 1:20);

a combination of a compound of formulas (I), (II), (III), (IV), (V), (VI), or (VII) and carfentrazone-ethyl (1:0.1 to 1:20);

a combination of a compound of formulas (I), (II), (III), (IV), (V), (VI), or (VII) and saflufenacil (1:0.1 to 1:20);

a combination of a compound of formulas (I), (II), (III), (IV), (V), (VI), or (VII) and sulfentrazone (1:0.1 to 1:30);

a combination of a compound of formulas (I), (II), (III), (IV), (V), (VI), or (VII) and pyraflufen-ethyl (1:0.1 to 1:30);

a combination of a compound of formulas (I), (II), (III), (IV), (V), (VI), or (VII) and fluthiacet-methyl (1:0.1 to 1:20);

a combination of a compound of formulas (I), (II), (III), (IV), (V), (VI), or (VII) and flufenpyr-ethyl (1:0.1 to 1:20);

a combination of a compound of formulas (I), (II), (III), (IV), (V), (VI), or (VII) and flumiclorac-pentyl (1:0.1 to 1:20);

a combination of a compound of formulas (I), (II), (III), (IV), (V), (VI), or (VII) and flumioxazin (1:0.1 to 1:20);

a combination of a compound of formulas (I), (II), (III), (IV), (V), (VI), or (VII) and oxyfluorfen (1:0.1 to 1:30);

a combination of a compound of formulas (I), (II), (III), (IV), (V), (VI), or (VII) and acifluorfen-sodium salt (1:0.1 to 1:30);

a combination of a compound of formulas (I), (II), (III), (IV), (V), (VI), or (VII) and fomesafen-sodium salt (1:0.1 to 1:30);

a combination of a compound of formulas (I), (II), (II), (IV), (V), (VI), or (VII) and lactofen (1:0.1 to 1:30);

a combination of a compound of formulas (I), (II), (III), (IV), (V), (VI), or (VII) and tiafenacil (1:0.1 to 1:20);

a combination of a compound of formulas (I), (II), (III), (IV), (V), (VI), or (VII) and ethyl [(3-(2-chloro-4-fluoro-5-[3-methyl-4-(trifluoromethyl)-2,6-dioxo-1,2,3,6-tetrahydropyrimidine-1-yl]phenoxy)pyridin-2-yl)oxy]acetate (1:0.1 to 1:20);

a combination of a compound of formulas (I), (II), (III), (IV), (V), (VI), or (VII) and bicyclopyrone (1:0.1 to 1:20);

a combination of a compound of formulas (I), (II), (III), (IV), (V), (VI), or (VII) and mesotrione (1:0.1 to 1:20);

a combination of a compound of formulas (I), (II), (III), (IV), (V), (VI), or (VII) and tembotrione (1:0.1 to 1:20);

a combination of a compound of formulas (I), (II), (III), (IV), (V), (VI), or (VII) and isoxaflutole (1:0.1 to 1:20);

a combination of a compound of formulas (I), (II), (III), (IV), (V), (VI), or (VII) and fenquinotrione (1:0.1 to 1:20);

a combination of a compound of formulas (I), (II), (III), (IV), (V), (VI), or (VII) and topramezone (1:0.1 to 1:20);

a combination of a compound of formulas (I), (II), (II), (IV), (V), (VI), or (VII) and tolpyralate (1:0.1 to 1:20);

a combination of a compound of formulas (I), (II), (III), (IV), (V), (VI), or (VII) and lancotrione-sodium salt (1:0.1 to 1:20); a combination of a compound of formula I and 2-methyl-N-(5-methyl-1,3,4-oxadiazol-2-yl)-3-(methylsulfonyl)-4-(trifluoromethyl)benzamide (CAS Registry Number: 1400904-50-8) (1:0.1 to 1:20);

a combination of a compound of formulas (I), (II), (III), (IV), (V), (VI), or (VII) and 2-chloro-N-(1-methyl-1H-tetrazol-5-yl)-3-(methylthio)-4-(trifluoromethyl)-benzamide (CAS Registry Number: 1361139-71-0) (1:0.1 to 1:20);

a combination of a compound of formulas (I), (II), (III), (IV), (V), (VI), or (VII) and 4-(4-fluorophenyl)-6-[(2-hydroxy-6-oxo-1-cyclohexene-1-yl)carbonyl]-2-methyl-1,2,4-triazine-3,5(2H,4H)-dione (CAS Registry Number: 1353870-34-4) (1:0.1 to 1:20);

a combination of a compound of formulas (I), (II), (III), (IV), (V), (VI), or (VII) and norflurazon (1:0.1 to 1:20);

a combination of a compound of formulas (I), (II), (III), (IV), (V), (VI), or (VII) and fluridone (1:0.1 to 1:20);

a combination of a compound of formulas (I), (II), (III), (IV), (V), (VI), or (VII) and bentazone (1:1 to 1:50);

a combination of a compound of formulas (I), (II), (III), (IV), (V), (VI), or (VII) and bromoxynil octanoate (1:1 to 1:50);

a combination of a compound of formulas (I), (II), (III), (IV), (V), (VI), or (VII) and diuron (1:1 to 1:50);

a combination of a compound of formulas (I), (II), (II), (IV), (V), (VI), or (VII) and linuron (1:1 to 1:50);

a combination of a compound of formulas (I), (II), (III), (IV), (V), (VI), or (VII) and fluometuron (1:1 to 1:50);

a combination of a compound of formulas (I), (II), (III), (IV), (V), (VI), or (VII) and simazine (1:1 to 1:50);

a combination of a compound of formulas (I), (II), (III), (IV), (V), (VI), or (VII) and atrazine (1:1 to 1:50);

a combination of a compound of formulas (I), (II), (III), (IV), (V), (VI), or (VII) and ametryn (1:1 to 1:50);
a combination of a compound of formulas (I), (II), (II), (IV), (V), (VI), or (VII) and prometryn (1:1 to 1:50);
a combination of a compound of formulas (I), (II), (III), (IV), (V), (VI), or (VII) and metribuzin (1:1 to 1:50);
a combination of a compound of formulas (I), (II), (III), (IV), (V), (VI), or (VII) and alachlor (1:1 to 1:50);
a combination of a compound of formulas (I), (II), (III), (IV), (V), (VI), or (VII) and acetochlor (1:1 to 1:50);
a combination of a compound of formulas (I), (II), (III), (IV), (V), (VI), or (VII) and metolachlor (1:1 to 1:50);
a combination of a compound of formulas (I), (II), (III), (IV), (V), (VI), or (VII) and S-metolachlor (1:1 to 1:50);
a combination of a compound of formulas (I), (II), (III), (IV), (V), (VI), or (VII) and dimethenamid (1:1 to 1:50);
a combination of a compound of formulas (I), (II), (II), (IV), (V), (VI), or (VII) and dimethenamid-P (1:1 to 1:50);
a combination of a compound of formulas (I), (II), (III), (IV), (V), (VI), or (VII) and pyroxasulfone (1:0.1 to 1:20);
a combination of a compound of formulas (I), (II), (III), (IV), (V), (VI), or (VII) and flufenacet (1:0.1 to 1:20);
a combination of a compound of formulas (I), (II), (III), (IV), (V), (VI), or (VII) and trifluralin (1:1 to 1:50);
a combination of a compound of formulas (I), (II), (III), (IV), (V), (VI), or (VII) and pendimethalin (1:1 to 1:50);
a combination of a compound of formulas (I), (II), (III), (IV), (V), (VI), or (VII) and ethalfluralin (1:1 to 1:50);
a combination of a compound of formulas (I), (II), (III), (IV), (V), (VI), or (VII) and 2,4-DB (1:1 to 1:50);
a combination of a compound of formulas (I), (II), (III), (IV), (V), (VI), or (VII) and fluroxypyr (1:1 to 1:50);
a combination of a compound of formulas (I), (II), (III), (IV), (V), (VI), or (VII) and fluroxypyr-meptyl (1:1 to 1:50);
a combination of a compound of formulas (I), (II), (III), (IV), (V), (VI), or (VII) and clopyralid-olamine salt (1:1 to 1:50);
a combination of a compound of formulas (I), (II), (III), (IV), (V), (VI), or (VII) and clopyralid-potassium salt (1:1 to 1:50);
a combination of a compound of formulas (I), (II), (III), (IV), (V), (VI), or (VII) and clopyralid-triethylammonium salt (1:1 to 1:50);
a combination of a compound of formulas (I), (II), (III), (IV), (V), (VI), or (VII) and halauxifen (1:0.1 to 1:20);
a combination of a compound of formulas (I), (II), (III), (IV), (V), (VI), or (VII) and halauxifen-methyl (1:0.1 to 1:20);
a combination of a compound of formulas (I), (II), (III), (IV), (V), (VI), or (VII) and florpyrauxifen (1:0.1 to 1:20);
a combination of a compound of formulas (I), (II), (III), (IV), (V), (VI), or (VII) and florpyrauxifen-benzyl (1:0.1 to 1:20);
a combination of a compound of formulas (I), (II), (III), (IV), (V), (VI), or (VII) and glyphosate (1:1 to 1:50);
a combination of a compound of formulas (I), (II), (II), (IV), (V), (VI), or (VII) and glyphosate-isopropylammonium salt (1:1 to 1:50);
a combination of a compound of formulas (I), (II), (III), (IV), (V), (VI), or (VII) and glyphosate-ammonium salt (1:1 to 1:50);
a combination of a compound of formulas (I), (II), (III), (IV), (V), (VI), or (VII) and glyphosate-dimethylamine salt (1:1 to 1:50);
a combination of a compound of formulas (I), (II), (III), (IV), (V), (VI), or (VII) and glyphosate-monoethanolamine salt (1:1 to 1:50);
a combination of a compound of formulas (I), (II), (III), (IV), (V), (VI), or (VII) and glyphosate-potassium salt (1:1 to 1:50);
a combination of a compound of formulas (I), (II), (III), (IV), (V), (VI), or (VII) and glyphosate-guanidine salt (1:1 to 1:50);
a combination of a compound of formulas (I), (II), (III), (IV), (V), (VI), or (VII) and glufosinate (1:1 to 1:50);
a combination of a compound of formulas (I), (II), (III), (IV), (V), (VI), or (VII) and glufosinate-ammonium salt (1:1 to 1:50);
a combination of a compound of formulas (I), (II), (III), (IV), (V), (VI), or (VII) and glufosinate-P (1:1 to 1:50);
a combination of a compound of formulas (I), (II), (III), (IV), (V), (VI), or (VII) and glufosinate-P-sodium salt (1:1 to 1:50);
a combination of a compound of formulas (I), (II), (III), (IV), (V), (VI), or (VII) and EPTC (1:1 to 1:50);
a combination of a compound of formulas (I), (II), (III), (IV), (V), (VI), or (VII) and diflufenzopyr (1:1 to 1:50);
a combination of a compound of formulas (I), (II), (III), (IV), (V), (VI), or (VII) and diflufenzopyr-sodium salt (1:1 to 1:50);
a combination of a compound of formulas (I), (II), (III), (IV), (V), (VI), or (VII) and clomazone (1:1 to 1:50);
a combination of a compound of formulas (I), (II), (III), (IV), (V), (VI), or (VII) and 2-[(2,4-dichlorophenyl)methyl]-4,4-dimethylisoxazolidin-3-one (CAS Registry Number: 81777-95-9) (1:1 to 1:50);
a combination of a compound of formulas (I), (II), (III), (IV), (V), (VI), or (VII) and (3S,4S)—N-(2-fluorophenyl)-1-methyl-2-oxo-4-[3-(trifluoromethyl)phenyl]-3-pyrrolidinecarboxamide (CAS Registry Number: 2053901-33-8) (1:1 to 1:50);
a combination of a compound of formulas (I), (II), (III), (IV), (V), (VI), or (VII) and cinmethylin (1:1 to 1:50);
a combination of a compound of formulas (I), (II), (III), (IV), (V), (VI), or (VII) and MSMA (1:1 to 1:50);
a combination of a compound of formulas (I), (II), (III), (IV), (V), (VI), or (VII) and paraquat (1:1 to 1:50);
a combination of a compound of formulas (I), (II), (III), (IV), (V), (VI), or (VII) and paraquat-dichloride (1:1 to 1:50);
a combination of a compound of formulas (I), (II), (III), (IV), (V), (VI), or (VII) and diquat (1:1 to 1:50);
a combination of a compound of formulas (I), (II), (III), (IV), (V), (VI), or (VII) and diquat-dibromide (1: to 1:50);
a combination of a compound of formulas (I), (II), (III), (IV), (V), (VI), or (VII) and benoxacor (1:0.1 to 1:20);
a combination of a compound of formulas (I), (II), (III), (IV), (V), (VI), or (VII) and cyprosulfamide (1:0.1 to 1:20); or
a combination of a compound of formulas (I), (II), (III), (IV), (V), (VI), or (VII) and isoxadifen-ethyl (1:0.1 to 1:20).

Before, simultaneously with, and/or after sowing a crop seed treated with one or more compounds selected from the group consisting of an insecticide compound, a nematicide compound, a fungicide compound, and the like, the present composition may be applied to the field in which the crop seed have been sown or is to be sown.

In some embodiments, the present composition may be used in combination with another pesticidally-active compound. Examples of the insecticide compound, the nematicide compound, and the fungicide compound which may be used in combination with the present composition include neonicotinoid compounds, diamide compounds, carbamate compounds, organophosphorus compounds, biological nematicide compounds, other insecticide compounds and nematicide compounds, azole compounds, strobilurin compounds, metalaxyl compounds, SDHI compounds, and other fungicide compounds and plant growth regulators.

EXAMPLES

The presently disclosed subject matter will be better understood by reference to the following Examples, which are provided as exemplary of the invention, and not by way of limitation.

Compound Synthesis and Characterization

Steps in the following Examples illustrate a procedure for each step in an overall synthetic transformation, and the starting material for each step may not have necessarily been prepared by a procedure described in other Examples or Steps. $^1$H-NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, and "br s" means broad singlet. Mass spectra (MS) are reported as the molecular weight of the highest isotopic abundance parent ion (M+1) formed by addition of H$^+$ (molecular weight of 1) to the molecule, or (M−1) formed by the loss of H$^+$ (molecular weight of 1) from the molecule, observed by using liquid chromatography coupled to a mass spectrometer (LCMS) using either atmospheric pressure chemical ionization (AP+) where "amu" stands for unified atomic mass units or electrospray ionization (ES$^+$).

Example 1. Preparation of 4-chloro-2',3',4',5',6,6'-hexafluoro-[1,1'-biphenyl]-3-sulfonic acid (Compound 1003)

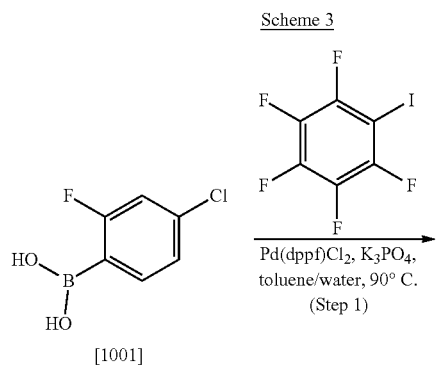

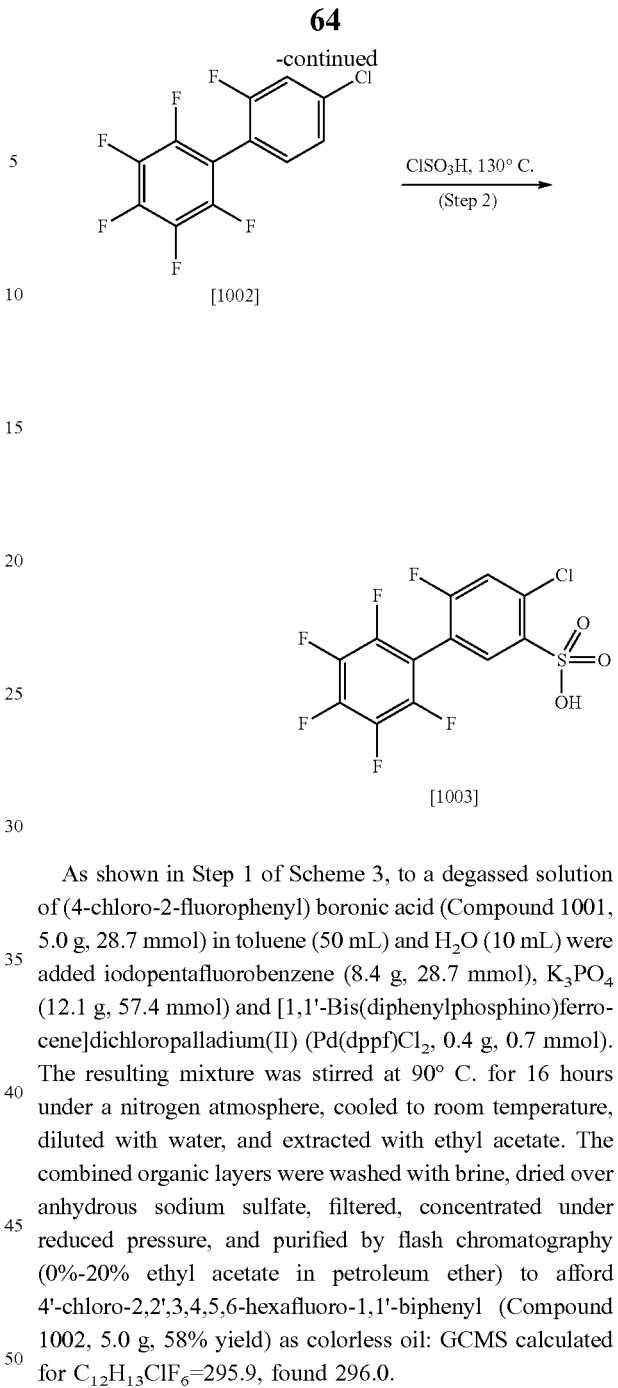

As shown in Step 1 of Scheme 3, to a degassed solution of (4-chloro-2-fluorophenyl) boronic acid (Compound 1001, 5.0 g, 28.7 mmol) in toluene (50 mL) and H$_2$O (10 mL) were added iodopentafluorobenzene (8.4 g, 28.7 mmol), K$_3$PO$_4$ (12.1 g, 57.4 mmol) and [1,1'-Bis(diphenylphosphino)ferrocene]dichloropalladium(II) (Pd(dppf)Cl$_2$, 0.4 g, 0.7 mmol). The resulting mixture was stirred at 90° C. for 16 hours under a nitrogen atmosphere, cooled to room temperature, diluted with water, and extracted with ethyl acetate. The combined organic layers were washed with brine, dried over anhydrous sodium sulfate, filtered, concentrated under reduced pressure, and purified by flash chromatography (0%-20% ethyl acetate in petroleum ether) to afford 4'-chloro-2,2',3,4,5,6-hexafluoro-1,1'-biphenyl (Compound 1002, 5.0 g, 58% yield) as colorless oil: GCMS calculated for C$_{12}$H$_{13}$ClF$_6$=295.9, found 296.0.

As shown in Step 2 of Scheme 3, a mixture of 4'-chloro-2,2',3,4,5,6-hexafluoro-1,1'-biphenyl (5.0 g, 16.9 mmol) in HSO$_3$Cl (15 mL) was stirred at 130° C. for 2 hours under a nitrogen atmosphere. The mixture was cooled, concentrated under reduced pressure, diluted with water, and extracted with ethyl acetate. The combined organic layers were washed with brine, dried over anhydrous sodium sulfate, filtered, concentrated under reduced pressure, and purified by reversed-phase flash chromatography (5%-35% acetonitrile in water) to afford 4-chloro-2',3',4',5',6,6'-hexafluoro-[1,1'-biphenyl]-3-sulfonic acid (Compound 1003, 1.6 g, 25% yield) as a yellow solid: MS (ESI) calculated for C$_{12}$H$_{13}$ClF$_6$O$_3$S [M−1]$^-$=375.0, found 375.1.

Example 2. Preparation of methyl (S)-2-((4-chloro-2',3',4',5',6,6'-hexafluoro-[1,1'-biphenyl]-3-yl)thio)propanoate (Compound 1), methyl (R)-2-((4-chloro-2',3',4',5',6,6'-hexafluoro-[1,1'-biphenyl]-3-yl)thio)propanoate (Compound 2), (S)-2-((4-chloro-2',3',4',5',6,6'-hexafluoro-[1,1'-biphenyl]-3-yl)thio)propanoic acid (Compound 3), and (R)-2-((4-chloro-2',3',4',5',6,6'-hexafluoro-[1,1'-biphenyl]-3-yl)thio)propanoic acid (Compound 4)

reduced pressure to afford 4-chloro-2',3',4',5',6,6'-hexafluoro-[1,1'-biphenyl]-3-sulfonyl chloride (Compound 1004, 490 mg, crude) as a yellow semi-solid. This material was used in subsequent reactions as is.

As shown in Step 2 of Scheme 4, 4-chloro-2',3',4',5',6,6'-hexafluoro-[1,1'-biphenyl]-3-sulfonyl chloride was dissolved in AcOH (10 mL) and concentrated HCl (2 mL) and was added $SnCl_2$ (2.5 g, 13.3 mmol) in portions at 20° C. under a nitrogen atmosphere. The resulting mixture was

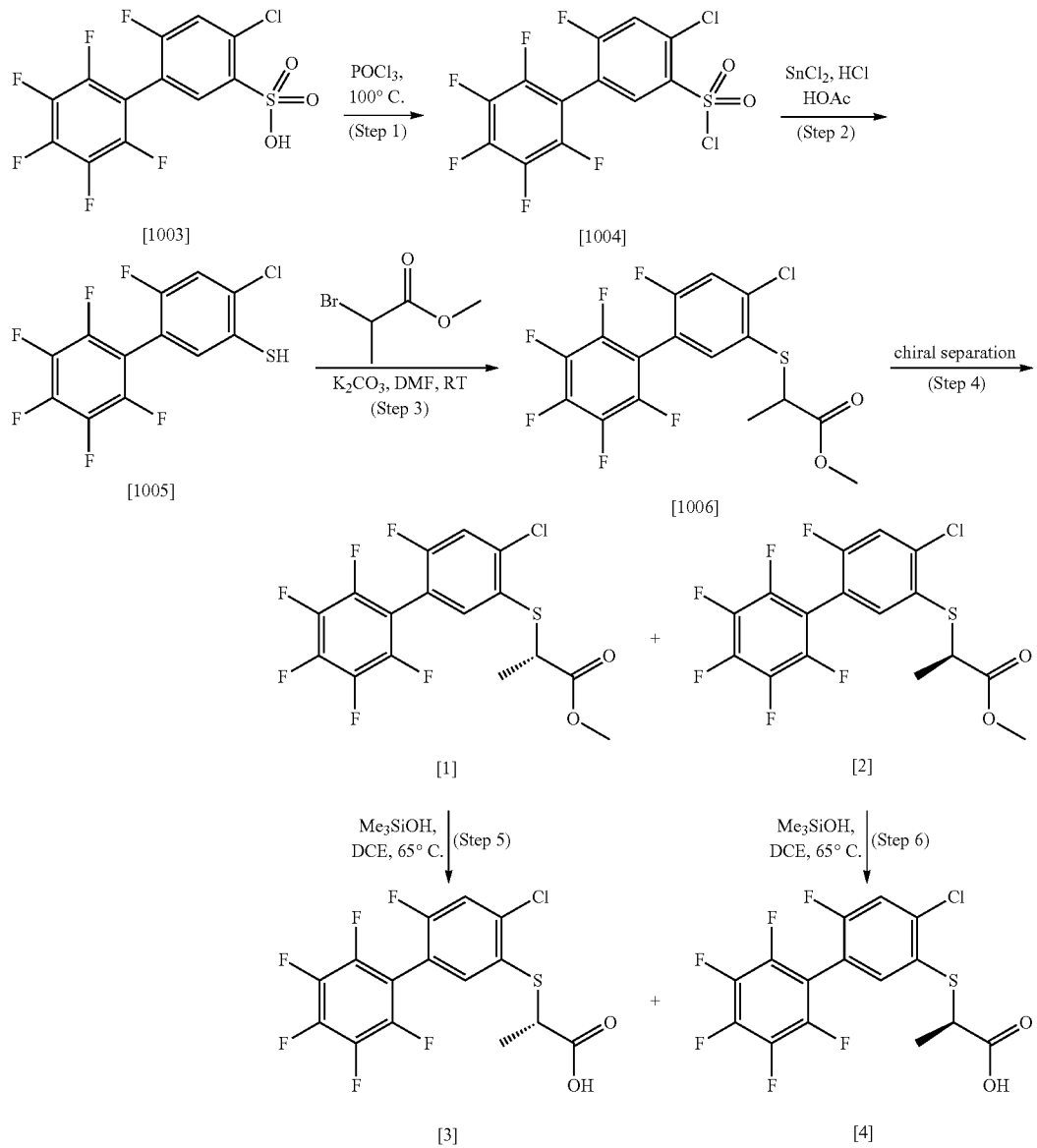

As shown in Step 1 of Scheme 4, a mixture of 4-chloro-2',3',4',5',6,6'-hexafluoro-[1,1'-biphenyl]-3-sulfonic acid (Compound 1003, 500 mg, 1.32 mmol) in phosphorus oxychloride (2 mL) was stirred at 100° C. for 16 hours under a nitrogen atmosphere. The mixture was cooled and the volatiles removed under reduced pressure. The residue was diluted with water and extracted with ethyl acetate. The combined organic layers were washed with brine, dried over anhydrous sodium sulfate, filtered, and concentrated under stirred at 80° C. for 2 hours under a nitrogen atmosphere, diluted with water, and extracted with ethyl acetate. The combined organic layers were washed with brine, dried over anhydrous sodium sulfate, filtered, and concentrated under reduced pressure to afford 4-chloro-2',3',4',5',6,6'-hexafluoro-[1,1'-biphenyl]-3-thiol (Compound 1005, 2.0 g, crude) as yellow oil: MS (ESI) calculated for $C_{12}H_3ClF_6S$ [M−1]$^-$=327.1, found, 327.1. This material was used in subsequent reactions as is.

As shown in Step 3 of Scheme 4, to a stirred mixture of 4-chloro-2',3',4',5',6,6'-hexafluoro-[1,1'-biphenyl]-3-thiol (1.5 g, 4.56 mmol) in DMF (15 mL) was added methyl 2-bromopropanoate (1.5 g, 9.18 mmol). The resulting mixture was stirred at room temperature for 3 hours under a nitrogen atmosphere, diluted with water, and extracted with ethyl acetate. The combined organic layers were washed with brine, dried over anhydrous sodium sulfate, filtered, concentrated under reduced pressure, and purified by flash chromatography (0%-30% ethyl acetate in petroleum ether) to afford methyl 2-((4-chloro-2',3',4',5',6,6'-hexafluoro-[1,1'-biphenyl]-3-yl)thio)propanoate (Compound 1006, 670 mg, 35% yield) as yellow oil: GCMS calculated for $C_{16}H_9ClF_6O_2S$=414.0, found 414.0.

As shown in Step 4 of Scheme 4, racemic methyl 2-((4-chloro-2',3',4',5',6,6'-hexafluoro-[1,1'-biphenyl]-3-yl)thio)propanoate (670.0 mg) was separated into its enantiomeric components by preparative chiral-HPLC using the following conditions—Column: CHIRALPAK AD-3, 4.6×100 mm; 3 um; Mobile Phase 95:5 hexane/(1:1 MeOH:EtOH) to afford methyl (S)-2-((4-chloro-2',3',4',5',6,6'-hexafluoro-[1,1'-biphenyl]-3-yl)thio)propanoate (Compound 1, 350 mg, 40% yield) as yellow oil: GCMS calculated for $C_{16}H_9ClF_6O_2S$, 414.0; found, 414.0. Methyl (R)-2-((4-chloro-2',3',4',5',6,6'-hexafluoro-[1,1'-biphenyl]-3-yl)thio)propanoate (Compound 2, 140 mg, 20% yield) was recovered as a second eluting compound as a yellow oil: GCMS calculated for $C_{16}H_9ClF_6O_2S$=414.0, found 414.0.

As shown in Step 5 of Scheme 4, to a stirred mixture of methyl (S)-2-((4-chloro-2',3',4',5',6,6'-hexafluoro-[1,1'-biphenyl]-3-yl)thio)propanoate (300 mg, 0.08 mmol) in DCE (3 mL) was added trimethylstannanol (262 mg, 1.46 mmol). The resulting solution was stirred at 65° C. for 16 hours, cooled to room temperature, diluted with water, acidified to pH 4-5 with formic acid, and extracted with ethyl acetate. The combined organic layers were washed with brine, dried over anhydrous sodium sulfate, filtered, concentrated under reduced pressure, and purified by reversed-phase flash chromatography (5%-70% acetonitrile in water) to afford (S)-2-((4-chloro-2',3',4',5',6,6'-hexafluoro-[1,1'-biphenyl]-3-yl)thio)propanoic acid (Compound 3, 237 mg, 81% yield) as colorless oil: MS (ESI) calculated for $C_{15}H_7ClF_6:2S$ [M-]-=398.9, found 398.9; $^1$H-NMR (400 MHz, DMSO-$d_6$) δ 12.94 (s, 1H), 7.86 (d, J=9.6 Hz, 1H), 7.81 (d, J=7.2 Hz, 1H), 4.15-4.05 (m, 1H), 1.43 (d, J=7.2 Hz, 3H); $^{19}$F-NMR (376 MHz, DMSO-$d_6$) δ −113.46, −140.46, −153.08, −161.97.

As shown in Step 6 of Scheme 4, a similar protocol as described in Step 5 afforded (R)-2-((4-chloro-2',3',4',5',6,6'-hexafluoro-[1,1'-biphenyl]-3-yl)thio)propanoic acid (Compound 4, 73% yield) as colorless oil: MS (EST) calculated for $C_{15}H_7ClF_6O_2S$ [M-1]$^-$=398.9, found 398.9; $^1$H-NMR (400 MHz, DMSO-$d_6$) δ 12.56 (s, 1H), 7.86 (d, J=9.6 Hz, 1H), 7.82 (d, J=7.2 Hz, 1H), 4.15-4.05 (m, 1H), 1.43 (d, J=7.2 Hz, 3H); $^{19}$F-NMR (376 MHz, DMSO-$d_6$) δ −113.46, −140.46, −153.08, −161.97.

Example 3. Preparation of methyl (S)-3-(2-((4-chloro-2',3',4',5',6,6'-hexafluoro-[1,1'-biphenyl]-3-yl)thio)propanamido)propanoate (Compound 5), methyl (R)-3-(2-((4-chloro-2',3',4',5',6,6'-hexafluoro-[1,1'-biphenyl]-3-yl)thio)propanamido)propanoate (Compound 6), (S)-3-(2-((4-chloro-2',3',4',5',6,6'-hexafluoro-[1,1'-biphenyl]-3-yl)thio)propanamido)propanoic acid (Compound 7), and (R)-3-(2-((4-chloro-2',3',4',5',6,6'-hexafluoro-[1,1'-biphenyl]-3-yl)thio)propanamido)propanoic acid (Compound 8)

Scheme 5

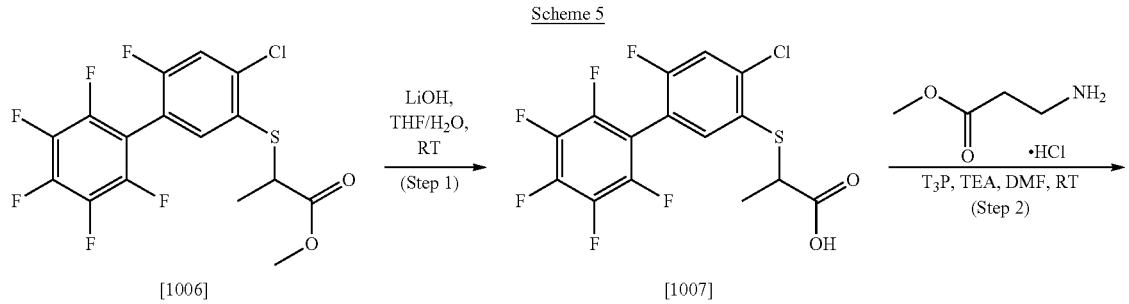

[1006] [1007]

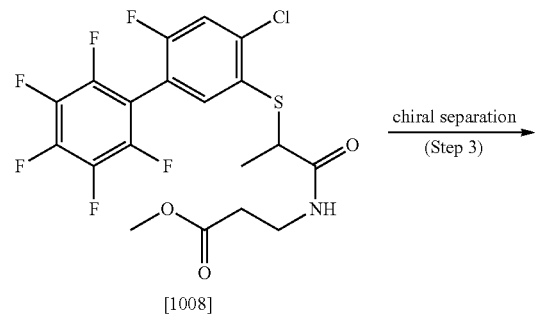

[1008]

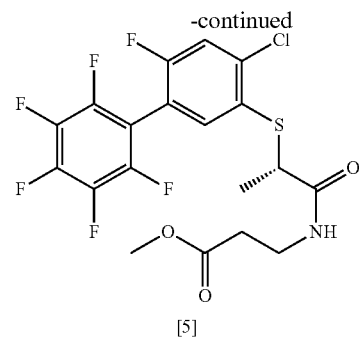

[5]

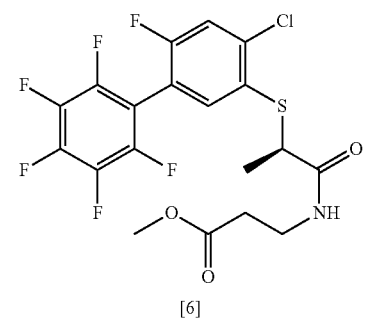

[6]

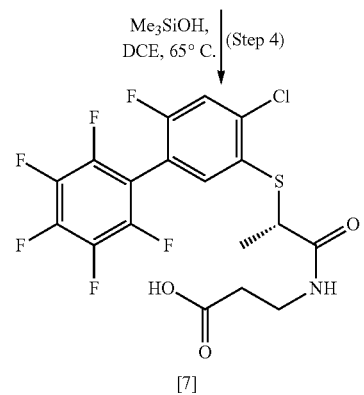

[7]

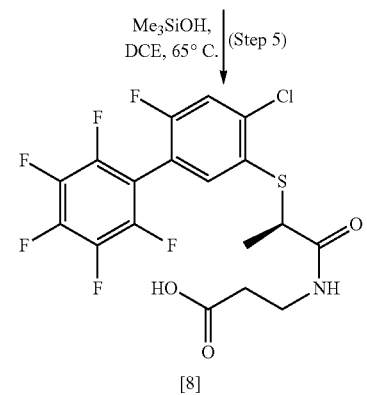

[8]

As shown in Step 1 of Scheme 5, to a stirred mixture of methyl 2-({4-chloro-2',3',4',5',6,6'-hexafluoro-[1,1'-biphenyl]-3-yl}sulfanyl)propanoate (200 mg, 0.48 mmol) in THF (1.8 mL) and water (0.6 mL) was added LiOH (35 mg, 1.44 mmol). The resulting mixture was stirred at room temperature for 2 hours, diluted with water, acidified to pH 4-5 with formic acid, and extracted with ethyl acetate. The combined organic layers were washed with brine, dried over anhydrous sodium sulfate, filtered, and concentrated under reduced pressure to afford 2-((4-chloro-2',3',4',5',6,6'-hexafluoro-[1,1'-biphenyl]-3-yl)thio)propanoic acid (Compound 1007, 195 mg, crude) as colorless oil: MS (ESI) calculated for $C_{15}H_7ClF_6O_2S$ [M-1]$^-$=389.9, found 390.0.

As shown in Step 2 of Scheme 5, to a stirred mixture of 2-((4-chloro-2',3',4',5',6,6'-hexafluoro-[1,1'-biphenyl]-3-yl)thio)propanoic acid (110 mg, 0.27 mmol) in DMF (1 mL) were added $T_3P$ (propylphosphonic anhydride, 174.6 mg, 0.54 mmol), methyl 3-aminopropanoate hydrochloride (38 mg, 0.54 mmol), and triethylamine (83 mg, 0.54 mmol) under a nitrogen atmosphere. The mixture was stirred at 25° C. for 16 hours under a nitrogen atmosphere, diluted with water, and extracted with ethyl acetate. The combined organic layers were washed with brine, dried over anhydrous sodium sulfate, filtered, concentrated under reduced pressure, and purified by preparative-TLC (EtOAc/petroleum ether=1:1) to afford methyl 3-(2-((4-chloro-2',3',4',5',6,6'-hexafluoro-[1,1'-biphenyl]-3-yl)thio)propanamido)propanoate (Compound 1008, 65 mg, 48% yield) as a white solid: MS (ESI) calculated for $C_{19}H_{16}ClF_4NO_3S$ [M+1]$^+$=486.0, found 486.1.

As shown in Step 3 of Scheme 5, racemic methyl 3-(2-((4-chloro-2',3',4',5',6,6'-hexafluoro-[1,1'-biphenyl]-3-yl)thio)propanamido)propanoate (65 mg) was separated by preparative chiral-HPLC with the following conditions— Column: CHIRALPAK IG, 2×25 cm, 5 μm; Mobile Phase 15% hexane (0.5% 2 M $NH_3$-MeOH)/EtOH to afford methyl (R)-3-(2-((4-chloro-2',3',4',5',6,6'-hexafluoro-[1,1'-biphenyl]-3-yl)thio)propanamido)propanoate (Compound 5, 19 mg, 38% yield) as a white solid: MS (ESI) calculated for $C_{19}H_{16}ClF_4NO_3S$ [M+1]$^+$=486.0, found 486.1; $^1$H-NMR (400 MHz, DMSO-$d_6$) δ 8.22-8.15 (m, 1H), 7.86 (d, J=9.6 Hz, 1H), 7.66 (d, J=7.2 Hz, 1H), 4.01-3.92 (m, 1H), 3.56 (s, 3H), 3.29-3.19 (m, 2H), 2.45-2.27 (m, 2H), 1.38 (d, J=6.8 Hz, 3H): $^{19}$F-NMR (377 MHz, DMSO-$d_6$) δ −113.69, −140.56, −153.17, −161.96. Also recovered as a second eluting peak was methyl (S)-3-(2-((4-chloro-2',3',4',5',6,6'-hexafluoro-[1,1'-biphenyl]-3-yl)thio)propanamido)propanoate (Compound 6, 27 mg, 40% yield) as a white solid: MS (ESI) calculated for $C_{19}H_{16}ClF_4NO_3S$ [M+1]$^+$=486.0, found 486.1; $^1$H-NMR (400 MHz, DMSO-$d_6$) δ 8.22-8.15 (m, 1H), 7.86 (d, J=9.6 Hz, 1H), 7.66 (d, J=7.2 Hz, 1H), 4.01-3.92 (m, 1H), 3.56 (s, 3H), 3.29-3.19 (m, 2H), 2.45-2.27 (m, 2H), 1.38 (d, J=6.8 Hz, 3H); $^{19}$F-NMR (377 MHz, DMSO-$d_6$) δ −113.69, −140.56, −153.17, −161.96.

As shown in Steps 4 and 5 of Scheme 5, using a similar protocol as described in Step 5 of Scheme 4 afforded (S)-3-(2-((4-chloro-2',3',4',5',6,6'-hexafluoro-[1,1'-biphenyl]-3-yl)thio)propanamido)propanoic acid (Compound 7, 56% yield) as a white solid: MS (ESI) calculated for $C_{18}H_{12}ClF_6NO_3S$ [M+1]$^+$, 472.0; found, 472.0; $^1$H-NMR (400 MHz, DMSO-$d_6$) δ 8.18 (t, J=5.6 Hz, 1H), 7.85 (d, J=9.6 Hz, 1H), 7.65 (d, J=7.2 Hz, 1H), 4.00-3.95 (m, 1H), 3.22-3.17 (m, 2H), 2.29-2.21 (m, 2H), 1.38 (d, J=6.8 Hz, 3H); $^{19}$F-NMR (376 MHz, DMSO-$d_6$) δ −113.77, −140.60, −153.10, −161.88; and (R)-3-(2-((4-chloro-2',3',4',5',6,6'-hexafluoro-[1,1'-biphenyl]-3-yl)thio)propanamido)propanoic acid (Compound 8, 53% yield) as white solid: MS (ESI) calculated for $C_{18}H_{12}ClF_6NO_3S$ [M+1]$^+$=472.0, found 472.0; $^1$H-NMR (400 MHz, DMSO-$d_6$) δ 8.18 (t, J=5.6 Hz, 1H), 7.85 (d, J=9.6 Hz, 1H), 7.65 (d, J=7.2 Hz, 1H), 3.99-3.96 (m, 1H), 3.23-3.16 (m, 2H), 2.34-2.18 (m, 2H), 1.38 (d, J=6.8 Hz, 3H); $^{19}$F-NMR (376 MHz, DMSO-d$_6$) δ –113.76, –140.61, –153.09, –161.88.

Using the appropriate amino acid ester in transformations similar to those described for Steps 1 to 5 of Scheme 5, the following compounds were also prepared:

methyl ((S)-2-((4-chloro-2',3',4',5',6,6'-hexafluoro-[1,1'-biphenyl]-3-yl)thio)propanoyl)-L-prolinate (Compound 9), isolated as a white solid: MS (EST) calculated for $C_{21}H_{16}ClF_6NO_3S$ [M+1]$^+$=512.0, found 512.0; $^1$H-NMR (400 MHz, CD$_3$OD) δ 7.78-7.76 (m, 1H), 7.63-7.60 (m, 1H), 4.38-4.35 (m, 1H), 4.25-4.24 (m, 1H), 3.71-3.65 (m, 4H), 3.68-3.64 (m, 1H), 1.99-1.95 (m, 4H), 1.48-1.47 (m, 3H); $^{19}$F-NMR (376 MHz, CD$_3$OD) δ –112.1, –142.63, –156.1, –164.7;

methyl ((R)-2-((4-chloro-2',3',4',5',6,6'-hexafluoro-[1,1'-biphenyl]-3-yl)thio)propanoyl)-L-prolinate (Compound 10), isolated as a white solid: MS (ESI) calculated for ($C_{21}H_{16}ClF_6NO_3S$) [M+1]$^+$=512.0, found 512.2; $^1$H-NMR (400 MHz, CD$_3$OD) δ 7.82-7.80 (m, 1H), 7.59-7.57 (m, 1H), 4.42-4.39 (m, 1H), 4.28-4.24 (m, 1H), 3.77-3.72 (m, 2H), 3.55 (s, 3H), 2.28-2.25 (m, 1H), 2.02-1.95 (m, 3H), 1.46-1.44 (m, 3H); $^{19}$F-NMR (376 MHz, CD$_3$OD) δ –113.31, –142.45, –156.86, –165.33;

((S)-2-((4-chloro-2',3',4',5',6,6'-hexafluoro-[1,1'-biphenyl]-3-yl)thio)propanoyl)-L-proline (Compound 11), isolated as a white solid: MS (EST) calculated for $C_{21}H_{16}ClF_6NO_3S$ [M+1]$^+$=498.0, found 497.9; $^1$H-NMR (400 MHz, CD$_3$OD) δ 7.90-7.77 (m, 1H), 7.62-7.56 (m, 1H), 4.37-4.12 (m, 2H), 3.72-3.59 (m, 2H), 3.35-1.82 (m, 4H), 1.40-1.37 (m, 3H); $^{19}$F-NMR (376 MHz, CD$_3$OD) δ –112.22, –142.57, –156.09, –164.68; and ((R)-2-((4-chloro-2',3',4',5',6,6'-hexafluoro-[1,1'-biphenyl]-3-yl)thio)propanoyl)-L-proline (Compound 12), isolated as a white solid: MS (ESI) calculated for $C_{21}H_{16}ClF_6NO_3S$ [M+1]$^+$=498.0, found 498.0: $^1$H-NMR (400 MHz, CD$_3$OD) δ 7.90-7.77 (m, 1H), 7.63-7.56 (m, 1H), 4.27-4.20 (m, 1H), 4.06-4.01 (m, 1H), 3.59-3.55 (m, 1H), 3.35-3.30 (m, 1H), 2.12-1.70 (m, 4H), 1.48-1.46 (m, 3H); $^{19}$F-NMR (376 MHz, CD$_3$OD) δ –114.18, –142.72, –156.18, –164.75.

Example 4. Preparation of (S)-2-((2-((4-chloro-2',3',4',5',6,6'-hexafluoro-[1,1'-biphenyl]-3-yl)thio)propanoyl)oxy)ethyl methacrylate (Compound 13) and (R)-2-((2-((4-chloro-2',3',4',5',6,6'-hexafluoro-[1,1'-biphenyl]-3-yl)thio)propanoyl)oxy)ethyl methacrylate (Compound 14)

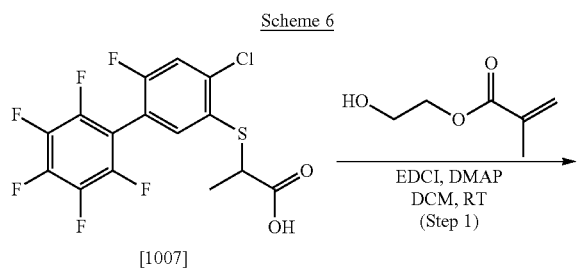

Scheme 6

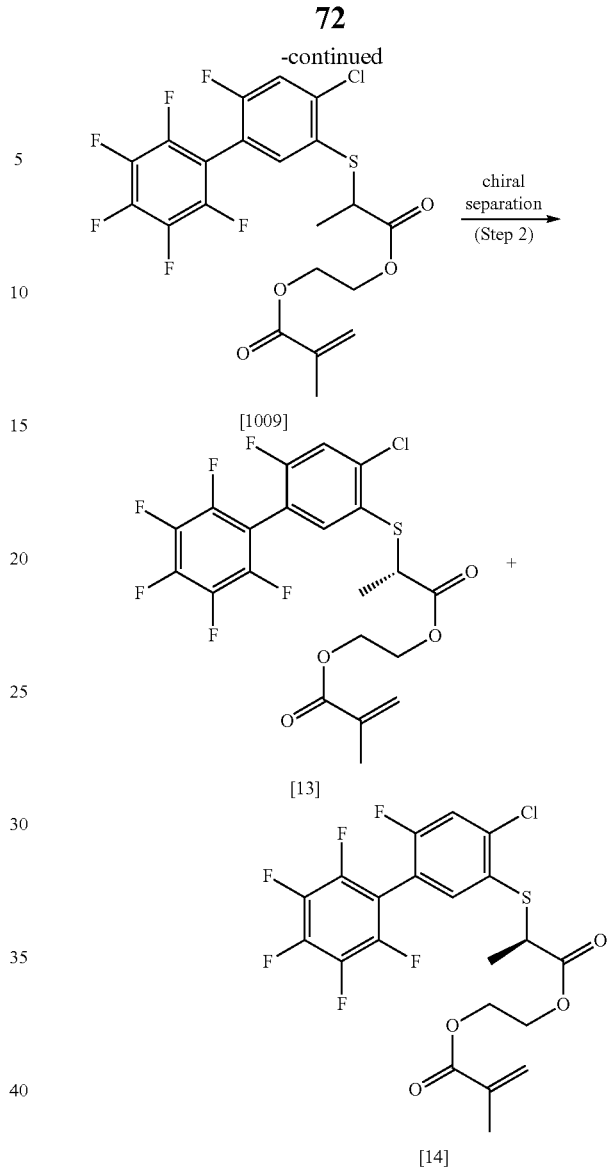

As shown in Step 1 of Scheme 6, to a stirred mixture of 2-((4-choro-2',3',4',5,6,6'-hexafluoro-[1,1'-biphenyl]-3-yl)thio)propanoic acid (180 mg, 0.45 mmol) in DCM (2 mL) were added 2-hydroxyethyl methacrylate (88 mg, 0.67 mmol), 1-ethyl-3-(3-dimethylaminopropyl)-carbodiimide (EDCI, 129 mg, 0.67 mmol), DMAP (55 mg, 0.45 mmol) at 25° C. under a nitrogen atmosphere. The mixture was stirred at 20° C. for 2 hours, diluted with water, and extracted with ethyl acetate. The combined organic layers were washed with brine, dried over anhydrous sodium sulfate, filtered, concentrated under reduced pressure, and purified by preparative-TLC (1:5 EtOAc/petroleum ether) to afford racemic 2-((2-((4-chloro-2',3',4',5',6,6'-hexafluoro-[1,1'-biphenyl]-3-yl)thio)propanoyl)oxy)ethyl methacrylate (Compound 1009, 110 mg, 52% yield) as colorless oil. GCMS calculated for $C_{21}H_{15}ClF_6O_4S$=512.0, found 512.0.

As shown in Step 2 of Scheme 6, racemic 2-((2-((4-chloro-2',3',4',5',6,6'-hexafluoro-[1,1'-biphenyl]-3-yl)thio)propanoyl)oxy)ethyl methacrylate (110 mg) was separated by preparative chiral-HPLC using the following conditions—Column: CHIRALPAK AD-H, 2×25 cm, 5 μm: Mobile Phase 5% EtOH/hexane to afford (S)-2-((2-((4- chloro-2',3',4',5',6,6'-hexafluoro-[1,1'-biphenyl]-3-yl)thio)propanoyl)oxy)ethyl methacrylate (Compound 13, 47 mg, 30% yield) as colorless oil: GCMS calculated for $(C_{21}H_{15}ClF_6O_4S)=512.0$, found 512.0; $^1$H-NMR (400 MHz, methanol-d$_4$) δ 7.76 (d, J=7.2 Hz, 1H), 7.58 (d, J=9.2 Hz, 1H), 6.04 (s, 1H), 5.64-5.58 (m, 1H), 4.36-4.28 (m, 2H), 4.30-4.19 (m, 2H), 4.09-3.99 (m, 1H), 1.90 (s, 3H), 1.52 (d, J=7.2 Hz, 3H); $^{19}$F-NMR (376 MHz, methanol-d$_4$) δ −112.74, −142.42, −156.16, −164.62. Also recovered as the second eluting peak was (R)-2-((2-((4-chloro-2',3',4',5',6,6'-hexafluoro-[1,1'-biphenyl]-3-yl)thio)propanoyl)oxy)-ethyl methacrylate (Compound 14, 46 mg, 29% yield) as colorless oil: GCMS calculated for $C_{21}H_{15}ClF_6O_4S=512.0$, found 512.0; $^1$H-NMR (400 MHz, methanol-d$_4$) δ 7.76 (d, J=7.2 Hz, 1H), 7.58 (d, J=9.2 Hz, 1H), 6.04 (s, 1H), 5.64-5.58 (m, 1H), 4.36-4.28 (m, 2H), 4.30-4.19 (m, 2H), 4.09-3.99 (m, 1H), 1.90 (s, 3H), 1.52 (d, J=7.2 Hz, 3H); $^{19}$F-NMR (376 MHz, methanol-d$_4$) δ −112.74, −142.42, −156.16, −164.62.

Example 5. Preparation of 4-chloro-2',3',4',5',6,6'-hexafluoro-[1,1'-biphenyl]-3-sulfonamide (Compound 15)

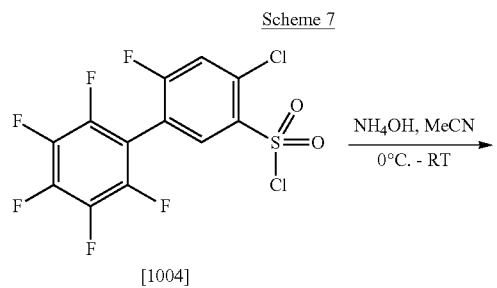

As shown in Scheme 7, to a stirred mixture of 4-chloro-2',3',4',5',6,6'-hexafluoro-[1,1'-biphenyl]-3-sulfonyl chloride (100 mg, 0.50 mmol) in MeCN (2 mL) was added NH$_4$OH (0.2 mL). The mixture was stirred at 20° C. for 16 hours under a nitrogen atmosphere, diluted with water, and extracted with ethyl acetate. The combined organic layers were washed with brine, dried over anhydrous sodium sulfate, filtered, concentrated under reduced pressure, and purified by reversed-phase flash chromatography (5%-45% acetonitrile in water) to afford 4-chloro-2',3',4',5',6,6'-hexafluoro-[1,1'-biphenyl]-3-sulfonamide (Compound 15, 11 mg, 10% yield) as a white solid: MS (ESI) calculated for $C_{12}H_4ClF_6NO_2S$ [M−1]$^−$=374.0, found 373.9; $^1$H-NMR (400 MHz, DMSO-d$_6$) δ 8.20 (d, J=7.2 Hz, 1H), 8.07-7.99 (m, 1H), 7.87 (s, 2H); $^{19}$F-NMR (376 MHz, DMSO-d$_6$) δ −106.35, −140.80, −152.86, −161.83.

Example 6. Preparation of 4-chloro-N-(dimethylcarbamoyl)-2',3',4',5',6,6'-hexafluoro-[1,1'-biphenyl]-3-sulfonamide (Compound 16)

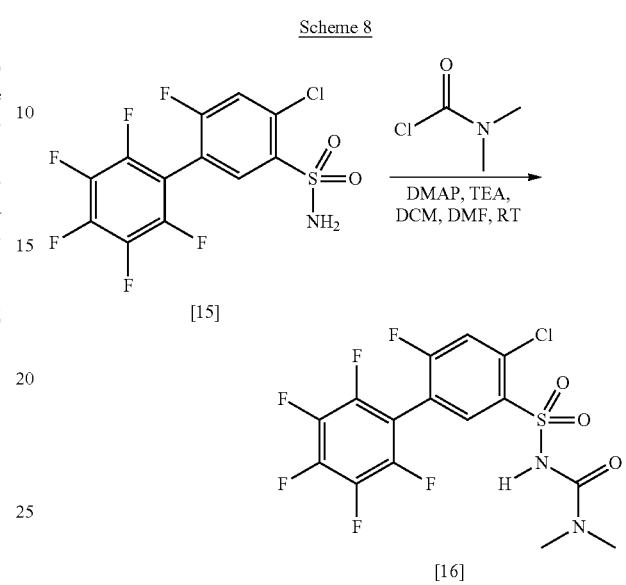

As shown in Scheme 8, to a stirred mixture of 4-chloro-2',3',4',5',6,6'-hexafluoro-[1,1'-biphenyl]-3-sulfonamide (40 mg, 0.10 mmol) in DCM (1 mL) and DMF (0.3 mL) were added TEA (32 mg, 0.30 mmol), DMAP (1 mg, 0.01 mmol) and dimethylcarbamic chloride (17 mg, 0.15 mmol). The resulting mixture was stirred at 25° C. for 2 hours under a nitrogen atmosphere, diluted with water, and extracted with ethyl acetate. The combined organic layers were washed with brine, dried over anhydrous sodium sulfate, filtered, concentrated under reduced pressure, and purified by reversed-phase flash chromatography (5%-50% acetonitrile in water) to afford 4-chloro-N-(dimethylcarbamoyl)-2',3',4',5',6,6'-hexafluoro-[1,1'-biphenyl]-3-sulfonamide (Compound 16, 21 mg, 44% yield) as a white solid: MS (ESI) calculated for $C_{15}H_9ClF_6N_2O_3S$ [M−1]$^−$=446.9, found 447.1; $^1$H-NMR (400 MHz, DMSO-d$_6$) δ 11.38 (s, 1H), 8.22 (d, J=7.2 Hz, 1H), 7.96 (d, J=9.2 Hz, 1H), 2.83 (s, 6H); $^{19}$F-NMR (376 MHz, DMSO-d$_6$) δ −106.01, −140.55, −152.99, −161.91.

Using the appropriate acyl chloride, carbamic chloride or carbonochloridate in a transformation similar to that described to prepare 4-chloro-N-(dimethylcarbamoyl)-2',3',4',5',6,6'-hexafluoro-[1,1'-biphenyl]-3-sulfonamide, the following compounds were also prepared:

N-((4-chloro-2',3',4',5',6,6'-hexafluoro-[1,1'-biphenyl]-3-yl)sulfonyl)acetamide (Compound 17), isolated as a white solid: MS (ESI) calculated for $C_{14}H_6ClF_6NO_3S$ [M+1]$^+$= 417.9. found 417.9; $^1$H-NMR (400 MHz, DMSO-d$_6$) δ 12.72 (s, 1H), 8.32 (d, J=7.2 Hz, 1H), 8.07 (d, J=9.2 Hz, 1H), 2.00 (s, 3H); $^{19}$F-NMR (377 MHz, DMSO-d$_6$) δ −103.56, −140.52, −152.82, −161.91;

N-((4-chloro-2',3',4',5',6,6'-hexafluoro-[1,1'-biphenyl]-3-yl)sulfonyl)propionamide (Compound 18), isolated as a white solid: MS (ESI) calculated for $C_{15}H_8ClF_6NO_3S$ [M−1]$^−$=429.9, found 429.9; $^1$H-NMR (400 MHz, DMSO-d$_6$) δ 12.67 (s, 1H), 8.33 (d, J=7.2 Hz, 1H), 8.08 (d, J=9.6 Hz, 1H), 2.30 (q, J=7.2 Hz, 2H), 1.08-0.75 (t, J=7.2 Hz, 3H); $^{19}$F-NMR (377 MHz, DMSO-d$_6$) δ −103.40, −140.48, −152.79, −161.89;

N-((4-chloro-2',3',4',5',6,6'-hexafluoro-[1,1'-biphenyl]-3-yl)sulfonyl)isobutyramide (Compound 19), isolated as a white solid: MS (ESI) calculated for $C_{16}H_{10}ClF_6NO_3S$ $[M+1]^+$=446.0, found 446.0; $^1$H-NMR (400 MHz, DMSO-$d_6$) δ 12.68 (s, 1H), 8.31 (d, J=7.2 Hz, 1H), 8.06 (d, J=9.2 Hz, 1H), 2.55 (d, J=7.2 Hz, 1H), 0.99 (d, J=6.8 Hz, 6H); $^{19}$F-NMR (377 MHz, DMSO-$d_6$) δ −103.23, −140.65, −152.27, −161.58;

N-((4-chloro-2',3',4',5',6,6'-hexafluoro-[1,1'-biphenyl]-3-yl)sulfonyl)-3-methylbutanamide (Compound 20), isolated as a white solid: MS (ESI) calculated for $C_7H_{12}ClF_6NO_3S$ $[M-1]^-$=458.0, found 457.9; $^1$H-NMR (400 MHz, DMSO-$d_6$) δ 12.66 (s, 1H), 8.34 (d, J=7.2 Hz, 1H), 8.08 (d, J=9.2 Hz, 1H), 2.16 (d, J=7.2 Hz, 2H), 1.94-1.90 (m, 1H), 0.82 (d, J=6.4 Hz, 6H); $^{19}$F-NMR (400 MHz, DMSO-$d_6$) δ −103.34, −140.47, −152.83, −161.91;

N-((4-chloro-2',3',4',5',6,6'-hexafluoro-[1,1'-biphenyl]-3-yl)sulfonyl)-2-phenylacetamide (Compound 21), MS (ESI) calculated for $C_{20}H_{10}ClF_6NO_3S$ $[M+1]^+$=494.0, found 494.0; $^1$H-NMR (400 MHz, DMSO-$d_6$) δ 12.97 (s, 1H), 8.29 (d, J=7.2 Hz, 1H), 8.06 (d, J=9.2 Hz, 1H), 7.40-7.03 (m, 5H), 3.64 (s, 2H); $^{19}$F-NMR (376 MHz, DMSO-$d_6$) δ −103.24, −140.46, −152.78, −161.90;

methyl ((4-chloro-2',3',4',5',6,6'-hexafluoro-[1,1'-biphenyl]-3-yl)sulfonyl)carbamate (Compound 22), MS (ESI) calculated for $C_{14}H_6ClF_6NO_4S$ $[M+1]^+$=431.9, found 431.9; $^1$H-NMR (400 MHz, DMSO-$d_6$) δ 12.79 (s, 2H), 8.32 (d, J=7.2 Hz, 1H), 8.07 (d, J=9.2 Hz, 1H), 3.59 (s, 3H); $^{19}$F-NMR (376 MHz, DMSO-$d_6$) δ −103.50, −140.55, −152.83, −161.90; and N-((4-chloro-2',3',4',5',6,6'-hexafluoro-[1,1'-biphenyl]-3-yl)sulfonyl)benzamide (Compound 23), MS (ESI) calculated for $C_{19}H_8ClF_6NO_3S$ $[M-1]^-$=477.9, found 477.8; $^1$H-NMR (400 MHz, DMSO-$d_6$) δ 8.42 (d, J=7.2 Hz, 1H), 8.05 (d, J=9.2 Hz, 1H), 7.96-7.89 (m, 2H), 7.65 (t, J=7.4 Hz, 1H), 7.53-7.49 (m, 2H); $^{19}$F-NMR (376 MHz, DMSO-$d_6$) δ −103.60, −140.43, −152.82, −161.89.

Example 7. Synthesis of N-((4-chloro-2',3',4',5',6,6'-hexafluoro-[1,1'-biphenyl]-3-yl)sulfonyl)-2,2,2-trifluoroacetamide (Compound 24)

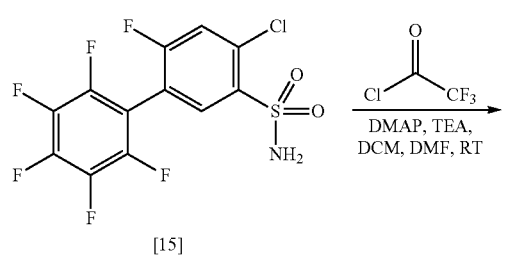

Scheme 9

To a stirred mixture of 2,2,2-trifluoroacetic acid (35.2 mg, 0.26 mmol) in THF (1 mL) were sequentially added $SOCl_2$ (284.99 mg, 2.39 mmol) and TEA (53.8 mg, 0.53 mmol) at 0° C. under nitrogen atmosphere and the mixture stirred at 50° C. for 4 hours before concentration under reduced pressure. The resulting acyl chloride was dissolved in DCM (1 mL) was added to a solution of 4-chloro-2',3',4',5',6,6'-hexafluoro-[1,1'-biphenyl]-3-sulfonamide (Compound 15, 100 mg, 0.26 mmol), TEA (53 mg, 0.52 mmol), and DMAP (3 mg, 0.03 mmol) in DCM (1 mL) at 0° C. The resulting mixture was then stirred at 20° C. for 2 hours. The mixture was quenched by the addition of water. The aqueous layer was extracted with ethyl acetate. The combined organic solution was dried over sodium sulfate, filtered, and concentrated under vacuum. The residue was purified by reversed-phase flash column chromatography with the following conditions (5% to 50% MeCN in Water (0.1% FA) to afford N-((4-chloro-2',3',4',5',6,6'-hexafluoro-[1,1'-biphenyl]-3-yl) sulfonyl)-2,2,2-trifluoroacetamide (Compound 24, 39 mg, 9% yield, 82.7% purity on LCMS) as a light yellow solid: MS (ESI) calculated for $C_{14}H_3ClF_9NO_3S$ $[M-1]^-$=470.0, found 469.9. $^1$H-NMR (400 MHz, chloroform-d) δ 8.39 (d, J=7.2 Hz, 1H), 7.54 (d, J=9.2 Hz, 1H); $^{19}$F-NMR (376 MHz, Chloroform-d) δ −75.51, −98.37, −139.14, −150.54, −160.29.

The ammonium salt of Compound 24 was formed by applying it to a preparative reversed-phase HPLC column and eluting the column using the following conditions: (Mobile Phase A: water (10 mmol/L $NH_3H_2O$); Mobile Phase B: ACN; Gradient: 30% B to 40% B over 10 min, then 40% B over 14 min) to afford N-((4-chloro-2',3',4',5',6,6'-hexafluoro-[1,1'-biphenyl]-3-yl)sulfonyl)-2,2,2-trifluoroacetamide, ammonium salt (2.8 mg, 21% yield) as a yellow solid: MS (ESI) calculated for $C_{14}H_3ClF_9NO_3S$ $[M-1]^-$= 470.0, found, 469.9. $^1$H NMR (400 MHz, methanol-$d_4$) δ 8.26 (d, J=7.2 Hz, 1H), 7.59 (d, J=9.2 Hz, 1H). $^{19}$F NMR (376 MHz, methanol-$d_4$) δ −77.03, −108.86, −142.23, −155.98, −164.71.

The sodium salt of Compound 24 was formed by treatment with NaOH (0.1 N, 0.2 mL). Washing the aqueous solution with ethyl ether and lyophilization afforded N-{4-chloro-2',3',4',5',6,6'-hexafluoro-[1,1'-biphenyl]-3-ylsulfonyl}-2,2,2-trifluoroacetamide, sodium salt (2.4 mg, 24% yield) as a light yellow solid: MS (ESI) calculated for $C_{14}H_3ClF_9NO_3S$ $[M-1]^-$=470.0, found 469.9: $^1$H-NMR (400 MHz, Methanol-$d_4$) δ 8.24 (d, J=7.2 Hz, 1H), 7.59 (d, J=9.2 Hz, 1H); $^{19}$F-NMR (376 MHz, Methanol-$d_4$) δ −76.80, −108.30, −142.23, −155.42, −164.27.

Example 8. Preparation of 4-chloro-2',3',4',6,6'-pentafluoro-[1,1'-biphenyl]-3-sulfonamide (Compound 25) and N-((4-chloro-2',3',4',6,6'-pentafluoro-[1,1'-biphenyl]-3-yl)sulfonyl)propionamide (Compound 26)

Scheme 10

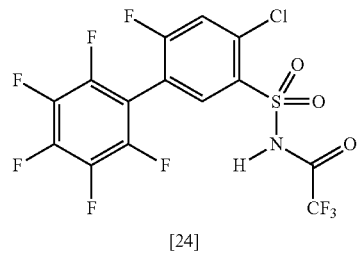

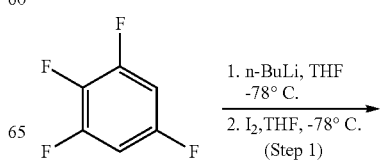

1. n-BuLi, THF -78° C.
2. $I_2$, THF, -78° C.
(Step 1)

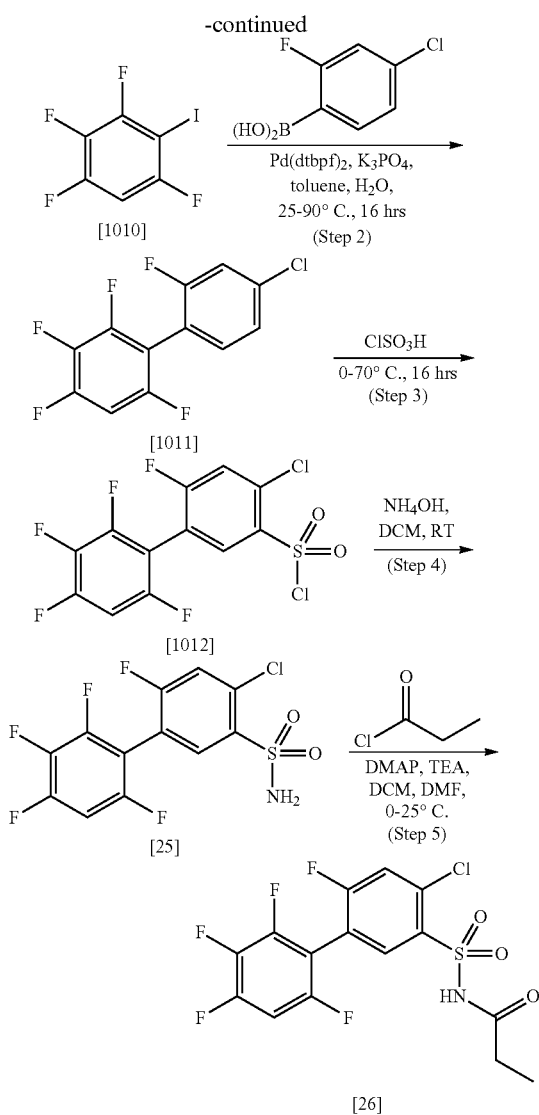

As shown in Step 1 of Scheme 10, To a solution of 1,2,3,5-tetrafluorobenzene (80.0 g, 533 mmol, 1.0 eq) in THF (400 mL) at −78° C. was added n-BuLi dropwise (2.5 M, 213 mL, 1.0 equiv.). After addition, the mixture was stirred at −78° C. for 1 hour, followed by addition of a solution 12 (135 g, 533 mmol, 107 mL, 1.0 equiv.) in THF (400 mL). The mixture was stirred at −78° C. for 1 hour and poured into a sat'd NH$_4$Cl solution (1.50 L). The mixture was extracted with EtOAc (800 mL×2), brine (1.0 L×2), and dried over Na$_2$SO$_4$. After filtration, the organics were concentrated under reduced pressure to yield 1,2,3,5-tetrafluoro-4-iodobenzene (Compound 1010) a brown oil. This material was used directly as is in subsequent reactions without further purification.

As shown in Step 2 of Scheme 10, to a solution of 1,2,3,5-tetrafluoro-4-iodobenzene (130 g, 471 mmol, 1.0 equiv.), (4-chloro-2-fluorophenyl)boronic acid (90.3 g, 518 mmol, 1.1 eq) and K$_3$PO$_4$ (200 g, 942 mmol, 2.0 eq) in toluene (1.30 L) and H$_2$O (260 mL) was added Pd(dtbpf)$_2$ (6.14 g, 9.42 mmol, 0.02 eq) at 25° C. The mixture was stirred at 90° C. for 16 hours, followed by addition to water (500 mL). The mixture was extracted with ethyl acetate (500 mL×2) and the combined organics washed with brine (500 mL×2), dried over Na$_2$SO$_4$, concentrated under reduced pressure, and purified by flash chromatography (1-2% petroleum ether/EtOAc) to give 4'-chloro-2,2',3,4,6-pentafluoro-1,1'-biphenyl as a colorless oil (Compound 1011, 130 g): $^1$H-NMR (400 MHz, DMSO-d$_6$) δ 7.67-7.65 (m, 1H), 7.58-7.48 (m, 2H), 7.16-7.12 (m, 1H).

As shown in Step 3 of Scheme 10, 4'-chloro-2,2',3,4,6-pentafluoro-1,1'-biphenyl (Compound 1011, 130 g, 466 mmol, 1.0 eq) was slowly added into ClSO$_3$H (544 g, 4.67 mol, 311 mL, 10 eq) at 0° C. in portions. The mixture was stirred at 70° C. for 16 hours and poured into ice water (1 L) and extracted with ethyl acetate (500 mL×3). The combined organics were washed with brine (1 L×2), dried over Na$_2$SO$_4$, filtered, concentrated under reduced pressure, and purified by flash chromatography (1-2% petroleum ether/EtOAc) to provide 4-chloro-2',3',4',6,6'-pentafluoro-[1,1'-biphenyl]-3-sulfonyl chloride (Compound 1012, 90 g, 238 mmol, 51% yield from Compound 1010) as a yellow solid: $^1$H-NMR δ 7.98-7.96 (m, 1H), 7.69-7.67 (m, 1H), 7.63-7.58 (m, 1H).

As shown in Step 4 of Scheme 10, to a solution of 4-chloro-2',3',4',6,6'-pentafluoro-[1,1'-biphenyl]-3-sulfonyl chloride (90 g, 238 mmol, 1.0 eq) in DCM (900 mL) was added 28% NH$_4$OH (328 mL, 2.39 mol, 10.0 eq) and the mixture was stirred at 25° C. for 1 hour. The mixture was diluted with 1 L of water extracted with DCM (800 mL×2). The combined organics were washed with brine (1 L×2), dried over Na$_2$SO$_4$, concentrated under reduced pressure, and triturated with petroleum ether (1 L) for 30 minutes to provide 4-chloro-2',3',4',6,6'-pentafluoro-[1,1'-biphenyl]-3-sulfonamide (Compound 25, 77.0 g, 209 mmol, 88% yield) as a white solid: MS (ESI) calculated for C$_{12}$H$_5$ClF$_5$NO$_2$S [M−1]$^-$=356.0, found 355.9; $^1$H-NMR (400 MHz, DMSO-d$_6$) δ 8.15 (d, J=7.2 Hz, 1H), 7.95-7.82 (m, 1H), 7.77 (s, 2H), 7.75-7.72 (m, 1H).

As shown in Step 5 of Scheme 10, to a solution of 4-chloro-2',3',4',6,6'-pentafluoro-[1,1'-biphenyl]-3-sulfonamide (35.0 g, 97.8 mmol, 1.0 eq) in DCM (350 mL) and DMF (90.0 mL) was added TEA (19.8 g, 196 mmol, 27.2 mL, 2.00 eq) and DMAP (1.20 g, 9.79 mmol, 0.1 eq) at 25° C. The mixture was cooled to 0° C. and propionyl chloride (13.6 g, 146 mmol, 13.6 mL, 1.5 eq) was added, followed by stirring the reaction mixture at 25° C. for 1 hour. The mixture was then diluted with H$_2$O (500 mL) and extracted with DCM (500 mL×2). The combined organics were washed with brine (500 mL×2), dried over Na$_2$SO$_4$, concentrated under reduced pressure, and purified by reversed-phase flash chromatography (50% to 80% acetonitrile/H$_2$O (0.1% FA). After concentrating the fractions containing product under reduced pressure, the residue was triturated with EtOH (150 mL) at 25° C. for 16 hours to provide N-((4-chloro-2',3',4',6,6'-pentafluoro-[1,1'-biphenyl]-3-yl)sulfonyl)propionamide (Compound 26, 25.4 g, 63% yield) as a white solid: MS (ESI) calculated for C$_{15}$H$_9$ClF$_5$NO$_3$S [M−1]$^-$=412.0, found 412.0; $^1$H-NMR (400 MHz, DMSO-d$_6$) δ 12.6 (brs, 1H), 8.29 (d, J=7.6 Hz, 1H), 7.79 (d, J=4.4 Hz, 1H), 7.75-7.73 (m, 1H), 2.33-2.22 (m, 2H), 0.95-0.86 (m, 3H).

Using the appropriate acyl chloride, carbamic chloride, anhydride, or carbonochloridate in transformations similar to those described for Step 5 of Scheme 10 in Example 8, the following compounds were also prepared:

N-((4-chloro-2',3',4',6,6'-pentafluoro-[1,1'-biphenyl]-3-yl)sulfonyl)acetamide (Compound 27), isolated as a white solid: MS (ESI) calculated for (C$_{14}$H$_7$ClF$_5$NO$_3$S) [M−1]$^-$, 398.0; found, 397.9; $^1$H-NMR (400 MHz, DMSO-d$_6$) δ 12.67 (s, 1H), 8.27 (d, J=7.2 Hz, 1H), 8.02 (d, J=8.8 Hz, 1H), 7.78-7.72 (m, 1H), 1.99 (s, 3H); $^{19}$F-NMR (377 MHz, DMSO-d$_6$) δ −103.84, −115.57, −130.71, −133.56, −164.64;

N-((4-chloro-2',3',4',6,6'-pentafluoro-[1,1'-biphenyl]-3-yl)sulfonyl)tetrahydro-2H-pyran-4-carboxamide (Compound 28), isolated as a white sold: MS (ESI) calculated for (C$_{18}$H$_{13}$ClF$_5$NO$_4$S) [M−1]$^-$=468.0, found 467.9; $^1$H-NMR (400 MHz, DMSO-d$_6$) δ 12.70 (s, 1H), 8.28 (d, J=7.2 Hz, 1H), 8.03 (d, J=9.2 Hz, 1H), 7.82-7.71 (m, 1H), 3.83-3.81 (m, 2H), 3.32-3.22 (m, 2H), 2.68-2.60 (m, 1H), 1.69-1.65 (m, 2H), 1.51-1.37 (m, 2H); $^{19}$F-NMR (376 MHz, DMSO-d$_4$) δ −103.53, −115.50, −130.93, −133.67, −164.63;

N-((4-chloro-2',3',4',6,6'-pentafluoro-[1,1'-biphenyl]-3-yl)sulfonyl)-2-(4-chlorophenyl)acetamide (Compound 29), isolated as white solid: MS (ESI) calculated for (C$_{20}$H$_{10}$Cl$_2$F$_5$NO$_3$S) [M+1]$^+$=507.9, found, 507.9; $^1$H-NMR (400 MHz, DMSO-d$_6$) δ 12.97 (s, 1H), 8.23 (d, J=7.2 Hz, 1H), 8.01 (d, J=9.6 Hz, 1H), 7.81-7.69 (m, 1H), 7.40-7.32 (m, 2H), 7.26-7.19 (m, 2H), 3.64 (s, 2H); $^{19}$F-NMR (376 MHz, DMSO-d$_6$) δ −103.53, −115.50, −130.63, −133.42, −164.52;

2-chloro-N-((4-chloro-2',3',4',6,6'-pentafluoro-[1,1'-biphenyl]-3-yl)sulfonyl)benzamide (Compound 30), isolated as white solid: MS (ESI) calculated for (C$_{18}$H$_{10}$Cl$_2$F$_5$NO$_3$S) [M−1]$^-$=493.9, found 493.8: $^1$H-NMR (400 MHz, DMSO-d$_6$) δ 8.31 (d, J=7.2 Hz, 1H), 8.01 (d, J=9.2 Hz, 1H), 7.86-7.66 (m, 1H), 7.51-7.36 (m, 4H); $^{19}$F-NMR (376 MHz, DMSO-d$_6$) δ −103.52, −115.45, −130.62, −133.53, −164.58;

4-chloro-N-((4-chloro-2',3',4',6,6'-pentafluoro-[1,1'-biphenyl]-3-yl)sulfonyl)benzamide (Compound 31), isolated as a white solid: MS (ESI) calculated for (C$_{19}$H$_8$Cl$_2$F$_5$NO$_3$S) [M−1]$^-$=493.9, found 493.9; $^1$H-NMR (400 MHz, DMSO-d$_6$) δ 8.33 (d, J=7.2 Hz, 1H), 8.03-7.86 (m, 3H), 7.82-7.66 (m, 1H), 7.64-7.48 (m, 2H); $^{19}$F-NMR (376 MHz, DMSO-d$_6$) δ −103.56, −115.45, −130.75, −133.46, −164.58;

3-chloro-N-((4-chloro-2',3',4',6,6'-pentafluoro-[1,1'-biphenyl]-3-yl)sulfonyl)benzamide (Compound 32), isolated as white solid: MS (EST) calculated for (C$_{19}$H$_8$Cl$_2$F$_5$NO$_3$S) [M−1]$^-$=493.9, found 493.9; $^1$H-NMR (400 MHz, DMSO-d$_6$) δ 8.34 (d, J=7.2 Hz, 1H), 8.03-7.89 (m, 2H), 7.86 (dt, J=7.6, 1.2 Hz, 1H), 7.82-7.72 (m, 1H), 7.68 (dd, J=7.6, 2.0 Hz, 1H), 7.52 (t, J=8.0 Hz, 1H); $^{19}$F-NMR (376 MHz, DMSO-d$_6$) δ −103.58, −115.44, −130.74, −133.46, −164.52;

phenyl ((4-chloro-2',3',4',6,6'-pentafluoro-[1,1'-biphenyl]-3-yl)sulfonyl)carbamate (Compound 33), isolated as white solid: MS (ESI) calculated for (C$_{19}$H$_9$ClF$_5$NO$_4$S) [M−1]$^-$=475.9, found 475.9; $^1$H-NMR (400 MHz, DMSO-d$_6$) δ 8.03 (d, J=7.6 Hz, 1H), 7.77-7.65 (m, 2H), 7.31-7.22 (m, 2H), 7.06 (t, J=7.2 Hz, 1H), 6.94-6.87 (m, 2H); $^{19}$F-NMR (376 MHz, DMSO-d$_6$) δ −110.34, −115.54, −131.31, −133.74, −164.61;

4-((4-chloro-2',3',4',6,6'-pentafluoro-[1,1'-biphenyl])-3-sulfonamido)-4-oxobutanoic acid (Compound 55), from dihydrofuran-2,5-dione, isolated as white solid: MS (EST) calc'd for C$_{16}$H$_9$ClF$_5$NO$_5$S [M−1]$^-$=456.0; found, 455.9; $^1$H-NMR (400 MHz, CD$_3$OD) δ 8.29 (d, J=7.6 Hz, 1H), 7.68 (d, J=9.2 Hz, 1H), 7.34-7.27 (m, 1H), 2.63-2.59 (m, 2H), 2.55-2.52 (m, 2H); $^{19}$F-NMR (377 MHz, DMSO-d$_6$) δ −105.09, −116.93, −132.45, −135.08, −167.38; after treatment of Compound 55 with acetic anhydride and triethylamine in DMF at room temperature, 1-((4-chloro-2',3',4',6,6'-pentafluoro-[1,1'-biphenyl]-3-yl)sulfonyl)pyrrolidine-2,5-dione (Compound 70): MS (EST) calc'd for C$_{16}$H$_7$ClF$_5$NO$_4$S [M−1]$^-$=438.0, found 437.9; $^1$H-NMR (400 MHz, DMSO-d$_6$) δ 8.40 (d, J=6.8 Hz, 1H), 8.13 (d, J=9.2 Hz, 1H), 7.80-7.74 (m, 1H), 2.81 (s, 4H); $^{19}$F-NMR (377 MHz, DMSO-d$_6$) δ −101.42, −115.45, −130.48, −133.46, −164.66;

N-((4-chloro-2',3',4',6,6'-pentafluoro-[1,1'-biphenyl]-3-yl)sulfonyl)butyramide (Compound 56), isolated as white solid: MS (EST) calc'd for C$_{16}$H$_{11}$ClF$_5$NO$_3$S [M−1]$^-$=426.0, found 425.9; $^1$H-NMR (400 MHz, DMSO-d$_6$) δ 12.64 (br, 1H), 8.28 (d, J=7.2 Hz, 1H), 8.03 (d, J=9.2 Hz, 1H), 7.79-7.72 (m, 1H), 2.26 (t, J=7.2 Hz, 2H), 1.51-1.52 (m, 2H), 0.95 (t, J=7.2 Hz, 3H); $^{19}$F-NMR (377 MHz, DMSO-d$_6$) δ −103.66, −115.56, −130.70, −133.55, −164.66;

N-((4-chloro-2',3',4',6,6'-pentafluoro-[1,1'-biphenyl]-3-yl)sulfonyl)isobutyramide (Compound 59), isolated as white solid: MS (ESI) calc'd for C$_{16}$H$_{11}$ClF$_5$NO$_3$S [M−1]$^-$=466.0, found 428.9; $^1$H-NMR (400 MHz, DMSO-d$_6$) δ 12.62 (br, 1H), 8.27 (d, J=7.2 Hz, 1H), 8.02 (d, J=9.2 Hz, 1H), 7.78-7.72 (m, 1H), 2.59-2.54 (m, 1H), 1.00 (d, J=6.8 Hz, 6H); $^{19}$F-NMR (377 MHz, DMSO-d$_6$) δ −103.52, −115.52, −130.43, −133.54, −164.66;

N-((4-chloro-2',3',4',6,6'-pentafluoro-[1,1'-biphenyl]-3-yl)sulfonyl)pivalamide (Compound 63), isolated as white solid: MS (ESI) calc'd for C$_{17}$H$_{13}$ClF$_5$NO$_3$S [M+1]$^+$=442.0, found 442.0; $^1$H-NMR (400 MHz, DMSO-d$_6$) δ 12.27 (br, 1H), 8.26 (d, J=7.2 Hz, 1H), 8.00 (d, J=9.6 Hz, 1H), 7.78-7.72 (m, 1H), 1.13 (s, 9H); $^{19}$F-NMR (377 MHz, DMSO-d$_6$) δ −103.61, −115.49, −131.64, −133.52, −164.65:

N-((4-chloro-2',3',4',6,6'-pentafluoro-[1,1'-biphenyl]-3-yl)sulfonyl)-3,3-dimethylbutanamide (Compound 64), isolated as white solid: MS (ESI) calc'd for C$_{18}$H$_{15}$ClF$_5$NO$_3$S [M−1]$^-$=454.0, found 454.0; $^1$H-NMR (400 MHz, DMSO-d$_6$) δ 12.55 (br, 1H), 8.29 (d, J=7.2 Hz, 1H), 8.03 (d, J=9.2 Hz, 1H), 7.78-7.72 (m, 1H), 2.15 (s, 2H), 0.90 (s, 9H); $^{19}$F-NMR (377 MHz, DMSO-d$_6$) δ −103.62, −115.59, −130.71, −133.57, −164.69;

4-chloro-N-(dimethylcarbamoyl)-2',3',4',6,6'-pentafluoro-[1,1'-biphenyl]-3-sulfonamide (Compound 66), isolated as white solid: MS (EST) calc'd for C$_{15}$H$_{10}$ClF$_5$N$_2$O$_3$S [M+1]$^+$=429.0, found 429.0; $^1$H-NMR (400 MHz, DMSO-d$_6$) δ 8.07 (d, J=7.2 Hz, 1H), 7.73-7.69 (m, 2H), 2.68 (s, 6H); $^{19}$F-NMR (377 MHz, DMSO-d$_6$) δ −103.50, −115.49, −130.98, −133.63, −164.64;

N-((4-chloro-2',3',4',6,6'-pentafluoro-[1,1'-biphenyl]-3-yl)sulfonyl)methacrylamide (Compound 75), isolated as white solid: MS (ESI) calc'd for C$_{16}$H$_9$ClF$_5$NO$_3$S [M+1]$^+$=426.0, found 426.0; $^1$H-NMR (400 MHz, DMSO-d$_6$) δ 12.69 (br, 1H), 8.30 (d, J=7.2 Hz, 1H), 8.01 (d, J=9.2 Hz, 1H), 7.80-7.73 (m, 1H), 6.05 (s, 1H), 5.75 (s, 1H), 1.77 (s, 3H); $^{19}$F-NMR (377 MHz, DMSO-d$_6$) δ −103.59, −115.51, −130.71, −133.48, −164.64; and after treatment of Compound 75 with osmium tetroxide and sodium periodate in THF/water at 0° C., N-((4-chloro-2',3',4',6,6'-pentafluoro-[1,1'-biphenyl]-3-yl)sulfonyl)-2-oxopropanamide (Compound 77): MS (ESI) calc'd for C$_{15}$H$_7$ClF$_5$NO$_4$S [M−1]$^-$=426.0, found 425.9; $^1$H-NMR (400 MHz, DMSO-d$_6$) δ 8.28-8.26 (m, 1H), 7.98-7.82 (m, 1H), 7.77-7.73 (m, 1H), 2.25 (s, 3H); $^{19}$F-NMR (377 MHz, DMSO-4) δ −103.66, −115.48, −130.81, −133.55, −164.60.

Example 9. Preparation of ethyl ((4-chloro-2',3',4',6,6'-pentafluoro-[1,1'-biphenyl]-3-yl)sulfonyl)carbamate (Compound 34) and N-((4-chloro-2',3',4',6,6'-pentafluoro-[1,1'-biphenyl]-3-yl)sulfonyl)-4-hydroxypiperidine-1-carboxamide (Compound 35)

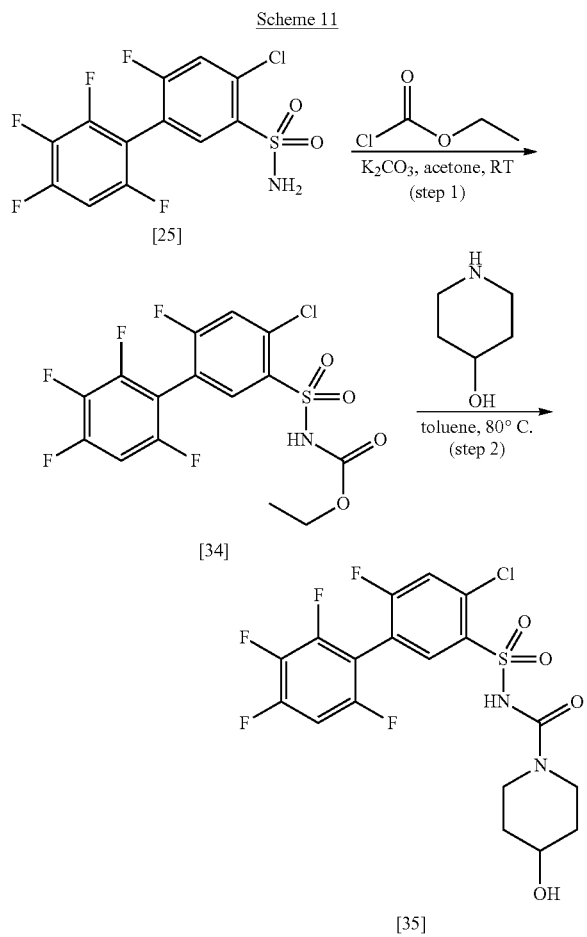

As shown in Step 1 of Scheme 11, to a stirred solution of 4-chloro-2',3',4',6,6'-pentafluoro-[1,1'-biphenyl]-3-sulfonamide (100 mg, 0.28 mmol) and $K_2CO_3$ (77 mg, 0.56 mmol) in acetone (2 mL) was added ethyl chloroformate (61 mg, 0.56 mmol). The resulting mixture was stirred at 25° C. for 16 hours. The reaction diluted with water and extracted with EtOAc. The organic layer was washed by HCl (aq., 0.5 N), dried over anhydrous sodium sulfate, filtered, concentrated under reduced pressure, and purified by reversed-phase preparative HPLC (25% to 50% acetonitrile/water) to afford ethyl ((4-chloro-2',3',4',6,6'-pentafluoro-[1,1'-biphenyl]-3-yl)sulfonyl)carbamate (Compound 34, 8.2 mg, 7% yield) as a white solid: MS (ESI) calculated for $C_{15}H_9ClF_5NO_4S$ [M-1]$^-$=427.9, found 427.9: $^1$H-NMR (400 MHz, DMSO-$d_6$) δ 8.19-8.13 (m, 1H), 7.96-7.89 (m, 1H), 7.86-7.57 (m, 1H), 3.93 (q, J=7.2 Hz, 2H), 1.07-0.94 (m, 3H); $^{19}$F-NMR (376 MHz, DMSO-$d_6$) δ -103.58, -115.71, -130.72, -133.73, -164.59.

As shown in Step 2 of Scheme 11, to a stirred solution of ethyl ((4-chloro-2',3',4',6,6'-pentafluoro-[1,1'-biphenyl]-3-yl)sulfonyl)carbamate (100 mg, 0.23 mmol) in toluene (2 mL) was added piperidin-4-ol (47 mg, 0.47 mmol). The resulting mixture was stirred at 80° C. for 16 hours, then concentrated under reduced pressure. The crude product was purified by reversed-phase preparative HPLC (65% to 75% acetonitrile/water) to afford N-((4-chloro-2',3',4',6,6'-pentafluoro-[1,1'-biphenyl]-3-yl)sulfonyl)-4-hydroxypiperidine-1-carboxamide (Compound 35, 5.5 mg, 5% yield) as a white solid: MS (ESI) calculated for $C_{18}H_{14}ClF_5N_2O_4S$ [M+1]$^+$=485.0, found 485.0; $^1$H-NMR (400 MHz, DMSO-$d_4$) δ 11.43 (s, 1H), 8.18 (d, J=7.2 Hz, 1H), 7.96 (d, J=9.2 Hz, 1H), 7.86-7.66 (m, 1H), 4.72 (s, 1H), 3.68-3.64 (m, 3H), 3.02-3.01 (m, 2H), 1.68-1.66 (m, 2H), 1.27-1.23 (m, 2H); $^{19}$F-NMR (376 MHz, DMSO-$d_6$) δ -103.56, -115.48, -130.45, -133.62, -164.42.

Using the appropriate amine and Compound 33 or Compound 34 in transformations similar to those described for Step 2 of Scheme 11 in Example 8, the following compounds were also prepared:

N-((4-chloro-2',3',4',6,6'-pentafluoro-[1,1'-biphenyl]-3-yl)sulfonyl)thiomorpholine-4-carboxamide (Compound 54), isolated as white solid: MS (ESI) calc'd for $C_{17}H_{12}ClF_5N_2O_3S_2$ [M+1]$^+$=487.0, found 486.9; $^1$H-NMR (400 MHz, DMSO-$d_6$+$D_2O$) δ 8.00 (d, J=8.0 Hz, 1H), 7.76-7.69 (m, 1H), 7.59 (d, J=9.6 Hz, 1H), 3.59 (s, 4H), 2.40 (s, 4H); $^{19}$F-NMR (377 MHz, DMSO-$d_6$) δ -111.97, -115.45, -131.53, -133.81, -164.74;

N-((4-chloro-2',3',4',6,6'-pentafluoro-[1,1'-biphenyl]-3-yl)sulfonyl)thiomorpholine-4-carboxamide 1,1-dioxide (Compound 57), isolated as white solid: MS (ESI) calc'd for $C_{17}H_{12}ClF_5N_2O_5S_2$ [M+1]$^+$=519.0, found 519.0; $^1$H-NMR (400 MHz, DMSO-$d_4$) δ 8.01 (d, J=8.0 Hz, 1H), 7.74-7.70 (m, 1H), 7.63 (d, J=9.2 Hz, 1H), 3.76 (s, 4H), 2.91 (s, 4H); $^{19}$F-NMR (377 MHz, DMSO-$d_6$) δ -111.41, -115.47, -131.47, -133.81, -164.75;

N-((4-chloro-2',3',4',6,6'-pentafluoro-[1,1'-biphenyl]-3-yl)sulfonyl)morpholine-4-carboxamide (Compound 58), isolated as white solid: MS (ESI) calc'd for $C_{17}H_{12}ClF_5N_2O_4S$ [M-1]$^-$=469.0, found 468.9; $^1$H-NMR (400 MHz, DMSO-$d_6$+$D_2O$) δ 8.00 (d, J=8.0 Hz, 1H), 7.74-7.70 (m, 1H), 7.59 (d, J=9.6 Hz, 1H), 3.45 (s, 4H), 3.27 (s, 4H); $^{19}$F-NMR (377 MHz, DMSO-$d_6$) δ -111.99, -115.48, -131.51, -133.84, -164.75;

4-chloro-2',3',4',6,6'-pentafluoro-N-(phenylcarbamoyl)-[1,1'-biphenyl]-3-sulfonamide (Compound 61), isolated as white solid: MS (ESI) calc'd for $C_{19}H_{10}ClF_5N_2O_3S$ [M+1]$^+$= 477.0, found 477.0; $^1$H-NMR (400 MHz, DMSO-$d_6$) δ 8.44 (s, 1H), 8.08 (d, J=8.0 Hz, 1H), 7.78-7.72 (m, 1H), 7.61 (d, J=9.6 Hz, 1H), 7.43-7.40 (m, 2H), 7.09-7.05 (m, 2H), 6.74-6.70 (m, 1H), 6.08-6.02 (br, 1H); $^{19}$F-NMR (377 MHz, DMSO-$d_6$) δ -111.40, -115.43, -131.33, -133.77, -164.64; and N-((4-chloro-2',3',4',6,6'-pentafluoro-[1,1'-biphenyl]-3-yl)sulfonyl)piperidine-1-carboxamide (Compound 62), isolated as white solid: MS (ESI) calc'd for $C_{18}H_{14}ClF_5N_2O_3S$ [M+1]$^+$=469.0, found 469.0; $^1$H-NMR (400 MHz, DMSO-$d_6$+$D_2O$) δ 7.97 (d, J=7.6 Hz, 1H), 7.76-7.70 (m, 1H), 7.56 (d, J=9.6 Hz, 1H), 3.27-3.26 (m, 4H), 1.46-1.44 (m, 2H), 1.32-1.28 (m, 4H); $^{19}$F-NMR (377 MHz, DMSO-$d_6$) δ -111.61, -115.36, -131.10, -133.74, -164.61.

Example 10. Preparation of N-((4-chloro-2',3',4',6,6'-pentafluoro-[1,1'-biphenyl]-3-yl)sulfonyl)-2,5,6,9,10,13,14,17-octaoxanonadecan-19-amide (Compound 36)

Scheme 12

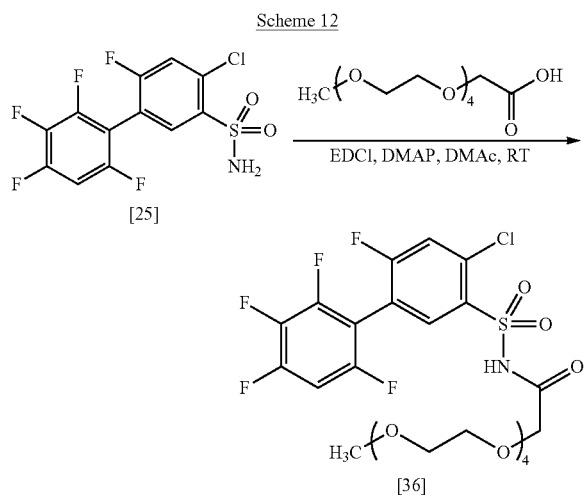

As shown in Scheme 12, to a stirred solution of 4-chloro-2',3',4',6,6'-pentafluoro-[1,1'-biphenyl]-3-sulfonamide (100 mg, 0.28 mmol) in dimethylacetamide (1 mL) were added 2-((2-((2-((2-($\lambda^1$-oxidaneyl)ethyl)peroxy)ethyl)peroxy)ethyl)-(2-methoxyethyl)peroxy)acetic acid (149 mg, 0.56 mmol), 1-ethyl-3-(3-dimethylaminopropyl)carbodiimide (EDCI, 160 mg, 0.84 mmol) and 4-dimethylaminopyridine (DMAP, 3 mg, 0.03 mmol). The resulting mixture was stirred at 25° C. for 2 hours, followed by the addition of water and extraction with EtOAc. The organics were washed with 0.5M HCl), dried over anhydrous sodium sulfate, filtered, concentrated under reduced pressure, and purified by reversed-phase preparative HPLC (46% to 56% acetonitrile/0.1% FA in H$_2$O) to afford N-((4-chloro-2',3',4',6,6'-pentafluoro-[1,1'-biphenyl]-3-yl)sulfonyl)-2,5,6,9,10,13,14,17-octaoxanonadecan-19-amide (Compound 36, 18 mg, 11% yield) as a white semi-solid: MS (ESI) calculated for C$_2$H$_{25}$ClF$_5$NO$_8$S [M−1]$^-$=604.0, found 604.1; $^1$H-NMR (400 MHz, DMSO-d$_6$) δ 12.67 (s, 1H), 8.28 (d, J=7.2 Hz, 1H), 8.00 (d, J=9.2 Hz, 1H), 7.86-7.61 (m, 1H), 4.05 (s, 2H), 3.55-3.51 (m, 5H), 3.49-3.48 (m, 9H), 3.42-3.40 (m, 2H), 3.23 (s, 3H); $^{19}$F-NMR (376 MHz, DMSO-d$_6$) δ −104.72, −115.49, −130.70, −133.48, −164.55.

Using the appropriate carboxylic acid in transformations similar to those described in Scheme 12 in Example 10, the following compounds were also prepared:

N-((4-chloro-2',3',4',6,6'-pentafluoro-[1,1'-biphenyl]-3-yl)sulfonyl)tetrahydro-2H-thiopyran-4-carboxamide (Compound 37) isolated as a white solid: MS (ESI) calculated for C$_{18}$H$_{13}$ClF$_5$NO$_3$S$_2$ [M−1]$^-$=484.0, found 483.9; $^1$H-NMR (400 MHz, DMSO-d$_6$) δ 12.68 (s, 1H), 8.27 (d, J=7.2 Hz, 1H), 8.02 (d, J=9.2 Hz, 1H), 7.82-7.70 (m, 1H), 2.62-2.32 (m, 5H), 2.07-1.91 (m, 2H), 1.57-1.46 (m, 2H); $^{19}$F-NMR (377 MHz, DMSO-d$_6$) δ −103.53, −115.49, −130.65, −133.48, −164.61;

N-((4-chloro-2',3',4',6,6'-pentafluoro-[1,1'-biphenyl]-3-yl)sulfonyl)-2-(2-chlorophenyl)acetamide (Compound 38) isolated as a white solid: MS (ESI) calculated for C$_{20}$H$_{10}$Cl$_2$F$_5$NO$_3$S [M−1]$^-$=507.9, found 507.9; $^1$H-NMR (400 MHz, DMSO-d$_4$) δ 13.03 (s, 1H), 8.24 (d, J=7.2 Hz, 1H), 8.06 (d, J=9.6 Hz, 1H), 7.83-7.68 (m, 1H), 7.43-7.34 (m, 1H), 7.37-7.29 (m, 1H), 7.33-7.22 (m, 2H), 3.83 (s, 2H); $^{19}$F-NMR (376 MHz, DMSO-d$_6$) δ −103.40, −115.45, −130.61, −133.48, −164.65;

(1s,4s)-N-((4-chloro-2',3',4',6,6'-pentafluoro-[1,1'-biphenyl]-3-yl)sulfonyl)-4-hydroxycyclohexane-1-carboxamide (Compound 39) isolated as a white solid: MS (ESI) calculated for C$_{19}$H$_{15}$ClF$_5$NO$_4$S [M−1]$^-$=481.8, found 481.8; $^1$H-NMR (400 MHz, DMSO-d$_6$) δ 12.56 (s, 1H), 8.27 (d, J=7.2 Hz, 1H), 8.03 (d. J=9.2 Hz, 1H), 7.82-7.70 (m, 1H), 4.31 (s, 1H), 3.71 (s, 1H), 2.38-2.28 (m, 1H), 1.71-1.50 (m, 4H), 1.50-1.33 (m, 4H); $^{19}$F-NMR (376 MHz, DMSO-4) δ −103.56, −115.49, −130.70, −133.48, −164.55;

N-((4-chloro-2',3',4',6,6'-pentafluoro-[1,1'-biphenyl]-3-yl)sulfonyl)tetrahydro-2H-thiopyran-4-carboxamide 1,1-dioxide (Compound 40) isolated as a white solid: MS (ESI) calculated for C$_{18}$H$_{13}$ClF$_5$NO$_5$S$_2$ [M−1]$^-$=515.9, found 515.9; $^1$H-NMR (400 MHz, DMSO-4) δ 8.27 (d, J=7.2 Hz, 1H), 8.00 (d, J=9.2 Hz, 1H), 7.76-7.65 (m, 1H), 3.21-3.10 (m, 2H), 3.10-3.00 (m, 2H), 2.74-2.62 (m, 1H), 2.21-2.11 (m, 2H), 1.95-1.80 (m, 2H); $^{19}$F-NMR (376 MHz, DMSO-d$_6$) δ −103.18, −15.48, −130.43, −133.56, −164.52;

N-((4-chloro-2',3',4',6,6'-pentafluoro-[1,1'-biphenyl]-3-yl)sulfonyl)-3,3,3,3,3,3,3,3,3,3,3-undecamethyl-$\lambda^{16}$-butanamide (Compound 41), isolated as a white solid: C$_{27}$H$_{33}$ClF$_5$NO$_3$S [M−1]$^-$=580.1, found 580.2; $^1$H-NMR (400 MHz, DMSO-d$_6$) δ 12.63 (s, 1H), 8.27 (d, J=7.2 Hz, 1H), 8.02 (d, J=9.2 Hz, 1H), 7.83-7.72 (m, 1H), 2.26 (t, J=7.2 Hz, 2H), 1.43 (p, J=7.2 Hz, 2H), 1.28-1.22 (m, 22H), 0.89-0.81 (m, 3H); $^{19}$F-NMR (376 MHz, DMSO-d$_4$) δ −103.61, −115.51, −130.66, −133.46, −164.60;

N-((4-chloro-2',3',4',6,6'-pentafluoro-[1,1'-biphenyl]-3-yl)sulfonyl)cyclopropanecarboxamide (Compound 60), isolated as white solid: MS (EST) calc'd for C$_{16}$H$_9$ClF$_5$NO$_3$S [M−1]$^-$=424.0, found 423.9; $^1$H-NMR (400 MHz, DMSO-d$_6$) δ 12.91 (br, 1H), 8.25 (d, J=7.2 Hz, 1H), 8.01 (d, J=9.2 Hz, 1H), 7.78-7.71 (m, 1H), 1.82-1.77 (m, 1H), 0.88-0.65 (m, 4H); $^{19}$F-NMR (377 MHz, DMSO-d$_6$) δ −103.55, −115.50, −130.95, −133.54, −164.66; and N-((4-chloro-2',3',4',6,6'-pentafluoro-[1,1'-biphenyl]-3-yl)sulfonyl)-3-methylbutanamide (Compound 65), isolated as white solid: MS (ESI) calc'd for C$_{17}$H$_{13}$ClF$_5$NO$_3$S [M−1]$^-$=440.0, found 440.0; $^1$H-NMR (400 MHz, DMSO-d$_6$) δ 12.61 (br, 1H), 8.28 (d, J=7.2 Hz, 1H), 8.03 (d, J=9.2 Hz, 1H), 7.78-7.74 (m, 1H), 2.15 (d, J=7.2 Hz, 2H), 1.97-1.90 (m, 1H), 0.82 (d, J=6.8 Hz, 6H); $^{19}$F-NMR (377 MHz, DMSO-d$_6$) δ −103.50, −115.55, −130.69, −133.57, −164.71.

Example 11. Preparation of 2-(tert-butoxy)-N-((4-chloro-2',3',4',6,6'-pentafluoro-[1,1'-biphenyl]-3-yl)sulfonyl)acetamide (Compound 42) and N-((4-chloro-2',3',4',6,6'-pentafluoro-[1,1'-biphenyl]-3-yl)sulfonyl)-2-hydroxyacetamide (Compound 43)

Scheme 13

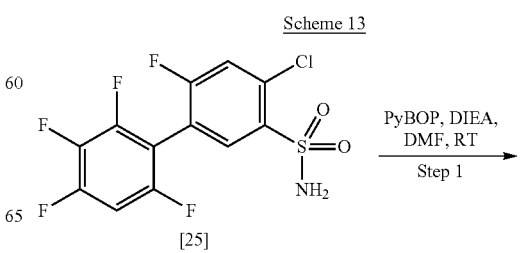

85

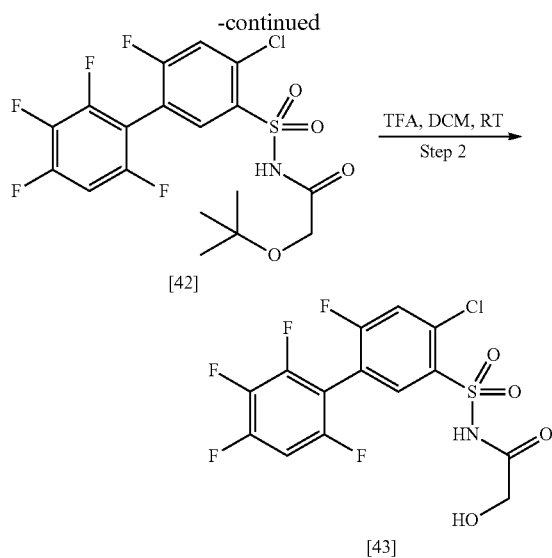

As shown in Step 1 of Scheme 13, To a stirred mixture of 4-chloro-2',4',6,6'-tetrafluoro-[1,1'-biphenyl]-3-sulfonamide (50 mg, 0.14 mmol) and tert-butoxyacetic acid (19.4 mg, 0.14 mmol) in DMF (1 mL) were added DIEA (57.0 mg, 0.44 mmol) and benzotriazol-1-yloxytripyrrolidinophosphonium hexafluorophosphate (PyBOP, 114.9 mg, 0.22 mmol) under an atmosphere of nitrogen. The resulting mixture was stirred at 25° C. for 2 hours, diluted with water, and extracted with ethyl acetate. The combined organics were dried over sodium sulfate, filtered, concentrated under reduced pressure and purified by reversed-phase preparative HPLC (67% to 77% acetonitrile/0.1% FA in H$_2$O) to afford 2-(tert-butoxy)-N-((4-chloro-2',3',4',6,6'-pentafluoro-[1,1'-biphenyl]-3-yl)sulfonyl)acetamide (Compound 42, 24 mg, 21% yield) as a white solid: $^1$H-NMR (400 MHz, DMSO-d$_6$) δ 12.59 (s, 1H), 8.28 (d. J=7.6 Hz, 1H), 8.03 (d, J=9.6 Hz, 1H), 7.83-7.71 (m, 1H), 3.95 (s, 2H), 1.09 (s, 9H); $^{19}$F-NMR (376 MHz, DMSO-d$_6$) δ −103.52, −115.53, −130.64, −133.57, −169.36.

As shown in Step 2 of Scheme 13, to a stirred mixture of 2-(tert-butoxy)-N-((4-chloro-2',3',4',6,6'-pentafluoro-[1,1'-biphenyl]-3-yl)sulfonyl)acetamide (130 mg, 0.27 mmol) in DCM (1 mL) was added TFA (1 mL). The resulting mixture was stirred at 25° C. for 2 hours under a nitrogen atmosphere. The solvent was removed under reduced pressure and the residue purified by reversed-phase preparative HPLC (42% to 52% acetonitrile/0.1% FA in H$_2$O) to afford N-((4-chloro-2',3',4',6,6'-pentafluoro-[1,1'-biphenyl]-3-yl)sulfonyl)-2-hydroxyacetamide (Compound 43, 24 mg, 21% yield) as a white solid: MS (ESI) calculated for C$_{14}$H$_7$ClF$_5$NO$_4$S) [M−1]$^−$=414.0, found 413.9; $^1$H-NMR (400 MHz, DMSO-d$_6$) δ 12.62 (s, 1H), 8.30 (d, J=7.2 Hz, 1H), 8.02 (d, J=9.2 Hz, 1H), 7.82-7.71 (m, 1H), 5.22 (s, 1H), 3.95 (s, 2H); $^{19}$F-NMR (376 MHz, DMSO-d$_6$) δ −104.11, −15.55, −130.71, −133.54, −164.61.

Using the appropriate carboxylic acid in transformations similar to those described in Step 1 of Scheme 13 in Example 11, the following compounds were also prepared:

N-((4-chloro-2',3',4',6,6'-pentafluoro-[1,1'-biphenyl]-3-yl)sulfonyl)-2-(3-chlorophenyl)acetamide (Compound 44) isolated as a white solid: MS (ESI) calculated for (C$_{20}$H$_{10}$Cl$_2$F$_5$NO$_3$S) [M−1]$^−$=507.9, found 507.9; $^1$H-NMR (400 MHz, DMSO-d$_6$) δ 12.98 (s, 1H), 8.23 (d, J=7.2 Hz, 1H), 7.99 (d, J=9.2 Hz, 1H), 7.80-7.68 (m, 1H), 7.37-7.29 (m, 2H), 7.27 (d, J=2.0 Hz, 1H), 7.20-7.12 (m, 1H), 3.65 (s, 2H); $^{19}$F-NMR (377 MHz, DMSO-d$_6$) δ −103.44, −115.50, −130.65, −133.56, −164.63;

(1r,4r)-N-((4-chloro-2',3',4',6,6'-pentafluoro-[1,1'-biphenyl]-3-yl)sulfonyl)-4-hydroxycyclohexane-1-carboxamide (Compound 45) isolated as a white solid: MS (ESI) calculated for (C$_{19}$H$_{15}$ClF$_5$NO$_4$S) [M+1]$^+$=484.03; found, 484.03; $^1$H-NMR (400 MHz, DMSO-d$_6$) δ 8.20 (d, J=7.2 Hz, 1H), 7.93 (d, J=9.2 Hz, 1H), 7.68-7.62 (m, 1H), 3.29-3.26 (m, 1H), 2.19-2.16 (m, 1H), 1.88-1.77 (m, 2H), 1.74-1.65 (m, 2H), 1.33-0.99 (m, 5H); $^{19}$F-NMR (376 MHz, DMSO-d$_4$) δ −103.52, −15.53, −130.30, −133.50, −164.43;

N-((4-chloro-2',3',4',6,6'-pentafluoro-[1,1'-biphenyl]-3-yl)sulfonyl)cyclohexanecarboxamide (Compound 46) isolated as a white solid: MS (ESI) calculated for (C$_{19}$H$_{15}$ClF$_5$NO$_3$S) [M−1]$^−$=466.0, found 466.0; $^1$H-NMR (400 MHz, DMSO-d$_6$) δ 12.59 (s, 1H), 8.27 (d. J=7.2 Hz, 1H), 8.03 (d, J=9.2 Hz, 1H), 7.85-7.52 (m, 1H), 2.38-2.17 (m, 1H), 1.80-1.58 (m, 5H), 1.31-0.96 (m, 5H); $^{19}$F-NMR (376 MHz, DMSO-d$_6$) δ −103.56, −115.48, −130.63, −133.43, −164.52; and N-((4-chloro-2',3',4',6,6'-pentafluoro-[1,1'-biphenyl]-3-yl)sulfonyl)-2-methoxyacetamide (Compound 47) isolated as a white solid: MS (ESI) calculated for (C$_{15}$H$_9$ClF$_5$NO$_4$S) [M−1]$^−$=428.0, found 427.9; $^1$H-NMR (400 MHz, DMSO-d$_6$) δ 12.82 (s, 1H), 8.29 (d, J=7.2 Hz, 1H), 8.02 (d, J=9.2 Hz, 1H), 7.82-7.71 (m, 1H), 3.97 (s, 2H), 3.24 (s, 3H); $^{19}$F-NMR (376 MHz, DMSO-d$_6$) δ −103.36, −115.51, −130.63, −133.43, −164.52.

Example 12. Preparation of 4-chloro-2',3',4',6,6'-pentafluoro-N-(methylsulfonyl)-[1,1-biphenyl]-3-sulfonamide (Compound 48)

Scheme 14

As shown in Scheme 14, to a stirred mixture of 4-chloro-2',3',4',6,6'-pentafluoro-[1,1'-biphenyl]-3-sulfonamide (100 mg, 0.28 mmol), TEA (85 mg, 0.84 mmol), DMAP (0.3 mg, 0.01 mmol) in DCM (1 mL) at 0° C. under an atmosphere of nitrogen was added methanesulfonyl chloride (64 mg, 0.56 mmol) in DMF (0.2 mL). The resulting mixture was stirred at 25° C. for 16 hours, diluted with water, and the aqueous phase extracted with ethyl acetate. The combined organics were dried over sodium sulfate, filtered, concentrated under reduced pressure, and purified by reversed-phase preparative HPLC (42% to 52% acetonitrile/0.05%

HCl in water) to afford 4-chloro-2',3',4',6,6'-pentafluoro-N-(methylsulfonyl)-[1,1'-biphenyl]-3-sulfonamide (Compound 48, 12 mg, 10% yield) as a white solid; MS (ESI) calculated for $C_{13}H_7ClF_5NO_4S_2$ [M-1]$^-$=433.9, found 433.8; $^1$H-NMR (400 MHz, DMSO-d$_6$) δ 8.03 (d. J=7.6 Hz, 1H), 7.79-7.67 (m, 2H), 2.80 (s, 3H); $^{19}$F-NMR (376 MHz, DMSO-d$_6$) δ -110.04, -115.55, -131.24, -133.82, -164.61.

Using the same procedure as described for Scheme 14 and substituting ethanesulfonyl chloride for methanesulfonyl chloride, 4-chloro-N-(ethylsulfonyl)-2',3',4',6,6'-pentafluoro-[1,1'-biphenyl]-3-sulfonamide (Compound 49) was also produced as a white solid: MS (ESI) calculated for $(C_{14}H_9ClF_5NO_4S_2)$ [M-1]$^-$=448.0, found 447.9; $^1$H-NMR (400 MHz, DMSO-d$_6$) δ 8.02 (d, J=7.6 Hz, 1H), 7.79-7.67 (m, 2H), 2.89 (q, J=7.2 Hz, 2H), 1.13 (t, J=7.2 Hz, 3H); $^{19}$F-NMR (376 MHz, DMSO-d$_4$) δ -110.17, -115.55, -131.25, -133.81, -164.60.

Example 13. Preparation of N-((2',3',4,4',6,6'-hexafluoro-[1,1'-biphenyl]-3-yl)sulfonyl)propionamide (Compound 50)

Scheme 15

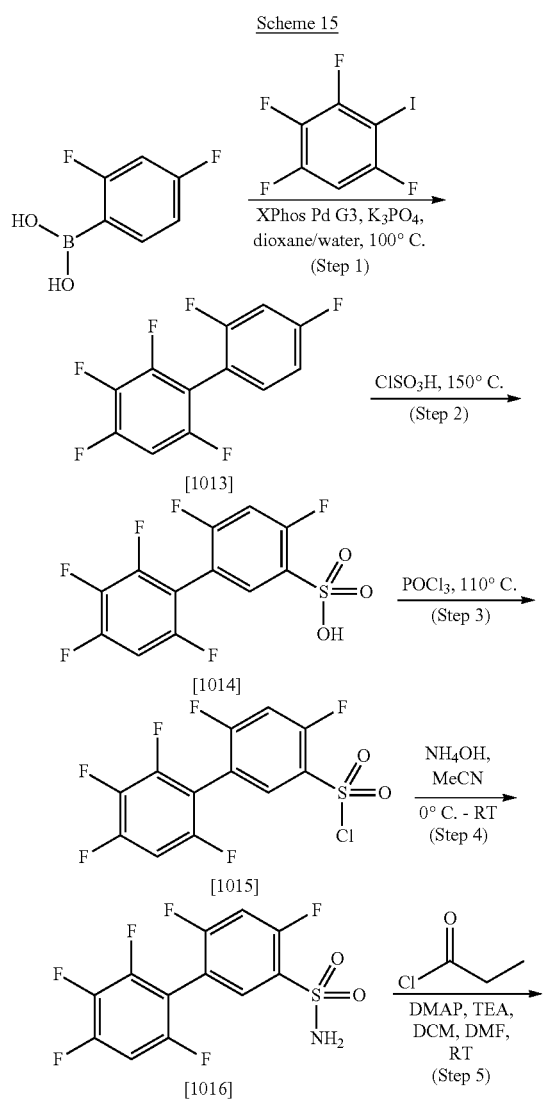

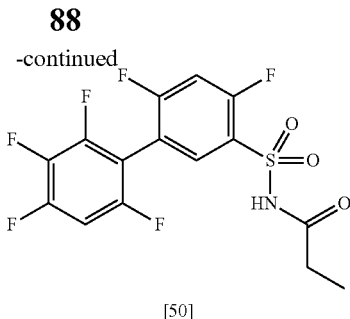

[50]

As shown in Step 1 of Scheme 15, to a stirred mixture of 1,2,3,5-tetrafluoro-4-iodobenzene (1.6 g, 5.79 mmol) and 2,4-difluorophenylboronic acid (0.92 g, 5.79 mmol) in 1,4-dioxane (20 mL) and H$_2$O (4 mL) were added XPhos Pd G3 (0.98 g, 1.16 mmol) and K$_3$PO$_4$ (2.5 g, 11.59 mmol). The resulting mixture was stirred overnight at 100° C. under an atmosphere of nitrogen, cooled, diluted with water, and extracted with EtOAc. The combined organics were washed with brine, dried over anhydrous Na$_2$SO$_4$, filtered, concentrated under reduced pressure, and purified by silica gel column chromatography (1:1 DCM/petroleum ether) to afford 2,2',3,4,4',6-hexafluoro-1,1'-biphenyl (Compound 1013, 1.0 g, 65% yield) as a yellow solid; GCMS (ESI) calculated for $C_{12}H_4F_6$, 262.0, found 262.0.

As shown in Step 2 of Scheme 15, to a stirred solution of chlorosulfonic acid (11.6 g, 99 mmol) in CHCl$_3$ (10 mL) was added 2,2',3,4,4',6-hexafluoro-1,1'-biphenyl (Compound 1013, 1.3 g, 5 mmol), followed by the addition of SOCl$_2$ (1.18 g, 9.9 mmol) dropwise at 0° C. The resulting mixture was stirred for 16 hours at 150° C. After cooling, the solvent was removed under reduced pressure and the residue diluted with water and extracted with EtOAc. The combined organics were washed with brine, dried over anhydrous Na$_2$SO$_4$, filtered, and concentrated under reduced pressure to afford 2',3',4,4',6,6'-hexafluoro-[1,1'-biphenyl]-3-sulfonic acid (Compound 1014, 1.3 g, crude) as a brown oil. This material was used directly in subsequent reactions as is.

As shown in Step 3 of Scheme 15, a solution 2',3',4,4',6,6'-hexafluoro-[1,1'-biphenyl]-3-sulfonic acid (Compound 1014, 1.3 g, 3.79 mmol) in POCl$_3$ (13 mL) was stirred for overnight at 110° C. After cooling, the mixture was concentrated under reduced pressure to afford 2',3',4,4',6,6'-hexafluoro-[1,1'-biphenyl]-3-sulfonyl chloride (Compound 1015, 1.3 g, crude) as a brown solid, which was used in subsequent reactions directly without further purification.

As shown in Step 4 of Scheme 15, to a stirred solution of saturated NH$_3$(aq) (3 mL, 77.04 mmol) in MeCN (15 mL) was added 2',3',4,4',6,6'-hexafluoro-[1,1'-biphenyl]-3-sulfonyl chloride (Compound 1015, 1.3 g, 3.60 mmol) dropwise at 0° C. The resulting mixture was stirred for 2 hours at 25° C., concentrated under reduced pressure, and purified by reversed-phase flash chromatography (5% to 100% acetonitrile/water) to afford 2',3',4,4',6,6'-hexafluoro-[1,1'-biphenyl]-3-sulfonamide (Compound 1016, 160 mg, 13% yield) as a brown oil: MS (EST) calculated for $(C_{12}H_5F_6NO_2S)$ [M-1]$^-$=340.0, found 340.0.

As shown in Step 5 of Scheme 15, to a stirred solution of propanoyl chloride (122 mg, 1.32 mmol) and TEA (133 mg, 1.32 mmol) in DMAc (2 mL) were added 2',3',4,4',6,6'-hexafluoro-[1,1'-biphenyl]-3-sulfonamide (150 mg, 0.44 mmol) and DMAP (10 mg, 0.08 mmol). The resulting mixture was stirred for 16 hours at room temperature, diluted with water, and extracted with EtOAc. The combined organics were washed with brine, dried over anhydrous Na$_2$SO$_4$, filtered, concentrated under reduced pressure, and purified by reversed-phase preparative HPLC (45% to 55% acetonitrile/0.05 FA in water) to afford N-((2',3',4,4',6,6'-hexafluoro-[1,1'-biphenyl]-3-yl)sulfonyl)propionamide (Compound 50, 24 mg, 12% yield) as a white solid: MS (ESI) calculated for C$_{15}$H$_9$F$_6$NO$_3$S) [M−1]$^−$=396.0, found 395.9; $^1$H-NMR (400 MHz, DMSO-d$_6$) δ 12.62 (s, 1H), 8.15 (t, J=7.6 Hz, 1H), 7.87 (t, J=10.0 Hz, 1H), 7.81-7.69 (m, 1H), 2.30 (q, J=7.2 Hz, 2H), 0.93 (t, J=7.2 Hz, 3H); $^{19}$F-NMR (377 MHz, DMSO-d$_6$) δ −100.00, −103.41, −115.68, −130.92, −133.65, −164.80.

Example 14. Preparation of N-((4,6-dichloro-2',3',4',6'-tetrafluoro-[1,1'-biphenyl]-3-yl)sulfonyl)propionamide (Compound 51)

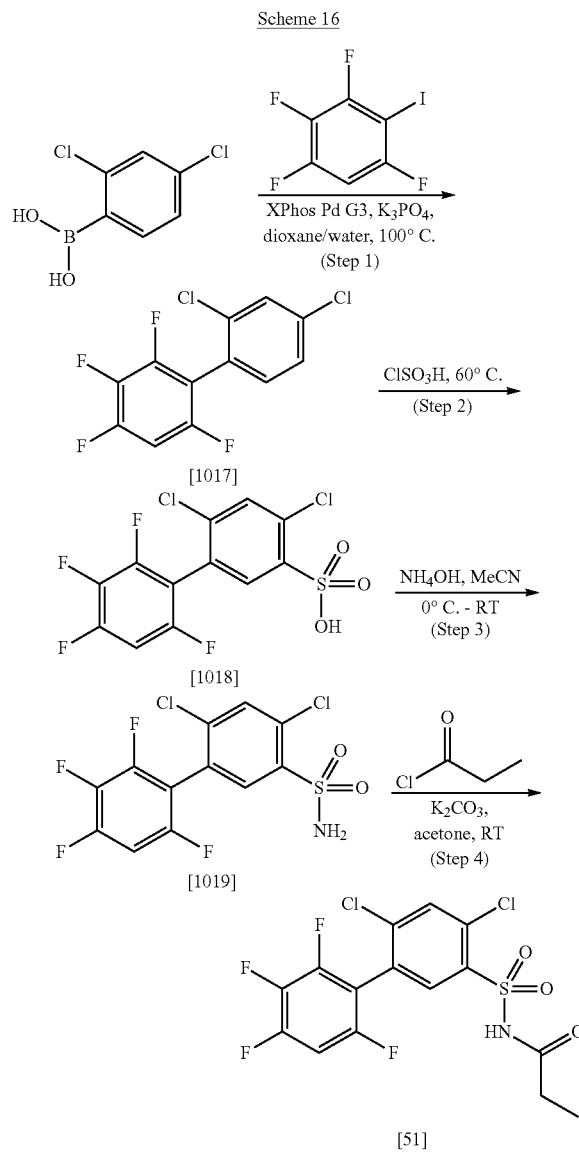

As shown in Step 1 of Scheme 16, to a stirred mixture of 1,2,3,5-tetrafluoro-4-iodobenzene (2.00 g, 7.24 mmol) and 2,4-dichlorophenylboronic acid (2.07 g, 10.87 mmol) in dioxane (20 mL) and H$_2$O (4 mL) were added XPhos Pd G3 (0.61 g, 0.72 mmol), XPhos (0.35 g, 0.72 mmol) and K$_3$PO$_4$ (3.08 g, 14.49 mmol). The resulting mixture was stirred at 100° C. for 16 hours under an atmosphere of nitrogen. After cooling, the mixture was filtered through diatomaceous earth, the filter cake washed with DCM, and the filtrate concentrated under reduced pressure. The residue was taken up EtOAc and the combined organics were washed with brine, dried over anhydrous Na$_2$SO$_4$, filtered, concentrated under reduced pressure, and purified by silica gel column chromatography (0% to 30% DCM/petroleum ether) to afford 2',4'-dichloro-2,3,4,6-tetrafluoro-1,1'-biphenyl (Compound 1017, 1.00 g, 46% yield) as a yellow oil: GCMS calculated for C$_2$H$_4$Cl$_2$F$_4$=294.0, found 294.0.

As shown in Step 2 of Scheme 16, a mixture of 2',4'-dichloro-2,3,4,6-tetrafluoro-1,1'-biphenyl (Compound 1017, 900 mg, 3.05 mmol) and chlorosulfonic acid (10 mL) was stirred at 60° C. for 2 hours. The mixture was cooled and concentrated under reduced pressure to afford 4,6-dichloro-2',3',4',6'-tetrafluoro-[1,1'-biphenyl]-3-sulfonyl chloride (Compound 1018, 1.00 g, 83% yield) as a brown oil. This material was used in subsequent steps without further purification.

As shown in Step 3 of Scheme 16, to a mixture of 4,6-dichloro-2',3',4',6'-tetrafluoro-[1,1'-biphenyl]-3-sulfonyl chloride (Compound 1018, 1.00 g, 2.54 mmol) in MeCN (10 mL) was added concentrated NH$_4$OH (aq) (1 mL), the resulting mixture was stirred at room temperature for 2 hours, concentrated under reduced pressure, and purified by reversed-phase preparative HPLC (46% to 56% acetonitrile/10 mM NH$_4$HCO$_3$ in water) to afford 4,6-dichloro-2',3',4',6'-tetrafluoro-[1,1'-biphenyl]-3-sulfonamide (Compound 1019, 240 mg, 25% yield) as a white solid: MS (ESI) calculated for C$_{12}$H$_5$Cl$_2$F$_4$NO$_2$S) [M−1]$^−$=371.9, found 371.9; $^1$H-NMR (400 MHz, DMSO-d$_6$) δ 8.16 (s, 1H), 8.11 (s, 1H), 7.84 (d, J=3.6 Hz, 2H), 7.81-7.70 (m, 1H); $^{19}$F-NMR (376 MHz, DMSO-d$_6$) δ −115.27, −130.89, −133.49, −164.83.

As shown in Step 4 of Scheme 16, to a stirred mixture of 4,6-dichloro-2',3',4',6'-tetrafluoro-[1,1'-biphenyl]-3-sulfonamide (100 mg, 0.26 mmol) and K$_2$CO$_3$ (73 mg, 0.53 mmol) in acetone (2 mL) was added propanoyl chloride (49 mg, 0.53 mmol). The resulting mixture was stirred at room temperature for 2 hours, concentrated under reduced pressure, and purified by reversed phase preparative HPLC (46% to 56% acetonitrile/0.1% FA in water) to afford N-((4,6-dichloro-2',3',4',6'-tetrafluoro-[1,1'-biphenyl]-3-yl)sulfonyl)propionamide (Compound 51, 37 mg, 31% yield) as a white solid: MS (ESI) calculated for C$_{15}$H$_9$Cl$_2$F$_4$NO$_3$S) [M−1]$^−$=428.0, found 427.9; $^1$H-NMR (400 MHz, DMSO-d$_6$) δ 12.68 (s, 1H), 8.22 (d, J=9.2 Hz, 2H), 7.82-7.70 (m, 1H), 2.31 (q, J=7.6 Hz, 2H), 0.93 (t, J=7.6 Hz, 3H); $^{19}$F-NMR (376 MHz, DMSO-d$_6$) δ −115.29, −130.91, −133.49, −164.86.

Example 15. Preparation of N-((4-chloro-2',3',4',5',6-pentafluoro-[1,1'-biphenyl]-3-yl)sulfonyl)acetamide (Compound 52)

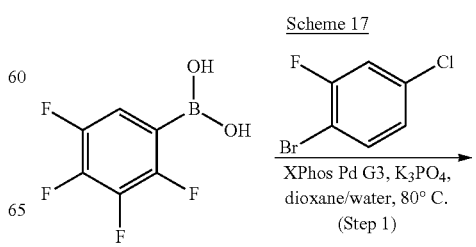

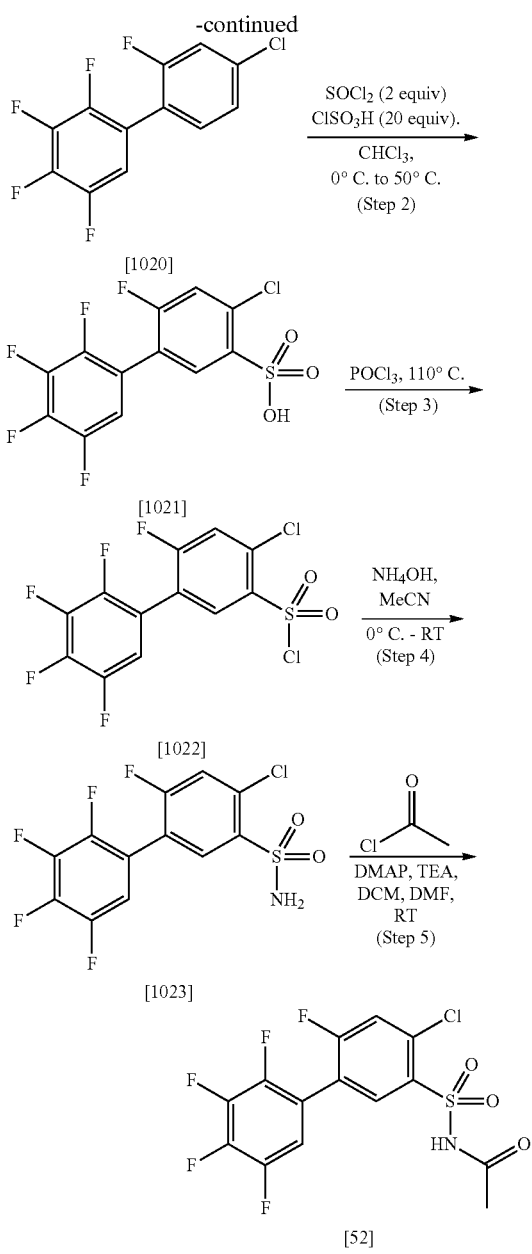

pentafluoro-1,1'-biphenyl (100.0 mg, 0.35 mmol) in CHCl$_3$ (mL) under an atmosphere of nitrogen. The resulting mixture was stirred for 16 hours at 50° C. under an atmosphere of nitrogen, diluted with water, and extracted with ethyl acetate. The combined organics were washed with brine, dried over anhydrous sodium sulfate, filtered, and concentrated under reduced pressure. The resulting residue was dissolved in DMF (2 mL) purified by reversed-phase flash chromatography (5%-75% acetonitrile/water) to afford 4-chloro-2',3',4',5',6-pentafluoro-[1,1'-biphenyl]-3-sulfonic acid (Compound 1021, 14.0 mg, 10% yield) as a white solid: MS (ESI) calculated for C$_{12}$H$_4$ClF$_5$O$_3$S [M−1]$^−$=357.1, found 357.1; $^1$H-NMR (400 MHz, DMSO-d$_6$) δ 7.93 (d, J=8.2 Hz, 1H), 7.61-7.50 (m, 2H); $^{19}$F-NMR (376 MHz, DMSO-d$_6$) δ −112.64, −139.04, −140.20, −155.11, −155.64.

As shown in Step 3 of Scheme 17, a solution of 4-chloro-2',3',4',5',6-pentafluoro-[1,1'-biphenyl]-3-sulfonic acid (2.7 g, 7.53 mmol) in POCl$_3$ (20 mL) was stirred for 2 hours at 100° C. After cooling, the volatiles were removed under reduced pressure to afford 4-chloro-2',3',4',5',6-pentafluoro-[1,1'-biphenyl]-3-sulfonyl chloride (Compound 1022, 2.7 g) as a brown oil. This material was used directly as is in subsequent reactions.

As shown in Step 4 of Scheme 17, to a stirred solution of 4-chloro-2',3',4',5',6-pentafluoro-[1,1'-biphenyl]-3-sulfonyl chloride (1.0 g, 2.65 mmol) in acetonitrile (20 mL) at 0° C. was added concentrated ammonia (1.5 g, 10.6 mmol) in portions. The resulting mixture was stirred for additional 2 hours at 0° C., diluted with water, and extracted with ethyl acetate. The combined organics were washed with brine, dried over anhydrous sodium sulfate, filtered, and concentrated under reduced pressure. The residue was dissolved in DCM (6 mL) and purified by flash chromatography (0% to 65% ethyl acetate/petroleum ether) to afford 4-chloro-2',3',4',5',6-pentafluoro-[1,1'-biphenyl]-3-sulfonamide (Compound 1023, 300 mg, 31% yield) as a brown solid: MS (ESI) calculated for C$_{12}$H$_5$ClF$_5$NO$_2$S [M−1]$^−$=355.9, found 355.9; $^1$H-NMR (400 MHz, DMSO-d$_6$) δ 8.08 (d, J=7.6 Hz, 1H), 7.94 (d, J=9.6 Hz, 1H), 7.78 (s, 2H), 7.75-7.64 (m, 1H); $^{19}$F-NMR (377 MHz, DMSO-d$_6$) δ −100.92, −139.11, −140.02, −154.58, −155.56.

As shown in Step 5 of Scheme 17, to a solution of 4-chloro-2',3',4',5',6-pentafluoro-[1,1'-biphenyl]-3-sulfonamide (Compound 1023, 200 mg, 0.56 mmol), DMAP (6.8 mg, 0.06 mmol) and TEA (113 mg, 1.12 mmol) in DCM (2 mL) and DMF (2 mL) at 0° C. was added acetyl chloride (125 mg, 1.6 mmol) under an atmosphere of nitrogen. The resulting mixture was stirred at room temperature for 3 hours, diluted with water, and extracted with ethyl acetate. The combined organics were washed with brine, dried over anhydrous sodium sulfate, filtered, and concentrated under reduced pressure. The resulting residue was dissolved in DMF (2 mL) and purified by reversed-phase flash chromatography (5% to 45% acetonitrile/water) to afford N-((4-chloro-2',3',4',5',6-pentafluoro-[1,1'-biphenyl]-3-yl)sulfonyl)acetamide (Compound 52, 90 mg, 40% yield) as a white solid: MS (ESI) calculated for C$_4$H$_7$ClF$_5$NO$_3$S [M−1]$^−$= 397.9; found 397.9. $^1$H-NMR (400 MHz, DMSO-d$_6$) δ 12.67 (s, 1H), 8.18 (d, J=7.4 Hz, 1H), 7.99 (d, J=9.6 Hz, 1H), 7.78-7.67 (m, 1H), 1.99 (s, 3H); $^{19}$F-NMR (377 MHz, DMSO-d$_6$) δ −105.01, −139.08, −139.83, −154.48, −155.54.

Using the same procedure as described for Step 5 of Scheme 17 and substituting propionyl chloride for acetyl chloride, N-((4-chloro-2',3',4',5',6-pentafluoro-[1,1'-biphenyl]-3-yl)sulfonyl)propionamide (Compound 53) was produced as a white solid: MS (ESI) calculated for C$_{11}$H$_9$ClF$_5$NO$_3$S) [M−1]$^−$=412.0, found 411.9; $^1$H-NMR (400 MHz, DMSO-d) δ 12.63 (s, 1H), 8.19 (d, J=7.6 Hz, 1H), 8.00 (d, J=9.6 Hz, 1H), 7.82-7.66 (m, 1H), 2.30 (q, J=7.2 Hz, 2H), 0.93 (t, J=7.2 Hz, 3H); $^{19}$F-NMR (377 MHz, DMSO-d$_6$) δ −104.78, −139.08, −139.79, −154.45, −155.53.

Example 16. Preparation of 2-(benzylthio)-3-chloro-5-fluoro-6-(2,3,4,6-tetrafluorophenyl)pyridine (Compound 67), 3-chloro-5-fluoro-6-(2,3,4,6-tetrafluorophenyl)pyridine-2-sulfonamide (Compound 68), and N-((3-chloro-5-fluoro-6-(2,3,4,6-tetrafluorophenyl)pyridin-2-yl)sulfonyl)propionamide (Compound 71)

Scheme 18

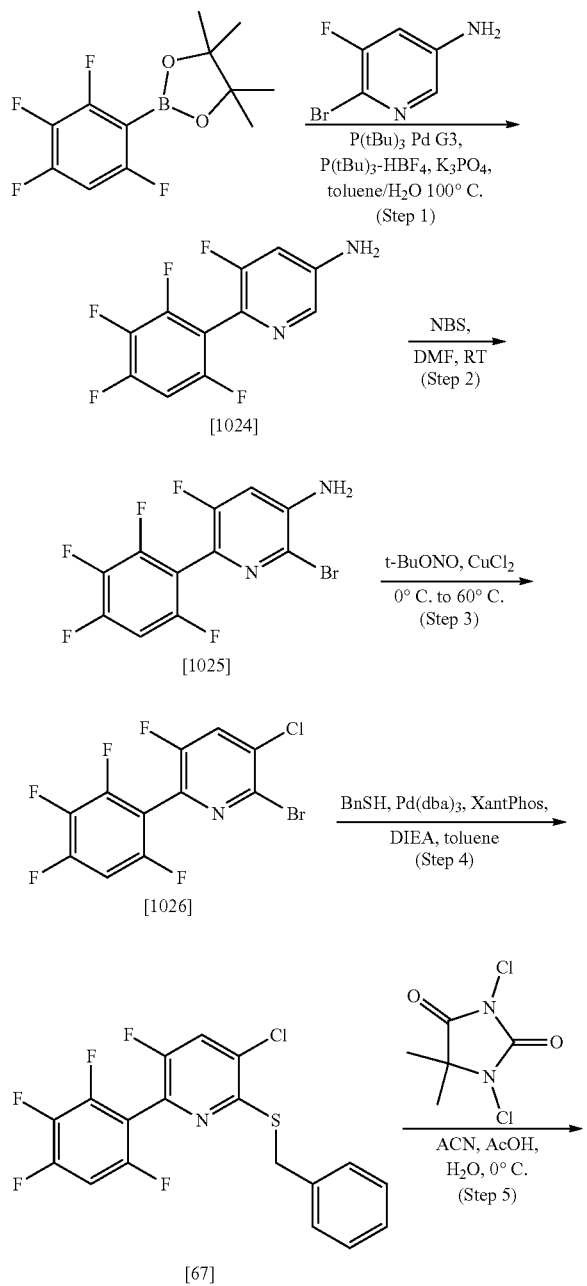

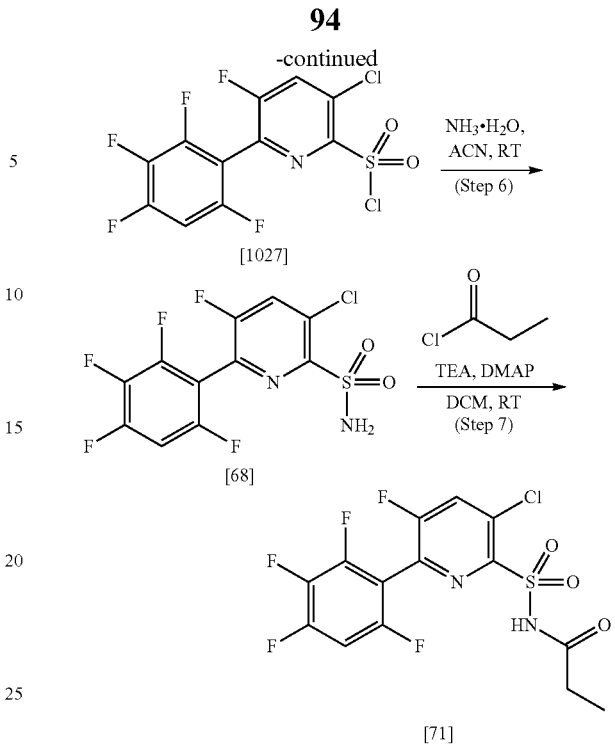

As shown in Step 1 of Scheme 18, a degassed mixture of 4,4,5,5-tetramethyl-2-(2,3,4,6-tetrafluorophenyl)-1,3,2-dioxaborolane (4.34 g, 15.7 mmol), 6-bromo-5-fluoropyridin-3-amine (3.00 g, 15.7 mmol), P(t-Bu)$_3$ Palladacycle Gen.3 (0.90 g, 1.57 mmol), CyP(t-Bu)$_2$·HBF$_4$ (0.99 g, 3.14 mmol) and K$_3$PO$_4$ (6.67 g, 31.41 mmol) in toluene (10 mL) and H$_2$O (2 mL) was stirred at 100° C. for 16 hours under a nitrogen atmosphere. After this time, the reaction mixture was diluted with water and extracted with EtOAc. The organic layers were dried over anhydrous sodium sulfate, filtered, concentrated under reduced pressure, and purified by flash chromatography (0% to 50% ethyl acetate in petroleum ether) to afford 5-fluoro-6-(2,3,4,6-tetrafluorophenyl)pyridin-3-amine (Compound 1024, 2.90 g, 70% yield) as a yellow solid: GCMS calc'd for C$_{11}$H$_5$F$_5$N$_2$=261.0, found 261.0.

As shown in Step 2 of Scheme 18, a mixture of 5-fluoro-6-(2,3,4,6-tetrafluorophenyl)pyridin-3-amine (2.90 g, 11.14 mmol) and N-bromosuccinimide (2.46 g, 13.83 mmol) in DMF (30 mL) was stirred at 25° C. for 16 hours. The resulting mixture was diluted with water and extracted with EtOAc. The combined organic layers were washed with brine, dried over anhydrous Na$_2$SO$_4$, filtered, concentrated under reduced pressure, and purified by reversed-phase flash chromatography (0% to 50% MeCN/water containing 0.1% formic acid) to afford 2-bromo-5-fluoro-6-(2,3,4,6-tetrafluorophenyl)pyridin-3-amine (Compound 1025, 2.20 g, 58% yield) as a white solid: MS (ESI) calc'd for C$_{11}$H$_4$BrF$_5$N$_2$ [M+1]$^+$=338.9, found 338.8; $^1$H-NMR (400 MHz, DMSO-d$_6$) δ 7.71-7.59 (m, 1H), 7.08 (d, J=11.2 Hz, 1H), 6.27 (s, 2H); $^{19}$F-NMR (377 MHz, DMSO-d$_4$) δ −116.16, −124.03, −131.39, −134.99, −164.91.

As shown in Step 3 of Scheme 18, a mixture of tert-butyl nitrite (0.91 g, 8.84 mmol) and CuCl$_2$ (1.19 g, 8.84 mmol) in MeCN (20 mL) was stirred 25° C. for 20 minutes, followed by the addition of 2-bromo-5-fluoro-6-(2,3,4,6-tetrafluorophenyl)pyridin-3-amine (2.00 g, 5.89 mmol). The resulting mixture was stirred at 60° C. for 16 hours, concentrated under reduced pressure, and purified by reversed-phase flash chromatography (0% to 50% MeCN/water containing 0.1% formic acid) to afford 2-bromo-3-chloro-5-fluoro-6-(2,3,4,6-tetrafluorophenyl)pyridine (Compound 1026, 1.6 g, 75% yield) as a white solid: MS (ESI) calc'd for $C_{11}H_2BrClF_5N$ [M+1]$^+$=357.9, found 359.8; $^1$H-NMR (400 MHz, DMSO-d$_6$) δ 8.58 (d, J=8.8 Hz, 1H), 7.83-7.71 (m, 1H); $^{19}$F-NMR (377 MHz, DMSO-d$_6$) δ −115.75, −120.39, −128.78, −134.45, −164.03.

As shown in Step 4 of Scheme 18, to a stirred mixture of 2-bromo-3-chloro-5-fluoro-6-(2,3,4,6-tetrafluorophenyl)pyridine (1.6 g, 4.46 mmol) and 4-bromobenzyl mercaptan (1.00 g, 4.90 mmol) in toluene (25 mL) was added Pd$_2$(dba)$_3$ (0.40 g, 0.44 mmol, 0.1 equiv), XantPhos (0.51 g, 0.89 mmol), and DIEA (1.15 g, 8.89 mmol). The resulting mixture was stirred at 100° C. for 16 hours under nitrogen atmosphere. After cooling, the mixture was extracted with EtOAc and the combined organic layers were washed with brine, dried over anhydrous Na$_2$SO$_4$, filtered, concentrated under reduced pressure, and purified by reversed-phase flash chromatography (0% to 100% MeCN/water containing 0.1% formic acid) to afford 2-(benzylthio)-3-chloro-5-fluoro-6-(2,3,4,6-tetrafluorophenyl)pyridine (Compound 67, 1.2 g, 66% yield) as a white solid: MS (ESI) calc'd for $C_{18}H_9ClF_5NS$ [M+1]$^+$=402.0, found 401.9; $^{19}$F-NMR (377 MHz, DMSO-d$_6$) δ −115.63, −125.61, −129.45, −134.41, −164.32.

As shown in Step 5 of Scheme 18, to a stirred mixture of 2-(benzylsulfanyl)-3-chloro-5-fluoro-6-(2,3,4,6-tetrafluorophenyl)pyridine (500 mg, 1.24 mmol) in H$_2$O (0.5 mL), AcOH (0.5 mL), and MeCN (10 mL) was added 1,3-dichloro-5,5-dimethylimidazolidine-2,4-dione (612 mg, 3.11 mmol). The resulting mixture was stirred at 0° C. for 2 hours and concentrated under reduced pressure to afford 3-chloro-5-fluoro-6-(2,3,4,6-tetrafluorophenyl)pyridine-2-sulfonyl chloride (Compound 1027, 400 mg, crude) as a yellow oil. This material was used as is in subsequent reactions without further purification.

As shown in Step 6 of Scheme 18, a mixture of 3-chloro-5-fluoro-6-(2,3,4,6-tetrafluorophenyl)pyridine-2-sulfonyl chloride (200 mg, 0.52 mmol) and NH$_4$OH (0.5 mL) in MeCN (2 mL) was stirred at 25° C. for 1 hour, followed by concentration under reduced pressure. The residue was purified by reversed-phase flash chromatography (0% to 50% MeCN in 10 mM aqueous NH$_4$HCO$_3$) to afford 3-chloro-5-fluoro-6-(2,3,4,6-tetrafluorophenyl)pyridine-2-sulfonamide (Compound 68) as a white solid: MS (ESI) calc'd for $C_{11}H_4ClF_5N_2O_2S$ [M−1]$^-$=357.0, found 356.9; $^1$H-NMR (400 MHz, DMSO-d$_6$) δ 8.63 (d, J=8.8 Hz, 1H), 7.81 (s, 2H), 7.78-7.72 (m, 1H); $^{19}$F-NMR (377 MHz, DMSO-d$_6$) δ −114.46, −115.42, −128.39, −134.05, −164.17.

As shown in Step 7 of Scheme 18, to a stirred mixture of 3-chloro-5-fluoro-6-(2,3,4,6-tetrafluorophenyl)pyridine-2-sulfonamide (100 mg, 0.27 mmol) and TEA (56 mg, 0.55 mmol) in DCM (2 mL) were added propionyl chloride (38 mg, 0.41 mmol) and DMAP (3 mg, 0.02 mmol). The resulting mixture was stirred at 25° C. for 2 hours, followed by the addition of 1M HCl. The mixture was extracted with EtOAc and the combined organic layers were washed with brine, dried over anhydrous Na$_2$SO$_4$, filtered, concentrated under reduced pressure, and purified by reversed-phase preparative-HPLC (20% to 30% MeCN/water containing 0.1% formic acid) to afford N-((3-chloro-5-fluoro-6-(2,3,4,6-tetrafluorophenyl)pyridin-2-yl)sulfonyl)propionamide (Compound 71, 47.6 mg, 41% yield) as a white solid: MS (ESI) calc'd for $C_{14}H_8ClF_5N_2O_3S$ [M−1]$^-$=413.0, found 412.9; $^1$H-NMR (400 MHz, DMSO-d$_6$) δ 12.41 (br, 1H), 8.72 (d, J=8.4 Hz, 1H), 7.86-7.79 (m, 1H), 2.32 (q, J=7.2 Hz, 2H), 0.93 (t, J=7.2 Hz, 3H); $^{19}$F-NMR (377 MHz, DMSO-d$_6$) δ −112.18, −115.56, −128.14, −134.29, −164.06.

Example 17. Preparation of N-benzyl-N-((4-chloro-2',3',4',6,6'-pentafluoro-[1,1'-biphenyl]-3-yl)sulfonyl)propionamide (Compound 69)

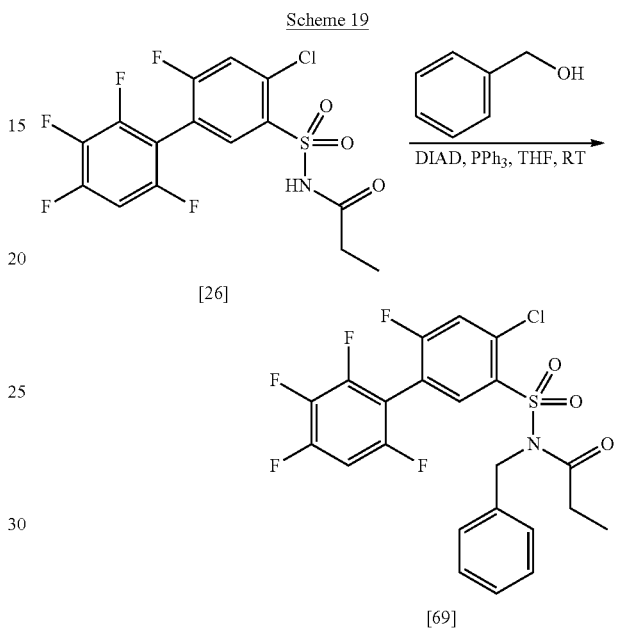

Scheme 19

As shown in Scheme 19, to a solution of N-((4-chloro-2',3',4',6,6'-pentafluoro-[1,1'-biphenyl]-3-yl)sulfonyl)propionamide (140 mg, 0.33 mmol) and benzyl alcohol (43 mg, 0.40 mmol) in THF (2 mL) were sequentially added PPh$_3$ (133 mg, 0.50 mmol) and DIAD (102 mg, 0.50 mmol) at 0° C. The reaction mixture was warmed to 25° C. and stirred for 2 hours. The reaction mixture was diluted with water and extracted with ethyl acetate. The combined organic layers were washed with brine, dried over anhydrous sodium sulfate, filtered, and concentrated under reduced pressure, dissolved in DMF (2 mL), and purified by reversed-phase prep-HPLC (2%, then 65% to 75% MeCN in 10 mM aqueous NH$_4$HCO$_3$) to afford N-benzyl-N-((4-chloro-2',3',4',6,6'-pentafluoro-[1,1'-biphenyl]-3-yl)sulfonyl)propionamide (Compound 69, 20.7 mg, 12% yield) as a white solid: MS (EST) calc'd for $C_{22}H_{15}ClF_5NO_3S$ [M−1]$^-$=504.0, found 504.1; $^1$H-NMR (400 MHz, DMSO-d$_6$) δ 8.36 (d, J=8.8 Hz, 1H), 7.72 (d, J=8.8 Hz, 1H), 7.47-7.29 (m, 6H), 5.24 (s, 2H), 2.53 (q, J=7.2 Hz, 2H), 0.90 (t, J=7.2 Hz, 3H); $^{19}$F-NMR (377 MHz, DMSO-d$_6$) δ −104.29, −117.01, −132.17, −135.12, −167.17.

Using the appropriate alcohol in transformations similar to those described in Scheme 13 in Example 19, the following compounds were also prepared:

N-((4-chloro-2',3',4',6,6'-pentafluoro-[1,1'-biphenyl]-3-yl)sulfonyl)-N-methylpropionamide (Compound 72): MS (EST) calc'd for $C_{16}H_{11}ClF_5NO_3S$ [M+1]$^+$=428.0, found 428.0; $^1$H-NMR (400 MHz, DMSO-d$_6$) δ 8.33 (d, J=7.2 Hz, 1H), 8.05 (d, J=9.6 Hz, 1H), 7.80-7.73 (m, 1H), 3.43 (s, 3H), 2.61 (q, J=7.2 Hz, 2H), 0.92 (t, J=7.2 Hz, 3H); $^{19}$F-NMR (377 MHz, DMSO-d$_6$) δ −103.49, −115.50, −130.66, −133.53, −164.67; and N-allyl-N-((4-chloro-2',3',4',6,6'-pentafluoro-[1,1'-biphenyl]-3-yl)sulfonyl)propionamide (Compound 74): MS (ESI) calc'd for $C_{18}H_{13}ClF_5NO_3S$ [M+1]$^+$=454.0, found 454.0; $^1$H-NMR (400 MHz, DMSO-d$_6$) δ 8.35 (d. J=7.2 Hz, 1H), 8.06 (d, J=9.2 Hz, 1H), 7.80-7.73 (m, 1H), 6.06-5.97 (m, 1H), 5.32-5.26 (m, 2H), 4.58 (s, 2H), 2.59 (q, J=7.2 Hz, 2H), 0.92 (t, J=7.2 Hz, 3H); $^{19}$F-NMR (377 MHz, DMSO-d$_6$) δ −103.27, −115.52, −130.65, −133.51, −164.66.

Example 18. Preparation of 4-chloro-2',3',4',6,6'-pentafluoro-N-methoxy-[1,1'-biphenyl]-3-sulfonamide (Compound 73) and N-((4-chloro-2',3',4',6,6'-pentafluoro-[1,1'-biphenyl]-3-yl)sulfonyl)-N-methoxypropionamide (Compound 76)

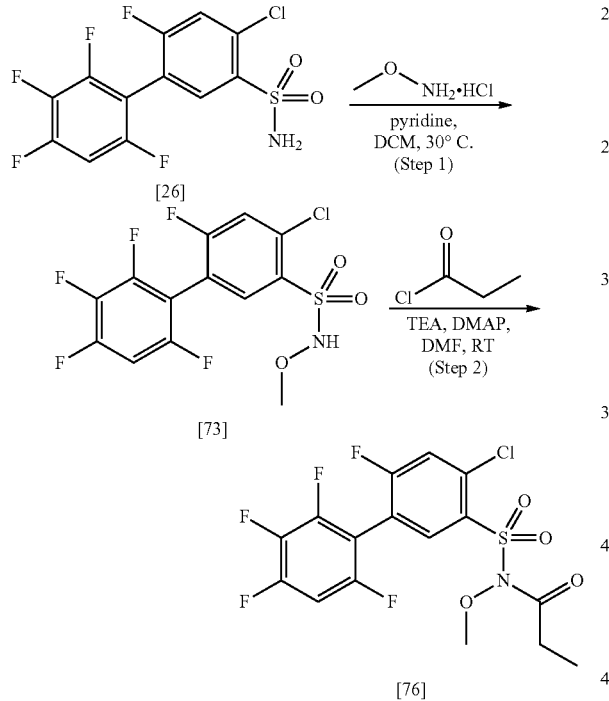

As shown in Step 1 of Scheme 20, to a stirred solution of 4-chloro-2',3',4',6,6'-pentafluoro-[1,1'-biphenyl]-3-sulfonyl chloride (200 mg, 0.53 mmol) in DCM (5 mL) were added O-methylhydroxylamine hydrochloride (88 mg, 1.06 mmol) and pyridine (84 mg, 1.06 mmol). The resulting mixture was stirred at 25° C. for 2 hours, diluted by the addition of water, and extracted with ethyl acetate. The combined organic layers were washed with brine, dried over anhydrous sodium sulfate, filtered, concentrated under reduced pressure, and purified by flash chromatography (0% to 30% ethyl acetate in petroleum ether) to afford 4-chloro-2',3',4',6,6'-pentafluoro-N-methoxy-[1,1'-biphenyl]-3-sulfonamide (Compound 73, 130 mg, 63% yield) as a white solid: MS (ESI) calc'd for $C_{13}H_7ClF_5NO_3S$ [M−1]$^-$=386.0, found 385.9; $^1$H-NMR (400 MHz, DMSO-d$_4$) δ 10.97 (s, 1H), 8.17 (d, J=7.2 Hz, 1H), 8.06 (d, J=9.2 Hz, 1H), 7.81-7.74 (m, 1H), 3.67 (s, 3H); $^{19}$F-NMR (377 MHz, DMSO-d$_6$) δ −103.66, −115.63, −130.50, −133.66, −164.57.

As shown in Step 2 of Scheme 20, to a stirred solution of 4-chloro-2',3',4',6,6'-pentafluoro-N-methoxy-[1,1'-biphenyl]-3-sulfonamide (130 mg, 0.34 mmol) in DCM (3 mL) were added propionyl chloride (62 mg, 0.67 mmol), TEA (101 mg, 1.01 mmol), and DMAP (8 mg, 0.07 mmol). The resulting solution was stirred at 25° C. for 16 hours, diluted with water, and extracted with dichloromethane. The combined organic layers were washed with brine, dried over anhydrous sodium sulfate, filtered, and concentrated under reduced pressure. The residue was dissolved in DMF (0.5 mL) and purified by reversed-phase prep-HPLC (60-70% MeCN/0.1% aqueous formic acid) to afford N-benzyl-N-((4-chloro-2',3',4',6,6'-pentafluoro-[1,1'-biphenyl]-3-yl)sulfonyl)propionamide (Compound 76, 50 mg, 34% yield) as a white solid: MS (ESI) calc'd for $C_{16}H_{11}ClF_5NO_3S$ [M+1]$^+$=444.0, found 444.0; $^1$H-NMR (400 MHz, DMSO-d$_6$) δ 8.33 (d, J=7.2 Hz, 1H), 8.11 (d, J=9.6 Hz, 1H), 7.80-7.73 (m, 1H), 4.01 (s, 3H), 2.69 (q, J=7.2 Hz, 2H), 0.99 (t, J=7.2 Hz, 3H); $^{19}$F-NMR (377 MHz, DMSO-d$_6$) δ −101.75, −115.52, −130.55, −133.51, −164.68.

Example 19. Preparation of 1-((4-chloro-2',3',4',6,6'-pentafluoro-[1,1'-biphenyl]-3-yl)sulfonyl)propan-2-one (Compound 78)

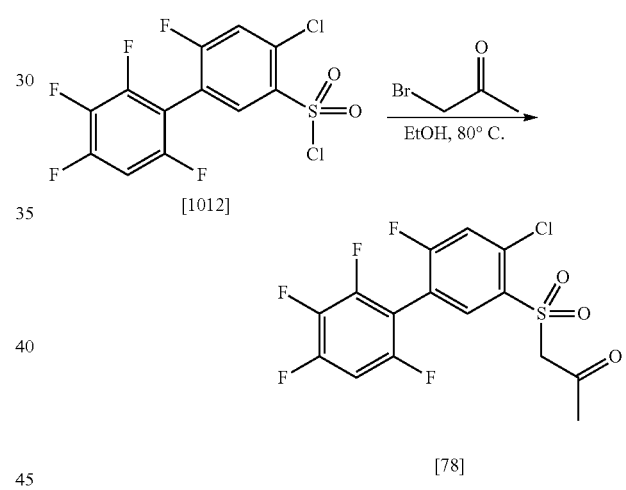

As shown in Scheme 21, to a solution of sodium 4-chloro-2',3',4',6,6'-pentafluoro-[1,1'-biphenyl]-3-sulfinate (140 mg, 0.38 mmol) in EtOH (7 mL) was added bromoacetone (52 mg, 0.38 mmol) slowly at 25° C. The reaction mixture was stirred at 25° C. for 16 hours, followed by concentration under reduced pressure. The residue was dissolved in DMF (2 mL) and purified by reversed-phase prep-HPLC (44-54% MeCN/0.1% aqueous formic acid) to afford 1-((4-chloro-2',3',4',6,6'-pentafluoro-[1,1'-biphenyl]-3-yl)sulfonyl)propan-2-one (Compound 78, 22.0 mg, 14%) as a white solid: MS (ESI) calc'd for $C_{15}H_8ClF_5O_3S$ [M−1]$^-$=397.0, found 397.0; $^1$H-NMR (400 MHz, DMSO-d$_6$) δ 8.22 (d, J=7.6 Hz, 1H), 8.12 (d, J=9.2 Hz, 1H), 7.80-7.74 (m, 1H), 4.89 (s, 3H), 2.25 (s, 3H); $^{19}$F-NMR (377 MHz, DMSO-d$_6$) δ −102.80, −115.60, −130.62, −133.65, −164.64.

Reacting Compound 1012 with 1-bromobutan-2-one in manner similar to that for the conversion of Compound 1012 to Compound 78 afforded 1-((4-chloro-2',3',4',6,6'-pentafluoro-[1,1'-biphenyl]-3-yl)sulfonyl)butan-2-one (Compound 79): MS (ESI) calc'd for $C_{16}H_{10}ClF_5O_3S$ [M−1]$^-$= 411.0, found 411.0; $^1$H-NMR (400 MHz, DMSO-d$_6$) δ 8.20

(d, J=7.2 Hz, 1H), 8.18 (d, J=9.2 Hz, 1H), 7.80-7.74 (m, 1H), 4.93 (s, 2H), 2.52 (q, J=7.2 Hz, 2H), 0.92 (t, J=7.2 Hz, 3H); $^{19}$F-NMR (377 MHz, DMSO-$d_6$) δ -102.84, -115.62, -130.62, -133.65, -164.59.

BIOLOGICAL EXAMPLES

Example 20. *Amaranthus tuberculatum* Protoporphyrinogen Oxidase (AmPPO) Expression and Purification The coding sequence of AmPPO was optimized for *E. coli* expression and assembled from synthetic oligonucleotides. Synthetic fragments were introduced into a pET28b vector (Novagen) using restriction-less "Hot Fusion" cloning process (Fu C., et al., 'Hot Fusion: An Efficient Method to Clone Multiple DNA Fragments as Well as Inverted Repeats without Ligase,' PLoS One (2014) Vol. 9(12), page e115318). The resulting DNA was sequence-verified. Construct encoding mutant version (ΔG210-AmPPO) of the enzyme was produced via PCR-based mutagenesis using Q5 mutagenesis kit (NEB).

Lysogeny broth (LB media, 10 mL) supplemented with 100 μg/mL kanamyci was inoculated with a single colony of BL21(DE3) competent *E. coli* transformed with pET28b_PPO_CHis. [Is pET28b_PPO_CHis. The culture was grown at 37° C. with shaking at 230 rpm overnight. This culture was then used to inoculate 1 L of autoinduction media (AIM) prepared by the method of Fox, B. G., & Blommel, P. G. (2009), Autoinduction of protein expression, 'Current Protocols in Protein Science,' Chapter 5, Unit-5.23. The resulting culture was grown at 37° C. with shaking at 230 rpm for 4 to 6 hours and an additional 40 to 48 hours at 18° C. The culture was collected and centrifuged. The resulting AmPPO enzyme-containing cell pellets were frozen and stored at -80° C. for future use.

The same procedure used to produce AmPPO was used to produce mutant ΔG210-AmPPO (a PPO mutant in which the *Glycine* at position 210 is absent), except *E. coli* used was transformed with pET28b_ΔG210 PPO_Chis.

A detergent solution was prepared by mixing together the following: 175 mL of B-PER Thermo Scientific); 75 mL of Y-PER (Thermo Scientific); 15 mL of 1M TRIS buffer, pH 9.0, 15 mL of 5M NaCl; 50 mL of glycerol; 2.5 mL of Triton-X100; and 1 mg of Flavin Adenine Dinucleotide (FAD). A portion of this solution (about 80 mL-100 mL) is set aside and supplemented with imidazole to a final concentration of 10 mM and a pH of pH 8.0. The remainder of detergent solution was supplemented with Hen Egg White Lysozyme (Gold Bio, 1 mg/mL) and Serratia endonuclease (produced in house) and added to about 45 g of frozen enzyme-containing cell pellets, which were allowed to thaw in the lysis solution with vigorous stirring for 30 minutes at room temperature, then briefly sonicated (30 seconds on 50% power using a VWR brand sonic disruptor). Incubation was continued with stirring for additional 15-30 minutes at 4° C. The lysate was clarified for 35 minutes by centrifugation at 14,000 RPM. The resulting clarified lysate was incubated for 1 hour at 4° C. with gentle stirring with His-SELECT® resin (Sigma, 20 mL of 50% slurry in 20% ethanol, washed 2× with 30 mM TRIS pH 8.1, 10% glycerol, 220 mM NaCl). The resin slurry was transferred to a disposable plastic column and washed with 10 mM Imidazole, 250 mM NaCl, 30 mM TRIS pH 8.5, 10% glycerol until the bound protein was deemed sufficiently washed away from lysate components (about 6-8 column volumes). The resin was then washed thoroughly (about 3 column volumes) with the previously set-aside detergent 1-10 final buffer, followed by elution with the same buffer supplemented with 250 mM imidazole, pH 8.1. Enzyme-containing fractions were collected and pooled based on SDS-PAGE analysis. Pooled fractions were diluted with pure glycerol to final concentration of 50% and the AmPPO enzyme or mutant ΔG210-AmPPO was stored at -20° C. in liquid form.

Example 21. PPO In Vitro Assay

Protoporphyrinogen IX (PPGIX) is prepared by reduction of protoporphyrin IX (PPIX) with a sodium amalgam as described by Jacobs and Jacobs, Enyzme 28: 206 (1982). Once prepared, the PPGIX solution is kept in the dark and all subsequent manipulations of it are performed in the dark.

The Base Buffer for the assay was 50 mM TRIS pH 8.5, 160 mM NaCl, 2 mM DTT, 0.01% Triton X-100. An antifoam solution was prepared by two serial 1 to 10 dilutions of Antifoam B Emulsion (SigmaAldrich) with Milli-Q water. Buffer A was freshly prepared by diluting AmPPO or mutant ΔG210-AmPPO in Base Buffer to 3-8 ug/ml concentration of enzyme. Buffer B was prepared by adding 2 ml of reduced 2 mM PPIX to 60 ml of Base Buffer and adjusting the pH back to 8.5 using glacial acetic acid. Finally, antifoam B (Sigma) was added to 0.01% final concentration. Buffer B was protected from light and used within 3 hours of its preparation.

A 384 well, clear bottom plate was used for the assay. Each test compound was dissolved in DMSO to a concentration of 30 mM. The test compounds, tested in triplicate, a butafenacil control, and a DMSO control were dispensed as 1.2 μL drops into a well of the plate. The wells were diluted with 60 μL of Buffer A and serially diluted 1 volume to 3 volumes over 7 dilutions by removing 20 μL from the first well, mixing well with 40 μL of Buffer A in a second well, removing 20 μL from the second well, and continuing the dilutions in this manner until there were 8 test wells. To initiate the reaction, 40 μL of Buffer B was added to each well and the wells gently mixed at least 2 times. The plate was centrifuged at 2000 rpm for 1 minute and the absorbance or fluorescence were read at ambient temperature using a plate reader. $IC_{50}$'s were calculated using a nonlinear regression Sigmoidal dose-response model (GraphPad Prism, variable slope) with curve bottoms constrained to zero and curve tops constrained to plate-specific $V_{average}$.

Each of Compounds 3 to 24, 26 to 34, 37 to 38, 41, 43 to 44, 46 to 54, 56, 59 to 67, and 69 to 79 had an $IC_{50}$ of less than 100 nM in the PPO in vitro assay. Compounds 25, 35 to 36, 39 to 40, 42, 45, 55, 57 to 58, and 68 had an $IC_{50}$'s of less than 1 μM in this assay.

Each of Compounds 4, 13 to 14, 17 to 20, 22 to 24, 26 to 27, 29, 31 to 34, 38, 41, 44, 47, 51 to 53, 56, 59 to 60, 64 to 65, 75, and 77 to 79 had an $IC_{50}$ of less than 100 nM in the ΔG210 PPO in vitro assay. Compounds 3, 5 to 12, 15 to 16, 21, 28, 30, 37, 42 to 43, 46, 48 to 50, 61 to 63, 66 to 67, 70 to 74, and 76 had an $IC_{50}$ of less than 1 μM in this assay.

Example 22. Testing the Post-Emergence Herbicidal Activity of Compounds of the Invention Selected compounds of the invention were screened at 100 PPM against *Amaranthus retroflexus* (AMARE), *Echinochloa crus-galli* (ECHCG), *Kochia scoparia* (KCHSC), and *Setaria italica* (SETIT).

Accordingly, PPO susceptible weed seeds were sown in 5"×5" pots by quadrant containing Miracle-Gro potting mix (Scotts Miracle-Gro Company, Marysville, OH, USA) and grown in a Conviron growth chamber with appropriate growth conditions (temperature of 26/22° C. with photoperiod 16/8 h light day/night and light intensity of 300 μmol m$^{-2}$ s$^{-1}$ supplemented by LED lamps). Relative humidity in the growth chamber was maintained at around 65%. Plants were grown until 2-4 leaf stage and thinned to 5-8 plants per quadrant per species.

Compounds were formulated in 25% Acetone, 1% Crop oil concentrate (COC-Agridex), 0.1% Tween-20, and 2.5% Ammonium sulphate (AMS). Three replicate pots were treated with each compound. Treatment consisting of the above formulation excluding active compound was applied as a treatment control (TC). Plants were treated with the test compound solution in a laboratory spray chamber fitted with 8003 flat fan nozzles calibrated to deliver 187-200 L ha$^{-1}$ at 269 kPa. Plants were placed back in the growth chamber and evaluated for % visual injury compared to TC 7 days after treatment (DAT). The data presented in Table 3 indicate a percentage control, where 100% control indicates complete inhibition of growth.

TABLE 3

Post-emergence herbicidal activity of selected compounds of the invention 7 days after the compound application

| Cmpd. No. | Post-emergence (100 ppm) | | | |
|---|---|---|---|---|
| | ECHCG | SETIT | KCHSC | AMARE |
| 6 | 10% | 8% | 12% | 100% |
| 7 | 37% | 28% | 20% | 100% |
| 8 | 28% | 23% | 23% | 100% |
| 16 | 95% | 43% | 8% | 33% |
| 17 | 100% | 100% | 13% | 88% |
| 18 | 100% | 100% | 23% | 100% |
| 26 | 100% | 100% | 15% | 100% |

Example 23. Testing the Pre-Emergence Herbicidal Activity of Compounds of the Invention Selected compounds of the invention were screened at 200 PPM against *Amaranthus retroflexus* (AMARE).

Accordingly, PPO susceptible weed seeds were planted in 5"×5" pots by quadrant containing custom field soil mix (Sandy loam with 4.7% OM, pH 7.0) and covered with a fine layer of the same soil. Compounds were formulated in 25% Acetone, 1% Crop oil concentrate (COC-Agridex), 0.1% Tween-20, and 2.5% Ammonium sulphate (AMS). Three replicate pots were treated with each compound. Treatment consisting of the above formulation excluding active compound was applied as a treatment control (TC). Pots were treated with the test compound solution in a laboratory spray chamber fitted with 8003 flat fan nozzles calibrated to deliver 187-200 L ha-1 at 269 kPa. Compound was incorporated into the soil by simulating rainfall equivalent to 0.2 mm using the same track sprayer. Subsequently, pots were irrigated from the bottom until assessed for % growth and germination inhibition. Pots were placed back in the growth chamber and evaluated for % growth and germination inhibition compared to TC 7 days after treatment (DAT). Growth conditions are similar to the ones mentioned in POST emergence assay.

The data presented in Table 4 indicate a percentage control, where 100% control indicates complete inhibition of growth and germination.

TABLE 4

Pre-emergence herbicidal activity of selected compounds of the invention 7 days after the compound application

| Cmpd. No. | AMARE pre-emergence (200 ppm) |
|---|---|
| 16 | 100% |
| 17 | 100% |
| 18 | 100% |
| 26 | 100% |

What is claimed is:

1. A compound of formula (I):

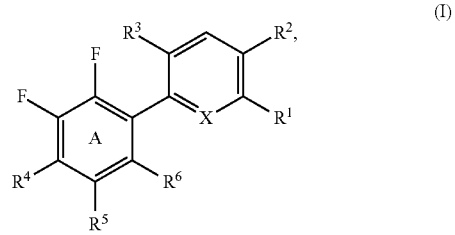

or suitable salt thereof, wherein:
X is —CH or —N;
R$^1$ is —SR$^{1a}$ or —S(O)$_2$R$^{1b}$;
R$^{1a}$ is C$_{1-4}$alkyl optionally substituted with phenyl, C(O)OR$^{1c}$, or C(O)N(R$^{1c}$)$_2$;
each R$^{1c}$ is independently, H, CH$_2$CH$_2$OC(O)R$^{1d}$, or optionally substituted C$_{1-4}$alkyl, wherein the optional substituents are C$_{3-6}$cycloalkyl, C(O)OC$_{1-4}$alkyl, or up to 3 F atoms, or two R$^{1c}$ with an intervening nitrogen atom form a 5-6 membered ring optionally substituted with C(O)OH or C(O)OC$_{1-4}$alkyl;
R$^{1d}$ is C$_{1-4}$alkyl or C$_{1-4}$alkenyl;
R$^{1b}$ is CH$_2$C(O)C$_{1-4}$alkyl or N(R$^{1e}$)R$^{1f}$;
R$^{1e}$ is H, C$_{1-4}$alkyl, C$_{1-4}$alkenyl, C$_{1-4}$alkynyl, C(O)C$_{1-2}$alkyl, or OC$_{1-4}$alkyl;
R$^{1f}$ is H, C$_{1-6}$alkyl, C(O)C(O)C$_{1-4}$alkyl, C(O)R$^{1g}$, or S(O)$_2$R$^{1g}$, or R$^{1e}$ and R$^{1f}$ together with the intervening nitrogen atom form a 5-6 membered ring, optionally containing up to two C(O) ring members;
R$^{1g}$ is C$_{1-4}$alkyl, C$_{1-4}$alkenyl, phenyl, Het, N(R$^h$)$_2$, OC$_{1-4}$alkyl, C$_{3-6}$cycloalkyl, or CH$_2$(OCH$_2$CH$_2$)$_4$CH$_3$, wherein each alkyl group is optionally substituted with up to 3 F atoms, phenyl, C$_{3-6}$cycloalkyl, OH, OC$_{1-4}$alkyl, wherein each cycloalkyl group is optionally substituted with OH or OC$_{1-4}$alkyl, wherein each phenyl is optionally substituted with up to 3 Cl or F atoms, and wherein Het is a 5-6 membered heterocyclic ring containing up to two ring members selected from O, N, S, or S(O)$_2$ and optionally substituted with OH or OC$_{1-4}$alkyl;
each R$^h$ is, independently H, C$_{1-4}$alkyl, benzyl, or phenyl;
each of R$^2$ and R$^3$ is Cl or F; and
each of R$^4$, R$^5$, and R$^6$ is F or H, wherein Ring A comprises at least 4 F atoms.

2. The compound according to claim 1, or a salt thereof, wherein R$^1$ is —SR$^{1a}$, and wherein R$^{1a}$ is C$_{1-4}$alkyl substituted with phenyl, C(O)OR$^{1c}$, or C(O)N(R$^{1c}$)$_2$.

3. The compound according to claim 1, or a salt thereof, wherein R$^1$ is —S(O)$_2$R$^{1b}$, and wherein R$^{1b}$ is CH$_2$C(O)C$_{1-4}$alkyl.

4. The compound according to claim 1, or a salt thereof, wherein R$^1$ is —S(O)$_2$R$^{1b}$, and wherein R$^{1b}$ is N(R$^{1e}$)R$^{1f}$.

5. The compound according to claim 1 having formula (II):

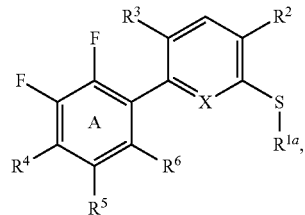

or a salt thereof.

6. The compound according to claim 5, or a salt thereof, wherein each of $R^4$, $R^5$, and $R^6$ is F.

7. The compound according to claim 5, or a salt thereof, wherein each of $R^4$ and $R^6$ is F.

8. The compound according to claim 5, or a salt thereof, wherein each of $R^4$ and $R^5$ is F.

9. The compound according to claim 5, or a salt thereof, wherein $R^{1a}$ is $C_{1-4}$alkyl substituted with $C(O)N(R^{1c})_2$; one $R^{1c}$ is H; and the other $R^{1c}$ is $C_{1-4}$alkyl substituted with $C(O)OC_{1-4}$alkyl.

10. The compound according to claim 1 having formula (III):

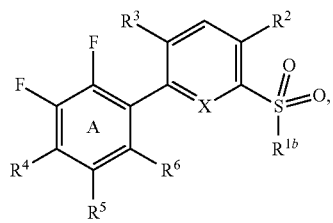

or a salt thereof.

11. The compound according to claim 10, or a salt thereof, wherein each of $R^4$, $R^5$, and $R^6$ is F.

12. The compound according to claim 10, or a salt thereof, wherein each of $R^4$ and $R^6$ is F.

13. The compound according to claim 10, or a salt thereof, wherein each of $R^4$ and $R^5$ is F.

14. The compound according to claim 10, or a salt thereof, wherein $R^{1f}$ is $C(O)R^{1g}$; and $R^{1g}$ is $C_{1-6}$alkyl, $C_{3-6}$cycloalkyl, or $OC_{1-4}$alkyl.

15. A compound selected from the group consisting of:

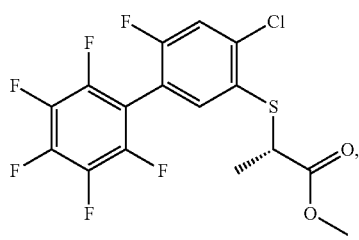

-continued

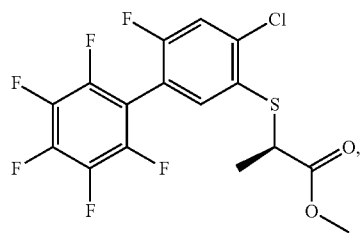

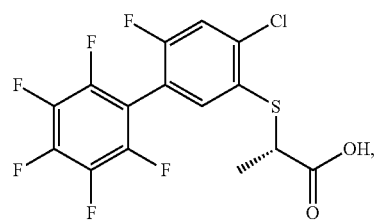

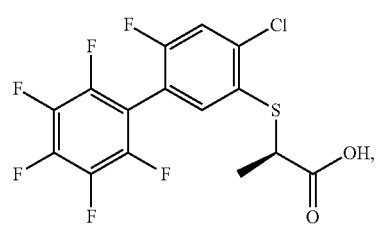

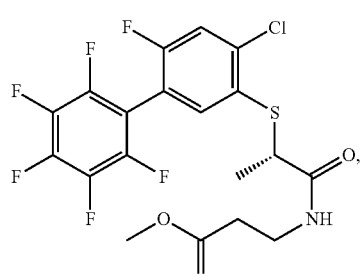

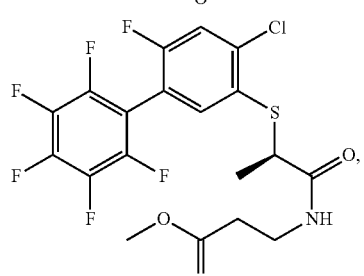

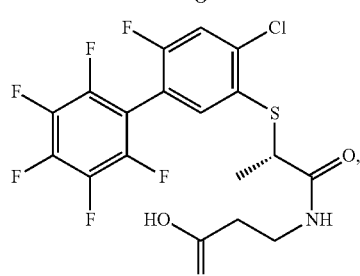

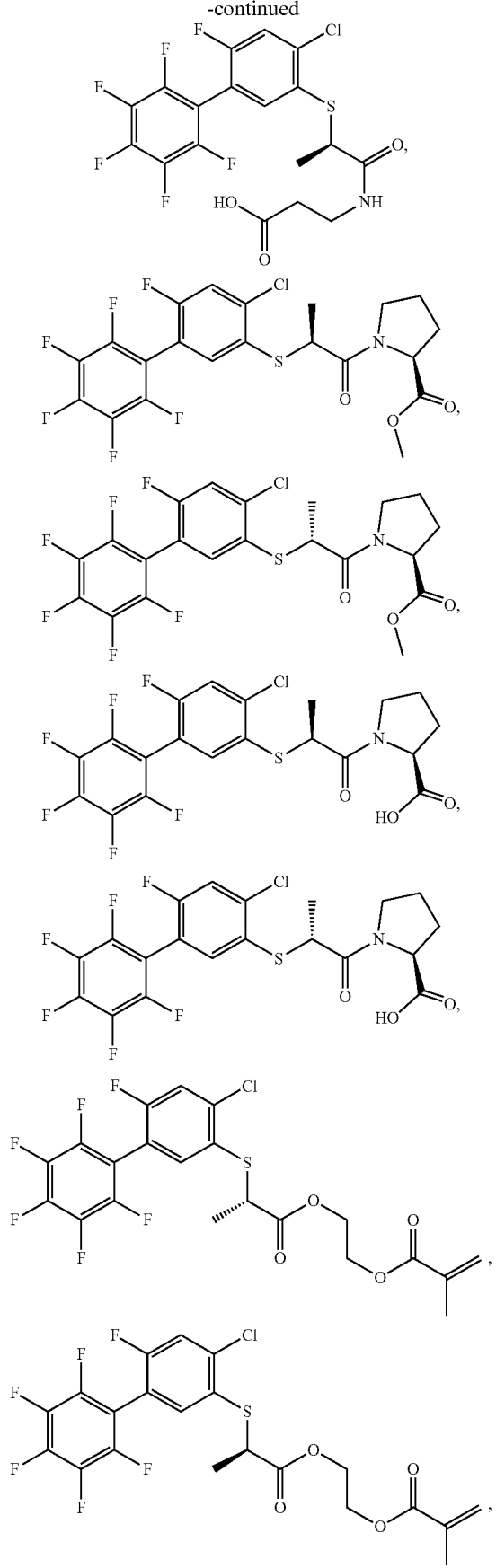
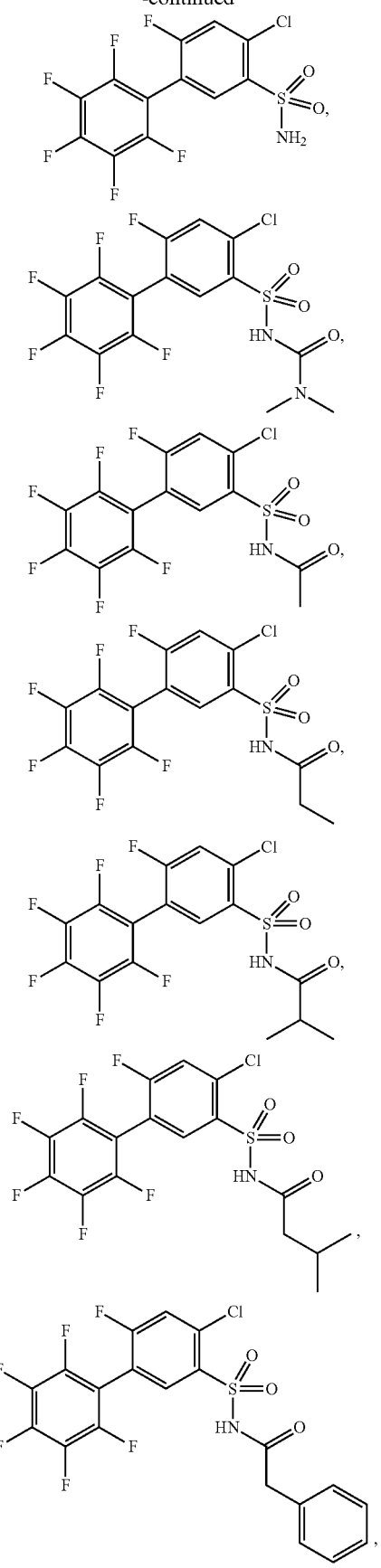

-continued
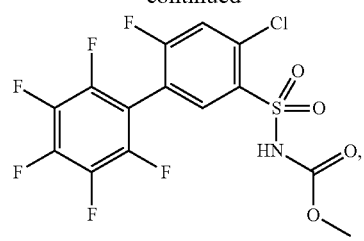
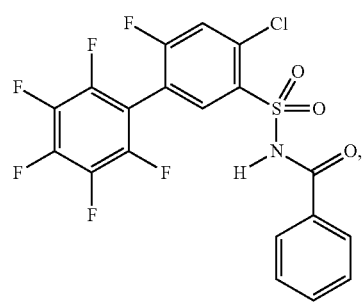
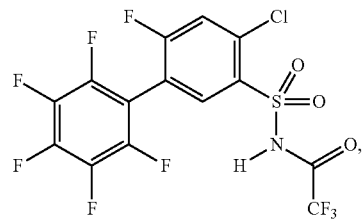
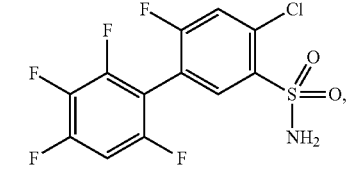
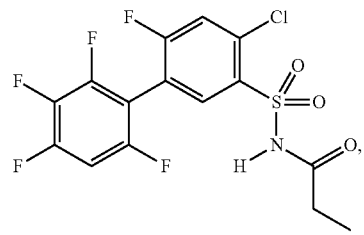
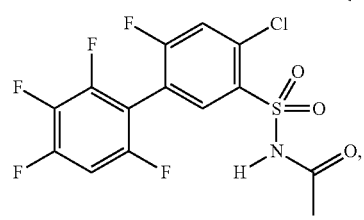
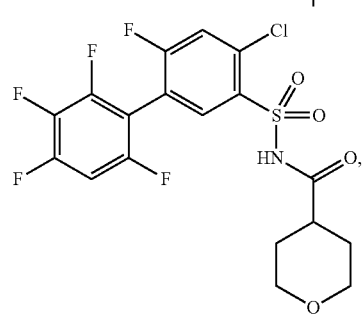
-continued
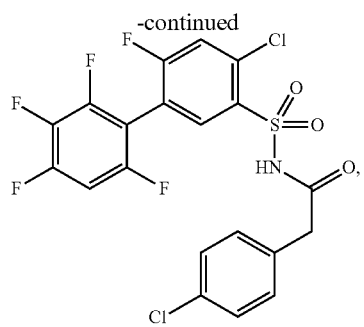
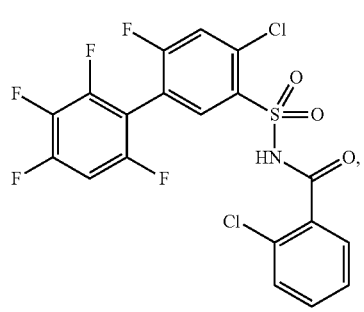
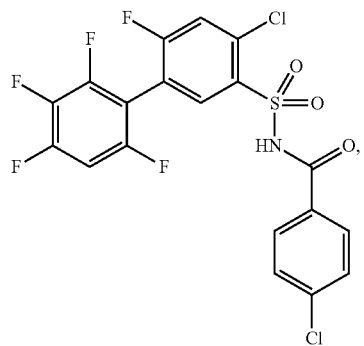
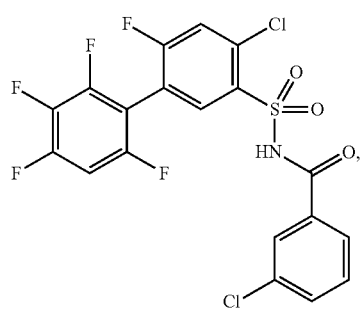
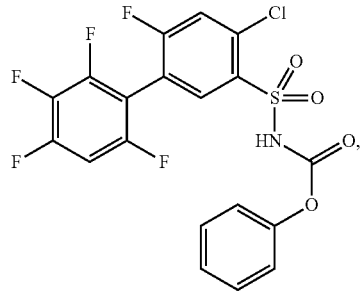

109
-continued
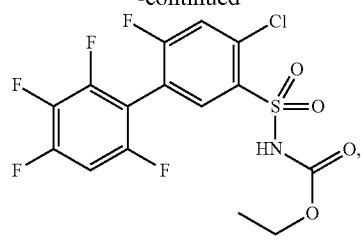
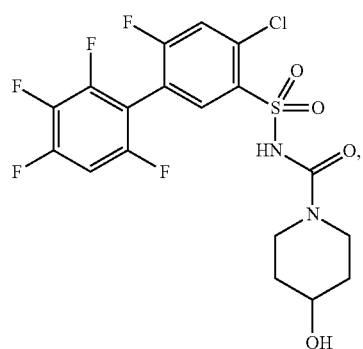
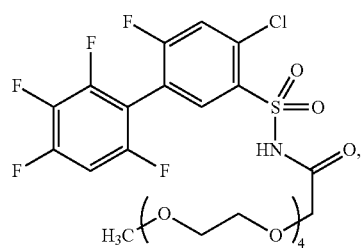
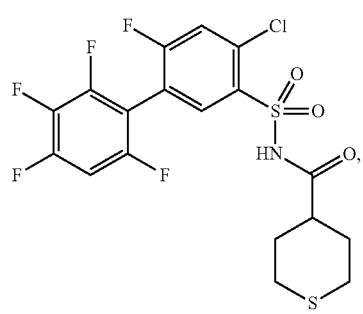
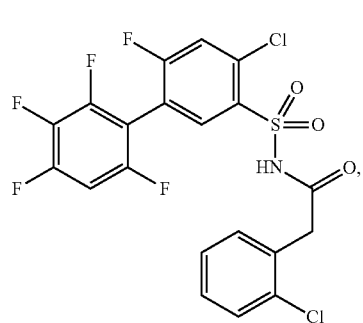
110
-continued
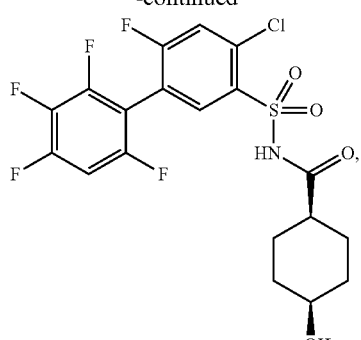
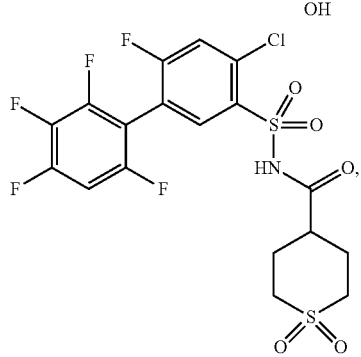
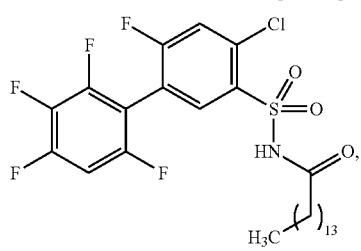
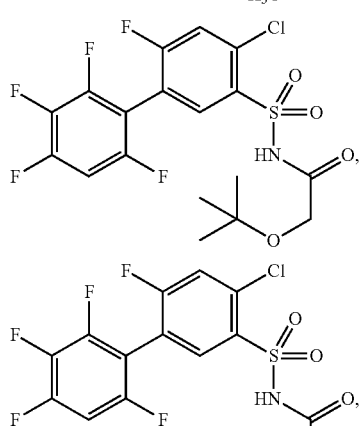
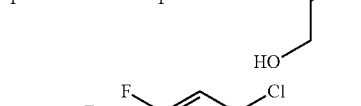
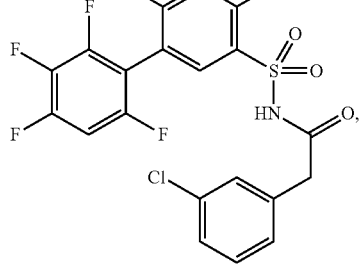

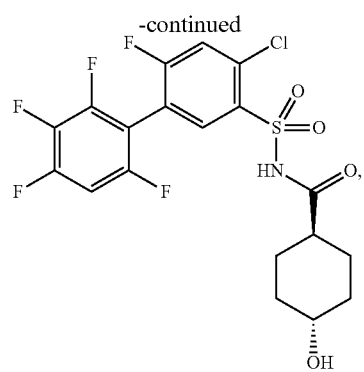
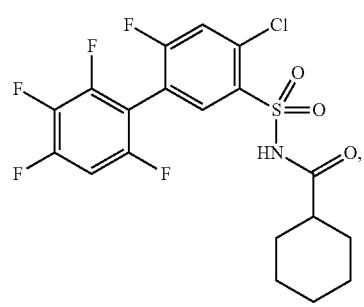
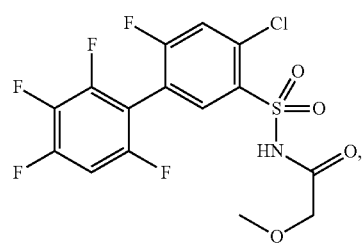
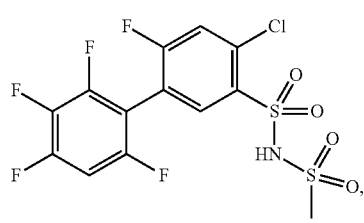
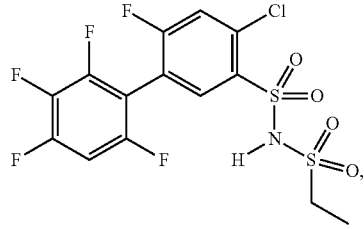
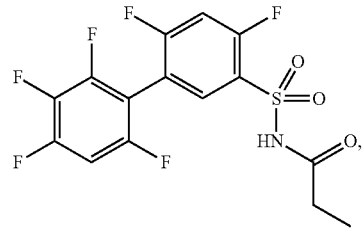
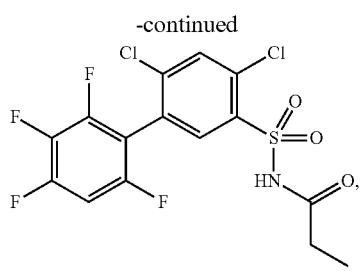
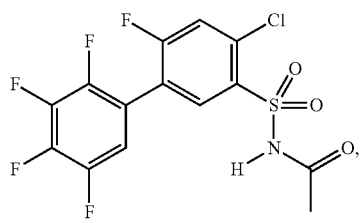
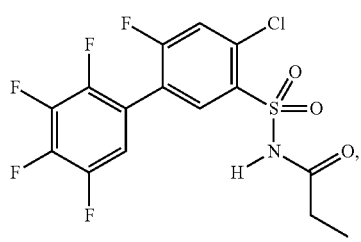
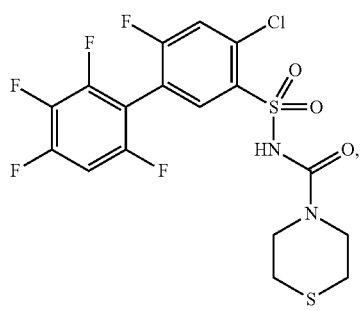
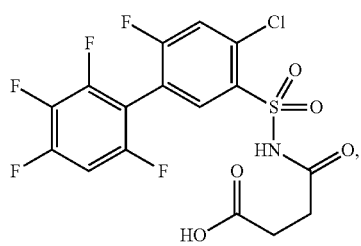
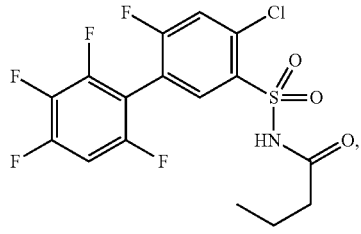

-continued
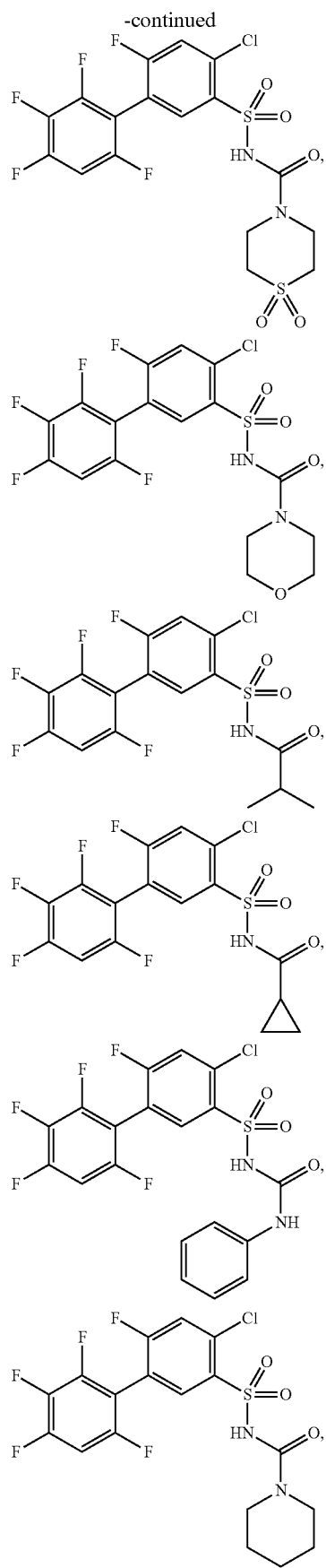
-continued
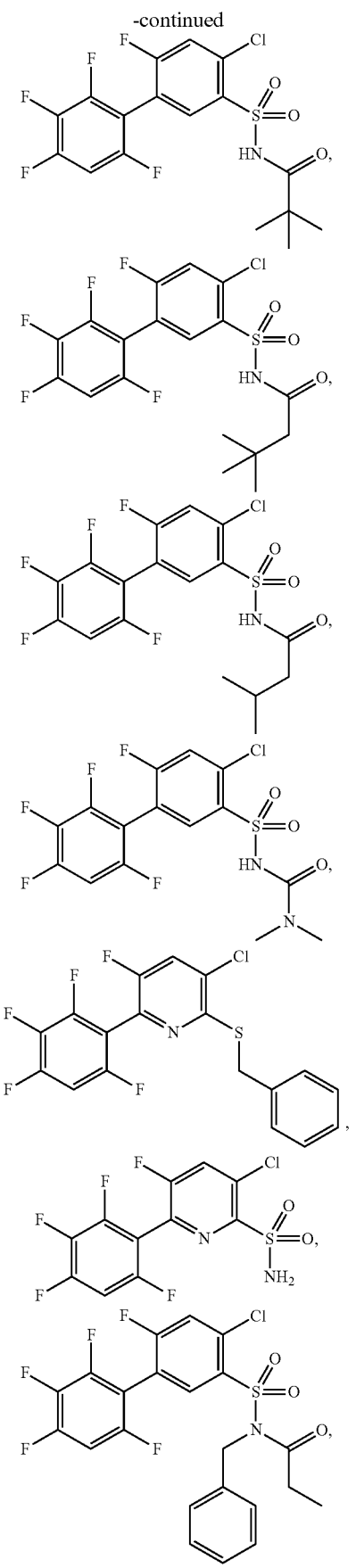

-continued

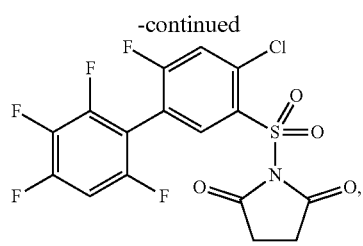

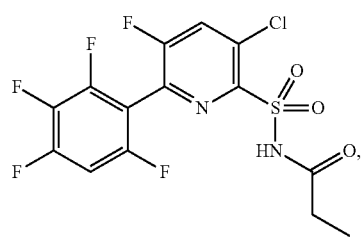

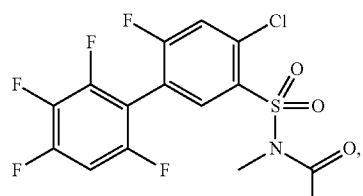

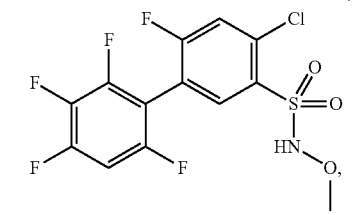

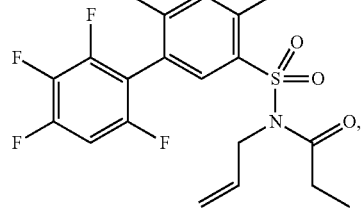

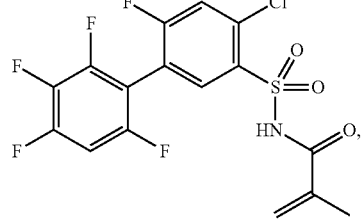

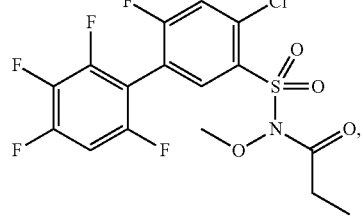

-continued

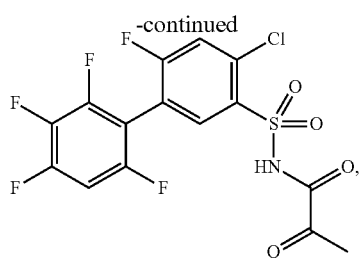

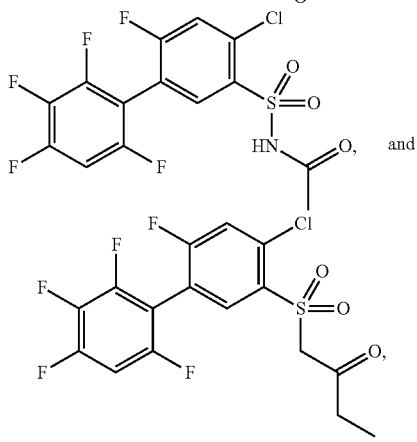

or a salt thereof.

16. An agricultural composition comprising the compound of claim 1, or a salt thereof, and at least one additional component that serves as a carrier.

17. The composition of claim 16, wherein at least one additional component is a surfactant or a diluent.

18. The composition of claim 16, wherein the composition is an herbicidal composition.

19. A method of controlling undesired vegetation, said method comprising contacting said vegetation or its environment with an herbicidally effective amount of the compound of claim 1, or a salt thereof.

20. The method of claim 19, wherein the undesired vegetation comprises weeds.

21. The method of claim 19, wherein the undesired vegetation comprises protoporphyrinogen IX oxidase (PPO) inhibitor-resistant weeds.

22. The method of claim 21, wherein the PPO inhibitor-resistant weeds have a dG210 mutation.

23. The method of claim 19, wherein the compound or composition is applied at a rate of 1 to 100 g per 10,000 m$^2$.

24. The method of claim 19, wherein contacting the undesired vegetation or its environment with the compound or composition leads to postemergence control of the undesired vegetation.

25. The method of claim 19, wherein contacting the undesired vegetation or its environment with the compound or composition leads to preemergence control of the undesired vegetation.

26. The method of claim 19, wherein the undesired vegetation is at least 60% controlled.

27. An agricultural composition comprising the compound of claim 15, or a salt thereof, and at least one additional component that serves as a carrier.

28. The composition of claim 27, wherein at least one additional component is a surfactant or a diluent.

29. The composition of claim 27, wherein the composition is an herbicidal composition.

30. A method of controlling undesired vegetation, said method comprising contacting said vegetation or its environment with an herbicidally effective amount of the compound of claim 15, or a salt thereof.

31. The method of claim 30, wherein the undesired vegetation comprises weeds.

32. The method of claim 30, wherein the undesired vegetation comprises protoporphyrinogen IX oxidase (PPO) inhibitor-resistant weeds.

33. The method of claim 32, wherein the PPO inhibitor-resistant weeds have a dG210 mutation.

34. The method of claim 32, wherein the compound or composition is applied at a rate of 1 to 100 g per 10,000 m$^2$.

35. The method of claim 32, wherein contacting the undesired vegetation or its environment with the compound or composition leads to postemergence control of the undesired vegetation.

36. The method of claim 32, wherein contacting the undesired vegetation or its environment with the compound or composition leads to preemergence control of the undesired vegetation.

37. The method of claim 32, wherein the undesired vegetation is at least 60% controlled.

\* \* \* \* \*